(12) United States Patent
Saito et al.

(10) Patent No.: US 8,911,740 B2
(45) Date of Patent: Dec. 16, 2014

(54) PHARMACEUTICAL COMPOSITION FOR TREATING AND/OR PREVENTING CANCER

(75) Inventors: Takanori Saito, Kanagawa (JP); Fumiyoshi Okano, Kanagawa (JP); Shinichi Kobayashi, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 13/577,028

(22) PCT Filed: Feb. 4, 2011

(86) PCT No.: PCT/JP2011/052382
§ 371 (c)(1),
(2), (4) Date: Aug. 3, 2012

(87) PCT Pub. No.: WO2011/096517
PCT Pub. Date: Aug. 11, 2011

(65) Prior Publication Data
US 2013/0071398 A1 Mar. 21, 2013

(30) Foreign Application Priority Data
Feb. 4, 2010 (JP) .................... 2010-023450

(51) Int. Cl.
A61K 39/395 (2006.01)
C07K 16/30 (2006.01)
C07K 16/18 (2006.01)
A61K 39/00 (2006.01)

(52) U.S. Cl.
CPC ....... A61K 39/39533 (2013.01); C07K 2317/24 (2013.01); C07K 16/3053 (2013.01); C07K 2317/23 (2013.01); C07K 2317/734 (2013.01); C07K 16/3015 (2013.01); C07K 2317/34 (2013.01); A61K 2039/505 (2013.01); C07K 2317/732 (2013.01); C07K 16/18 (2013.01); C07K 16/30 (2013.01)
USPC .................. 424/155.1; 424/133.1; 424/138.1; 424/139.1

(58) Field of Classification Search
None
See application file for complete search history.

(56) References Cited

U.S. PATENT DOCUMENTS

| | | |
|---|---|---|
| 5,698,396 A | 12/1997 | Pfreundschuh |
| 6,335,170 B1 | 1/2002 | Orntoft |
| 6,444,425 B1 | 9/2002 | Reed et al. |
| 7,449,184 B2 | 11/2008 | Allison et al. |
| 7,485,302 B2 | 2/2009 | Adams et al. |
| 7,745,391 B2 | 6/2010 | Mintz et al. |
| 8,008,431 B2 | 8/2011 | Weinschenk et al. |
| 8,211,634 B2 | 7/2012 | DePinho et al. |
| 2002/0006404 A1 | 1/2002 | Hanna et al. |
| 2003/0118599 A1 | 6/2003 | Algate et al. |
| 2003/0190640 A1 | 10/2003 | Faris et al. |
| 2004/0029114 A1 | 2/2004 | Mack et al. |
| 2004/0236091 A1 | 11/2004 | Chicz et al. |
| 2004/0258678 A1 | 12/2004 | Bodary et al. |
| 2005/0003390 A1 | 1/2005 | Axenovich et al. |
| 2005/0032113 A1 | 2/2005 | Tanaka et al. |
| 2005/0244413 A1* | 11/2005 | Adolf et al. ................ 424/144.1 |
| 2006/0019256 A1 | 1/2006 | Clarke et al. |
| 2006/0069054 A1 | 3/2006 | Houghton et al. |
| 2006/0275305 A1 | 12/2006 | Bryant |
| 2007/0048301 A1 | 3/2007 | Bodary-Winter et al. |
| 2007/0154931 A1 | 7/2007 | Radich et al. |
| 2007/0264253 A1 | 11/2007 | Liu et al. |
| 2008/0075722 A1 | 3/2008 | DePinho et al. |
| 2008/0107668 A1 | 5/2008 | Philip et al. |
| 2010/0029573 A1 | 2/2010 | Weinschenk et al. |
| 2010/0068724 A1 | 3/2010 | Fung et al. |
| 2011/0123492 A1 | 5/2011 | Okano et al. |
| 2011/0136121 A1 | 6/2011 | Okano et al. |
| 2011/0189700 A1 | 8/2011 | Moses et al. |
| 2011/0256144 A1* | 10/2011 | Okano et al. ................ 424/139.1 |
| 2012/0294860 A1 | 11/2012 | Ido et al. |
| 2012/0301471 A1 | 11/2012 | Kobayashi et al. |
| 2012/0301476 A1 | 11/2012 | Okano et al. |
| 2012/0321641 A1* | 12/2012 | Okano et al. ................ 424/158.1 |
| 2013/0045210 A1 | 2/2013 | Kobayashi et al. |
| 2013/0071398 A1 | 3/2013 | Saito et al. |

FOREIGN PATENT DOCUMENTS

| | | |
|---|---|---|
| CN | 1678338 A | 10/2005 |
| CN | 1705676 A | 12/2005 |
| CN | 101120252 A | 2/2008 |
| CN | 101189516 A | 5/2008 |

(Continued)

OTHER PUBLICATIONS

Strome et al., The Oncologist, 2007; 12:1084-95.*

(Continued)

*Primary Examiner* — Sheela J Huff
*Assistant Examiner* — Jessica H Roark
(74) *Attorney, Agent, or Firm* — Birch, Stewart, Kolasch & Birch, LLP

(57) ABSTRACT

According to the present invention, a cancer antigen protein to be specifically expressed on the surfaces of cancer cells is identified and thus the use of an antibody targeting the cancer antigen protein as an agent for treating and/or preventing cancer is provided. Specifically, the present invention provides a pharmaceutical composition for treating and/or preventing a cancer, which comprises an antibody or a fragment thereof as an active ingredient having immunological reactivity with a partial polypeptide of CAPRIN-1, which is represented by any of even-numbered sequences of SEQ ID NOS: 2 to 30, wherein the polypeptide has the amino acid sequence represented by SEQ ID NO: 37 or an amino acid sequence having 80% or more sequence identity with the amino acid sequence represented by SEQ ID NO: 37.

13 Claims, 3 Drawing Sheets

(56) References Cited

FOREIGN PATENT DOCUMENTS

| | | |
|---|---|---|
| CN | 102170907 A | 8/2011 |
| EP | 1557172 A1 | 7/2005 |
| EP | 2322221 A1 | 5/2011 |
| JP | 2002-540790 A | 12/2002 |
| JP | 2003-528587 A | 9/2003 |
| JP | 2006-316040 A | 11/2006 |
| RU | 2234942 C2 | 8/2004 |
| RU | 2306952 C2 | 9/2007 |
| RU | 2006 137 060 A | 4/2008 |
| RU | 2006137060 A | 4/2008 |
| WO | WO 00/04149 A2 | 1/2000 |
| WO | WO 00/60077 A2 | 10/2000 |
| WO | WO 01/32910 A2 | 5/2001 |
| WO | WO 01/72295 A2 | 10/2001 |
| WO | WO 02/078524 A2 | 10/2002 |
| WO | WO 02/083070 A2 | 10/2002 |
| WO | WO 02/092001 A2 | 11/2002 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116051 A2 | 12/2005 |
| WO | WO 2006/002378 A2 | 1/2006 |
| WO | WO 2007/150077 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2010/016525 A1 | 2/2010 |
| WO | WO 2010/016526 A1 | 2/2010 |
| WO | WO 2010/016527 A1 | 2/2010 |
| WO | WO 2011/096517 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/096535 A1 | 8/2011 |
| WO | WO 2013/018885 A1 | 2/2013 |
| WO | WO 2013/018886 A1 | 2/2013 |
| WO | WO 2013/018894 A1 | 2/2013 |

OTHER PUBLICATIONS

Brand et al., Anticancer Res. 2006; 26:463-70.*
Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Ellis et al., "Identification and Characterization of a Novel Protein (p137) Which Transcytoses Bidirectionally in Caco-2 Cells", The Journal of Biological Chemistry vol. 270, No. 35, Issue of Sep. 1, 1995, pp. 20717-20723.
Grill et al., "Activation/Division of Lymphocytes Results in Increased Levels of Cytoplasmic Activation/Proliferation-Associated Protein-1: Prototype of a New Family of Proteins", The Journal of Immunology, 2004, vol. 172: pp. 2389-2400.
Katsafanas et al., "Vaccinia Virus Intermediate Stage Transcription Is Complemented by Ras-GTPase-activating Protein SH3 Domain-binding Protein (G3BP) . . . ", The Journal of Biological Chemistry vol. 279, No. 50, Issue of Dec. 10, 2004, pp. 52210-52217.
Kolobova et al., "Microtubule-dependent association of AKAP350A and CCAR1 with RNA stress granules", Experimental Cell Research 315 (2009), pp. 542-555.
Solomon et al., "Distinct Structural Features of Caprin-1 Mediate Its Interaction with G3BP-1 and Its Induction of Phosphorylation of Eukaryotic Translation Initiation Factor 2a, . . . ", Molecular and Cellular Biology vol. 27, No. 6, Mar. 2007, pp. 2324-2342.
Wang et al., "Absence of Caprin-1 Results in Defects in Cellular Proliferation", The Journal of Immunology, 2005, vol. 175: pp. 4274-4282.
Chinese Office Action dated Mar. 29, 2013 for Chinese Application No. 200980139037.
Lu et al., "Targeting serum antibody for cancer diagnosis: a focus on colorectal cancer," Oncologic, Endocrine & Metabolic, Expert Opinion on Therapeutic Targets, vol. 11, No. 2, Feb. 2007, pp. 235-244.
NCBI Reference Sequence, caprin-1 [*Bos taurus*], Feb. 23, 2013, Accession No. NP001069530, XP615677, 1 page.
NCBI Reference Sequence, caprin-1 [*Gallus gallus*], Feb. 22, 2013, Accession No. NP001026536, XP423820, 1 page.
NCBI Reference Sequence, caprin-1 isoform 1 [*Homo sapiens*], Mar. 17, 2013, Accession No. NP005889, 3 pages.
NCBI Reference Sequence, caprin-1 isoform 2 [*Homo sapiens*], Mar. 3, 2013, Accession No. NP976240, 3 pages.
NCBI Reference Sequence, caprin-1 isoform a [*Mus musculus*], Mar. 23, 2013, Accession No. NP058019, 3 pages.
NCBI Reference Sequence, caprin-1 isoform b [*Mus musculus*], Mar. 23, 2013, Accession No. NP001104760, 3 pages.
NCBI Reference Sequence, caprin-1 isoform c [*Mus musculus*], Mar. 23, 2013, Accession No. NP001104761,4 pages.
NCBI Reference Sequence, Predicted: caprin-1 [*Equus caballus*], Jun. 27, 2011, Accession No. XP001492799, 1 page.
NCBI Reference Sequence, Predicted: caprin-1 isoform 2 [*Canis lupus familiaris*], Dec. 2, 2011, Accession No. XP858109, 1 page.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
GeneCards, "Cell Cycle Associated Protein 1-Biological research products for CAPRIN 1", updated Mar. 19, 2013, 10 pages.
Karauzum et al., "Caprin 1 is Frequently Overexpressed in Human Lymphomas," American Society of Human Genetics, Cancer Genetics, Program No. 1190W, Oct. 12, 2011, Abstract only.
United States Office Action, dated Jul. 1, 2013, for U.S. Appl. No. 13/577,212.
United States Office Action, dated Jul. 16, 2013, for U.S. Appl. No. 13/057,709.
Akiyoshi, "Cancer Vaccine Therapy Using Peptides Derived from Tumor-rejection Antigens," Jpn. J. Cancer Chemother., vol. 24, No. 5, Mar. 1997, pp. 511-519, with English Abstract (p. 519).
Bodey et al., "Failure of Cancer Vaccines: The Significant Limitations of this Approach to Immunotherapy," Anticancer Research, vol. 20, 2000, pp. 2665-2676.
Brass et al., "Translation initiation factor eIF-4gamma is encoded by an amplified gene and induces an immune response in squamous cell lung carcinoma," Human Molecular Genetics, vol. 6, No. 1, 1997, pp. 33-39.
Chamberlain et al., "Innovations and strategies for the development of anticancer vaccines," Expert Opinion on Pharmacotherapy, vol. 1, No. 4, 2000, pp. 603-614.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Gure et al., "SSX: A Multigene Family with Several Members Transcribed in Normal Testis and Human Cancer," Int. J. Cancer, vol. 72, 1997, pp. 965-971.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
Itoh et al., "HUB1 is an autoantigen frequently eliciting humoral immune response in patients with adult T cell leukemia," Int. J. Oncol., vol. 14, 1999, pp. 703-708 (Agstract only provided).
Jang et al., "Antihypertensive Angiotensin I-Converting Enzyme Inhibitory Activity and Antioxidant Activity of Vitis hybrid-*Vitis coignetiae* Red Wine Made with *Saccharomyces cerevisiae*," Mycobiology, vol. 39, No. 2, 2011, pp. 137-139.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Lu et al., "Identification of an immunological signature of tumor rejection in the neu transgenic mouse," 2007 AACR Annual Meeting,

(56) References Cited

OTHER PUBLICATIONS

Proceedings Abstract No. 4131, Apr. 14-18, 2007 (Presentation conducted on Apr. 17, 2007) (Abstract only provided).
Müller-Pillasch et al., "Identification of a new tumour-associated antigen TM4SF5 and its expression in human cancer," Gene, vol. 208, 1998, pp. 25-30.
Rauch et al., "SEREX, Proteomex, AMIDA, and beyond: Serological screening technologies for target identification," Proteomics Clin. Appl., vol. 2, 2008, pp. 355-371.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Characterization of Human Colon Cancer Antigens Recognized by Autologous Antibodies," Int. J. Cancer, vol. 76, 1998, pp. 652-658.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
Van Der Bruggen et al., "A Gene Encoding an Antigen Recognized by Cytolytic T Lymphocytes on a Human Melanoma," Science, vol. 254, No. 5038, Dec. 13, 1991, pp. 1643-1647 (Also published in J. Immunol., vol. 178, 2007, pp. 2617-2621).
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.
R & D Systems, "IHC Products & Protocol Guide," printed Jan. 9, 2014, pp. 1-112.
US Office Action for U.S. Appl. No. 13/057,515 dated Jan. 16, 2014.
Extended European Search Report for Application No. 11739876.8 dated Nov. 6, 2013.
United States Office Action for U.S. Appl. No. 13/576,950 dated Nov. 15, 2013.
Evans et al., "Vaccine therapy for cancer-fact or fiction?", Q. J. Med, vol. 92, 1999, pp. 299-307.
Extended European Search Report, dated Aug. 13, 2013, for European Application No. 11739882.6.
Harlow et al., "Antibodies A Laboratory Manual", Cold Spring Harbor Laboratory, Chapter 3, 1988, pp. 23-34.
Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.
Okano et al., "Identification of a novel target for antibody therapy of breast cancer", Cancer Research, vol. 72, Issue 8, Supplemental 1, Apr. 15, 2012, Abstract 519, 2 pages, XP-002700046.
Polyak et al., "Alanine-170 and proline-172 are critical determinants for extracellular CD20 epitopes; heterogeneity in the fine specificity of CD20 monoclonal antibodies is defined by additional requirements imposed by both amino acid . . . ", Blood, vol. 99, No. 9, May 1, 2002, pp. 3256-3262.
United States Office Action, dated Oct. 15, 2013, for U.S. Appl. No. 13/576,969.
United States Office Action, dated Oct. 21, 2013, for U.S. Appl. No. 13/577,212.
English translation of China Office Action for Appl. No. 201180016730.5 dated May 9, 2013.
English translation of Russian Notice of Allowance for Appl. No. 2011108260/10 dated Jun. 4, 2013.

* cited by examiner

PHARMACEUTICAL COMPOSITION FOR TREATING AND/OR PREVENTING CANCER

TECHNICAL FIELD

The present invention relates to a novel medical use of an antibody against CAPRIN-1 or a fragment thereof, as an agent, for treating and/or preventing a cancer.

BACKGROUND ART

Cancer is the leading cause of death. Currently conducted therapy comprises mainly surgical therapy in combination with radiation therapy and chemotherapy. In spite of the development of new operative procedures and the discovery of new anticancer agents in recent years, cancer treatment results have not been much improved recently, excluding that for some types of cancer. Recent advances in molecular biology or cancer immunology lead to identification of antibodies specifically reacting with cancer, cancer antigens to be recognized by cytotoxic T cells, genes encoding cancer antigens, and the like. Demands on specific cancer therapies targeting cancer antigens are increasing (Non-patent Literature 1).

In cancer therapy, it is desirable that peptides, polypeptides, or proteins recognized as antigens be almost absent in normal cells, but they be present specifically in cancer cells, in order to alleviate side effects. In 1991, Boon et al., (Ludwig Institute for Cancer Research, Belgium) isolated a human melanoma antigen MAGE1 recognized by CD8-positive T cells by the cDNA expression cloning method using autologous cancer cell lines and cancer-reactive T cells (Non-patent Literature 2). Thereafter, the SEREX (serological identification of antigens by recombinant expression cloning) method that comprises identifying tumor antigens recognized by antibodies that are produced in vivo in response to autologous cancer of a cancer patient by gene expression cloning techniques was reported (Non-patent Literature 3 and Patent Literature 1). With the use of this method, some cancer antigens, which are almost not expressed in normal cells but are expressed specifically in cancer cells, were isolated (Non-patent Literatures 4-9). Furthermore, clinical trials were conducted with cell therapies targeting some cancer antigens using immunocytes specifically reactive with cancer antigens, or cancer-specific immunotherapies using vaccines or the like containing cancer antigens.

Meanwhile, in recent years, various antibody medicines which target antigenic proteins on cancer cells for cancer treatment have appeared throughout the world. Antibody medicines exhibit some pharmacological effects as cancer specific therapeutic agents and are thus attracting attention. However, most antigen proteins to be targeted are also expressed in normal cells, so that not only cancer cells, but also normal cells expressing antigens are also damaged as a result of antibody administration. The resulting side effects are a cause for concern. Therefore, it is expected that identification of cancer antigens that are specifically expressed on the surface of a cancer cell and use of antibodies targeting the cancer antigens as pharmaceuticals will realize treatment with antibody medicines with lower side effects.

Cytoplasmic- and proliferation-associated protein 1 (CAPRIN-1) is expressed when normal cells at the resting phase are activated or undergo cell division, and it is an intracellular protein known to form intracellular stress granules with RNA within cells, so as to be involved in mRNA transport and translational regulation. Meanwhile, many other names that represent CAPRIN-1 exist, such as GPI-anchored membrane protein 1 or membrane component surface marker 1 protein (M11S1), as if such proteins had been known to be cell membrane proteins. These names originated from a report that the gene sequence of CAPRIN-1 is a membrane protein having a GPI-binding region and expressed in colorectal cancer cells (Non-patent Literature 10). However, the gene sequence of CAPRIN-1 provided in this report was later revealed to be wrong. The following has recently been reported; i.e., deletion of a single nucleotide in the gene sequence of CAPRIN-1 registered at GenBank or the like causes a frame shift, so that 80 amino acids are lost from the C-terminus, resulting in generation of an artifact (74 amino acids) which corresponds to the GPI-binding portion in the previous report, and additionally, another error is also present 5' of the gene sequence, so that 53 amino acids were lost from the N-terminus (Non-patent Literature 11). It has been also recently reported that the protein encoded by the gene sequence of CAPRIN-1 registered at GenBank or the like is not a cell membrane protein (Non-patent Literature 11).

In addition, on the basis of the report of Non-patent Literature 10 that CAPRIN-1 is a cell membrane protein, Patent Literatures 2 and 3 describe that CAPRIN-1 (as a cell membrane protein) under the name of M11S1 can be used as a target of an antibody medicine in cancer therapy, although working examples do not describe treatment using an antibody against the protein. However, as reported in Non-patent Literature 11, it has been commonly believed from the time of the filing of Patent Literature 2 to date that CAPRIN-1 is not expressed on the surface of a cell. The contents of Patent Literatures 2 and 3 based only on incorrect information that CAPRIN-1 is a cell membrane protein should not clearly be understood as common general knowledge for persons skilled in the art.

PRIOR ART LITERATURE

Patent Literature

Patent Literature 1: U.S. Pat. No. 5,698,396
Patent Literature 2: US2008/0075722
Patent Literature 3: WO2005/100998

Non-Patent Literature

Non-patent Literature 1: Tsuyoshi Akiyoshi, "Gan To Kagaku-Ryoho (Cancer and Chemotherapy)," 1997, Vol. 24, p 551-519 (Cancer and Chemotherapy Publishers, Inc., Japan)
Non-patent Literature 2 Bruggen P. et al., Science, 254: 1643-1647 (1991)
Non-patent Literature 3: Proc. Natl. Acad. Sci. U.S.A, 92: 11810-11813 (1995)
Non-patent Literature 4: Int. J. Cancer, 72: 965-971 (1997)
Non-patent Literature 5: Cancer Res., 58: 1034-1041 (1998)
Non-patent Literature 6: Int. J. Cancer, 29: 652-658 (1998)
Non-patent Literature 7: Int. J. Oncol., 14: 703-708 (1999)
Non-patent Literature 8: Cancer Res., 56: 4766-4772 (1996)
Non-patent Literature 9: Hum. Mol. Genet 6: 33-39, 1997
Non-patent Literature 10: J. Biol. Chem., 270: 20717-20723, 1995
Non-patent Literature 11: J. Immunol., 172: 2389-2400, 2004

SUMMARY OF THE INVENTION

Problem to be Solved by the Invention

Objects of the present invention are to identify a cancer antigen protein specifically expressed on the surface of a cancer cell and to provide the use of an antibody targeting the cancer antigen protein as an agent for treating and/or preventing a cancer.

Means for Solving the Problem

As a result of intensive studies, the present inventors have now obtained a cDNA encoding a protein that binds to an antibody existing in sera from dogs with breast cancer by the SEREX method using both cDNA libraries prepared from dog testis tissues and sera of dogs with breast cancer. The present inventors have now further prepared CAPRIN-1 proteins having the even-numbered amino acid sequences of SEQ ID NOS: 2 to 30 and antibodies against such CAPRIN-1 proteins based on the obtained dog gene and the corresponding human, cattle, horse, mouse, and chicken homologous genes. Thus, the present inventors have now found that CAPRIN-1 is specifically expressed in breast cancer, brain tumor, leukemia, lymphoma, lung cancer, uterine cervix cancer, bladder cancer, esophageal cancer, colorectal cancer, gastric cancer, and renal cancer cells, and that a portion of the CAPRIN-1 protein is specifically expressed on the surface of each cancer cell. The present inventors have thus now found that an antibody or antibodies against the portion of CAPRIN-1 expressed on the surface of each cancer cell is/are cytotoxic to the CAPRIN-1-expressing cancer cells. On the basis of these findings, the present invention as described below was completed.

The present invention has the following characteristics.

The present invention provides a pharmaceutical composition for treating and/or preventing a cancer, comprising an antibody or a fragment thereof as an active ingredient having immunological reactivity with a partial polypeptide of CAPRIN-1, wherein CAPRIN-1 is represented by any of the even-numbered sequences of SEQ ID NOS: 2 to 30, and wherein the partial polypeptide comprises the amino acid sequence represented by SEQ ID NO: 37 or an amino acid sequence having 80% or more sequence identity with the amino acid sequence of SEQ ID NO: 37.

In an embodiment, the above cancer is breast cancer, brain tumor, leukemia, lymphoma, lung cancer, uterine cervix cancer, bladder cancer, esophageal cancer, colorectal cancer, gastric cancer, or renal cancer.

In another embodiment, the antibody is a monoclonal antibody or a polyclonal antibody.

In another embodiment, the antibody is a human antibody, a humanized antibody, chimeric antibody, single chain antibody, or bispecific antibody.

In another embodiment, the antibody has an immunological reactivity with a polypeptide that has the amino acid sequence represented by SEQ ID NO: 37 or an amino acid sequence having 80% or more, preferably 85% or more, more preferably 90% or more, further preferably 95% or more sequence identity with the amino acid sequence of SEQ ID NO: 37, or with a fragment thereof.

In another embodiment, the antibody is the following antibody (a) or (b) having immunological reactivity with CAPRIN-1 protein, or the pharmaceutical composition for treating and/or preventing cancer is characterized by comprising such antibody as an active ingredient:
(a) an antibody which comprises a heavy chain variable region comprising SEQ ID NOS: 40, 41, and 42 and a light chain variable region comprising SEQ ID NOS: 44, 45, and 46; and
(b) an antibody which comprises a heavy chain variable region comprising SEQ ID NOS: 40, 41, and 42 and a light chain variable region comprising SEQ ID NOS: 50, 51, and 52.

This description includes all or part of the contents as disclosed in the description and/or drawings of Japanese Patent Application No. 2010-023450, from which the present application claims the priority.

Effects of the Invention

The antibody against CAPRIN-1 used in the present invention is cytotoxic to cancer cells. As such, the antibody against CAPRIN-1 is useful for treating or preventing cancers.

MODE FOR CARRYING OUT THE INVENTION

Figure 1:
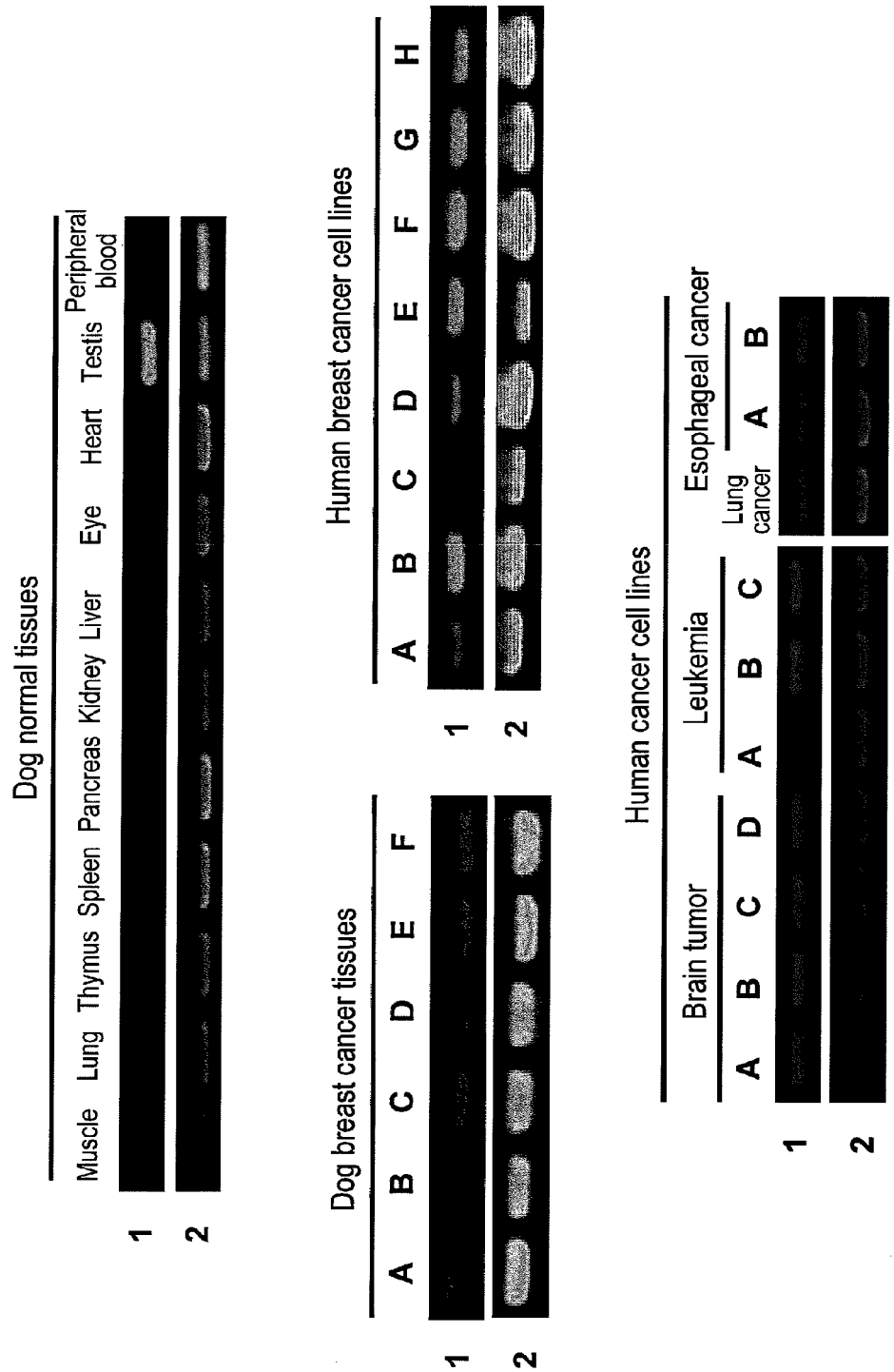
FIG. 1 shows the expression patterns of genes encoding CAPRIN-1 proteins in normal tissues and tumor cell lines. Reference No. 1 indicates the expression patterns of genes encoding CAPRIN-1 proteins, and Reference No. 2 indicates the expression patterns of GAPDH genes.

The anti-tumor activity of an antibody against a polypeptide represented by any of the even-numbered sequences of SEQ ID NOS: 2 to 30 used in the present invention can be evaluated by examining in vivo suppression of tumor growth in animals with cancer, or, examining whether or not the antibody exhibits cytotoxicity via immunocytes or complements to tumor cells expressing the polypeptide in vitro, as described later.

In the context, the nucleotide sequences of polynucleotides encoding proteins comprising the even-numbered amino acid sequences (i.e., SEQ ID NOS: 2, 4, 6, . . . , 28, 30) of SEQ ID NOS: 2 to 30 are represented by the odd-numbered sequences (i.e., SEQ ID NOS: 1, 3, 5, . . . , 27, 29) of SEQ ID NOS: 1 to 29.

The amino acid sequences that are represented by SEQ ID NOS: 6, 8, 10, 12, and 14 in the Sequence Listing disclosed herein are the amino acid sequences of CAPRIN-1 isolated as polypeptides, which bind to antibodies specifically existing in serum from a dog with cancer, through the SEREX method using a cDNA library from dog testis tissue and the serum of a dog with breast cancer. The amino acid sequences represented by SEQ ID NOS: 2 and 4 are the amino acid sequences of CAPRIN-1 isolated as human homologues. The amino acid sequence represented by SEQ ID NO: 16 is the amino acid sequence of CAPRIN-1 isolated as a cattle homologue. The amino acid sequence represented by SEQ ID NO: 18 is the amino acid sequence of CAPRIN-1 isolated as a horse homologue. The amino acid sequences represented by SEQ ID NOS: 20 to 28 are the amino acid sequences of CAPRIN-1 isolated as mouse homologues. The amino acid sequence represented by SEQ ID NO: 30 is the amino acid sequence of CAPRIN-1 isolated as a chicken homologue (see Example 1 described later). CAPRIN-1 is known to be expressed when normal cells in the resting phase are activated or give rise to cell division.

It was known that CAPRIN-1 was not expressed on cell surfaces. However, as a result of the examination by the present inventors, it has now revealed that a portion of the CAPRIN-1 protein is expressed on the surfaces of various cancer cells. It has thus been now revealed that an antibody recognizing a partial polypeptide of the CAPRIN-1 protein, which comprises the amino acid sequence represented by SEQ ID NO: 37 or an amino acid sequence having 80% or more, preferably 85% or more, more preferably 90% or more, further preferably 95% or more sequence identity with the amino acid sequence of SEQ ID NO: 37, exhibits anti-tumor activity. Examples of the antibody of the present invention include all antibodies which bind to a fragment of the above CAPRIN-1 protein and exhibit anti-tumor activity.

The above-described anti-CAPRIN-1 antibody used in the present invention may be any type of antibody as long as it can exhibit anti-tumor activity. Examples of such antibodies include monoclonal antibodies, polyclonal antibodies, recombinant antibodies, such as synthetic antibodies, multi-specific antibodies, humanized antibodies, chimeric antibodies, and single chain antibodies (scFv), human antibodies, and fragments thereof, such as Fab, F(ab')$_2$, and Fv. These antibodies and fragments thereof can be prepared by methods known by persons skilled in the art. In the present invention, antibodies having immunological reactivity with CAPRIN-1 proteins or partial polypeptides thereof (that is, binding to CAPRIN-1 proteins via antigen-antibody reaction) and preferably antibodies capable of specifically binding to CAPRIN-1 proteins are desired. Preferably, they are monoclonal antibodies. Polyclonal antibodies may also be used as long as homogenous antibodies can be stably produced. Also, when a subject is a human, human antibodies or humanized antibodies are desired in order to avoid or suppress rejection.

The term "specifically binding to CAPRIN-1 protein" as used herein means that the antibody specifically binds to a CAPRIN-1 protein, but does not substantially bind to proteins other than the CAPRIN-1 protein.

The anti-tumor activity of an antibody that can be used in the present invention can be evaluated as described below by examining in vivo the suppression of the tumor growth in animals with cancer, or, by examining whether or not it exhibits in vitro an activity of cytotoxicity, which is mediated by immunocytes or complements, to tumor cells expressing the polypeptide.

Furthermore, examples of the subject for cancer treatment and/or prevention in the present invention include mammals, such as humans, pet animals, domestic animals, and animals for competition. A preferable subject is a human.

Preparation of antigens and antibodies and pharmaceutical compositions relating to the present invention are described below.

<Preparation of Antigens for Antibody Preparation>

Proteins or fragments thereof to be used as sensitizing antigens for obtaining anti-CAPRIN-1 antibodies used in the present invention may be derived from any animal species without particular limitation, such as humans, dogs, cattle, horses, mice, rats, and chickens. However, proteins or fragments thereof are preferably selected in consideration of compatibility with parent cells used for cell fusion. In general, mammal-derived proteins are preferred and, in particular, human-derived protein is preferred. For example, when CAPRIN-1 is human CAPRIN-1, the human CAPRIN-1 protein, a partial peptide thereof, or cells expressing human CAPRIN-1 can be used.

The nucleotide sequences and the amino acid sequences of human CAPRIN-1 and homologues thereof can be obtained by accessing GenBank (NCBI, U.S.A.) and using an algorithm such as BLAST or FASTA (Karlin and Altschul, Proc. Natl. Acad. Sci. U.S.A., 90: 5873-5877, 1993; Altschul et al., Nucleic Acids Res. 25: 3389-3402, 1997).

In the present invention, on the basis of the nucleotide sequence (SEQ ID NO: 1 or 3) or the amino acid sequence (SEQ ID NO: 2 or 4) of human CAPRIN-1, a target nucleic acid or a target protein comprises a sequence having 70% to 100%, preferably 80% to 100%, more preferably 90% to 100%, even more preferably 95% to 100% (e.g., 97% to 100%, 98% to 100%, 99% to 100%, or 99.5% to 100%) sequence identity with the nucleotide sequence or the amino acid sequence of the ORF or the mature portion of human CAPRIN-1. As use herein, the term "% sequence identity" refers to a percentage (%) of identical amino acids (or nucleotides) relative to the total number of amino acids (or nucleotides), when two sequences are aligned to achieve the highest similarity with or without introduction of gaps.

The length of a fragment of CAPRIN-1 protein ranges from the amino acid length of an epitope (antigenic determinant), which is the minimum unit recognized by an antibody, to a length less than the full length of the protein. The term "epitope" refers to a polypeptide fragment having antigenicity or immunogenicity in mammals, preferably in humans, and the minimum unit of the epitope consists of about 7 to 12 amino acids, for example 8 to 11 amino acids. Therefore, the antibody of the present invention is characterized by recognizing a partial sequence (fragment) consisting of about 7 to 12 amino acids (e.g., 8 to 11 amino acids) in the amino acid sequence represented by SEQ ID NO: 37 or an amino acid sequence having 80% or more, preferably 85% or more, more preferably 90% or more, further preferably 95% or more sequence identity with the amino acid sequence of SEQ ID NO: 37. As such, the antibody is characterized by binding (preferably, specifically binding) to such a partial sequence (fragment).

The polypeptides comprising the above-mentioned human CAPRIN-1 protein or partial peptides of the protein, can be synthesized by a chemical synthesis method, such as the Fmoc method (fluorenylmethyloxycarbonyl method) or the tBoc method (t-butyloxycarbonyl method) (Eddited by The Japanese Biochemical Society, Seikagaku Jikken Koza (Biochemical Experimental Lecture Series) 1, Protein Chemistry IV, Chemical Modification and Peptide Synthesis, TOKYO KAGAKU DOZIN (Japan), 1981). Alternatively, the above-mentioned polypeptides may also be synthesized by conventional methods using various commercially available peptide synthesizers. Furthermore, with the use of known genetic engineering techniques (e.g., Sambrook et al., Molecular Cloning, 2$^{nd}$ Edition, Current Protocols in Molecular Biology (1989), Cold Spring Harbor Laboratory Press, Ausubel et al., Short Protocols in Molecular Biology, 3$^{rd}$ Edition, A compendium of Methods from Current Protocols in Molecular Biology (1995), John Wiley & Sons), a polynucleotide encoding the above polypeptide is prepared and then incorporated into an expression vector, which is subsequently introduced into a host cell in order to produce a polypeptide of interest in the host cell, and then recover it.

The polynucleotides encoding the above polypeptides can be easily prepared by known genetic engineering techniques or conventional techniques using a commercially available nucleic acid synthesizer. For example, DNA comprising the nucleotide sequence of SEQ ID NO: 1 can be prepared by PCR using a human chromosomal DNA or cDNA library, as a template, and a pair of primers designed to be able to amplify the nucleotide sequence represented by SEQ ID NO: 1. PCR conditions can be appropriately determined. For example, PCR conditions comprise conducting 30 cycles of the reaction cycle of: denaturation at 94° C. for 30 seconds; annealing at 55° C. for 30 seconds to 1 minute; and extension at 72° C. for 2 minutes, using a thermostable DNA polymerase (e.g., Taq polymerase or Pfu polymerase) and PCR buffer containing $Mg^{2+}$, followed by reacting at 72° C. for 7 minutes. However, the PCR conditions are not limited to the above example. PCR techniques, conditions, and the like are described in Ausubel et al., Short Protocols in Molecular Biology, 3rd Edition, A compendium of Methods from Current Protocols in Molecular Biology (1995), John Wiley & Sons (particularly Chapter 15).

Also, on the basis of the nucleotide sequence and amino acid sequence information represented by SEQ ID NOS: 1 to 30 in the Sequence Listing described herein, appropriate probes or primers are prepared, and then a cDNA library of a human or the like is screened using them, so that desired DNA can be isolated. A cDNA library is preferably constructed from cells, organs or tissues, which express proteins having even-numbered sequences of SEQ ID NOS: 2 to 30. Examples of such cells or tissues include cells or tissues derived from testis, and cancers or tumors, such as leukemia, breast cancer, lymphoma, brain tumor, lung cancer, colorectal cancer, and the like. Procedures such as the preparation of probes or primers, construction of a cDNA library, screening of a cDNA library, and cloning of target genes are known by a person skilled in the art and can be carried out by the methods described in Sambrook et al., Molecular Cloning, $2^{nd}$ Edition, Current Protocols in Molecular Biology (1989), Ausbel et al., (above), and the like. DNA encoding a human CAPRIN-1 protein or a partial peptide thereof can be obtained from the thus obtained DNA.

The host cells may be any cells, as long as they can express the above-mentioned polypeptide. Examples of prokaryotic cells include, but are not limited to, *Escherichia coli* and the like. Examples of eukaryotic cells include, but are not limited to, mammalian cells, such as monkey kidney cells (COS1) and Chinese hamster ovary cells (CHO), human fetal kidney cell line (HEK293), fetal mouse skin cell line (NIH3T3), yeast cells such as budding yeast and fission yeast, silkworm cells, and *Xenopus oocyte*.

When prokaryotic cells are used as host cells, an expression vector used herein contains an origin replicable within prokaryotic cells, a promoter, a ribosome-binding site, a multiple cloning site, a terminator, a drug resistance gene, an auxotrophic complementary gene, and the like. Examples of *Escherichia coli* expression vector include a pUC-based vector, pBluescript II, a pET expression system, and a pGEX expression system. DNA encoding the above polypeptide is incorporated into such an expression vector, prokaryotic host cells are transformed with the vector, the thus obtained transformed cells are cultured, and thus the polypeptide encoded by the DNA can be expressed in prokaryotic host cells. At this time, the polypeptide can also be expressed as a fusion protein with another protein.

When eukaryotic cells are used as host cells, an expression vector used herein is an expression vector for eukaryotic cells, which contains a promoter, a splicing region, a poly(A) addition site, and the like. Examples of such an expression vector include pKA1, pCDM8, pSVK3, pMSG, pSVL, pBK-CMV, pBK-RSV, EBV vector, pRS, pcDNA3, and pYES2. In a manner similar to the above, DNA encoding the above polypeptide is incorporated into such an expression vector, eukaryotic host cells are transformed with the vector, the thus obtained transformed cells are cultured, and thus the polypeptide encoded by the DNA can be expressed in eukaryotic host cells. When pIND/V5-His, pFLAG-CMV-2, pEGFP-N1, pEGFP-C1, or the like is used as an expression vector, the above polypeptide can be expressed as a fusion protein to which a tag from among various tags such as a His tag (e.g., $(His)_6$-$(His)_{10}$), a FLAG tag, a myc tag, an HA tag, and GFP has been added.

For introduction of an expression vector into host cells, a known method can be employed, such as electroporation, a calcium phosphate method, a liposome method, a DEAE dextran method, microinjection, viral infection, lipofection, and binding to a cell membrane-permeable peptide.

The polypeptide of interest can be isolated and purified from host cells by a combination of known separation procedures. Examples of such procedures include, but are not limited to, treatment with a denaturing agent such as urea or a surfactant, ultrasonication, enzymatic digestion, salting-out or solvent fractionation and precipitation, dialysis, centrifugation, ultrafiltration, gel filtration, SDS-PAGE, isoelectric focusing, ion exchange chromatography, hydrophobic chromatography, affinity chromatography, and reverse phase chromatography.

<Antibody Structure>

An antibody is a heteromultimeric glycoprotein that generally contains at least two heavy chains and two light chains. Antibodies other than IgM is an about 150-kDa heterotetramer glycoprotein composed of two identical light (L) chains and two identical heavy (H) chains. Typically, each light chain is connected to a heavy chain via one disulfide covalent bond, however, the number of disulfide bonds between heavy chains of various immunoglobulin isotypes is varied. Each heavy chain or each light chain also has an intrachain disulfide bond. Each heavy chain has a variable domain (VH region) on one end followed by several constant regions. Each light chain has a variable domain (VL region) and has one constant region on an end opposite to the other end. The constant region of a light chain is aligned with the first constant region of a heavy chain, and a light chain variable domain is aligned with a heavy chain variable domain. A specific region of an antibody variable domain exhibits specific variability that is referred to as a complementarity determining region (CDR), so that it imparts binding specificity to the antibody. A portion of a variable region, which is relatively conserved, is referred to as a framework region (FR). Complete heavy chain and light chain variable domains separately contains four FRs ligated via three CDRs. The three CDRs in a heavy chain are referred to as CDRH1, CDRH2, and CDRH3 in this order from the N-terminus. Similarly, in the case of a light chain, CDRLs are referred to as CDRL1, CDRL2, and CDRL3. CDRH3 is most important for the binding specificity of an antibody to an antigen. Also, the CDRs of each chain are retained together in a state of being adjacent to each other due to the FR regions, contributing to the formation of the antigen binding site of the antibody together with CDRs from the other chain. A constant region does not directly contribute to the binding of an antibody to an antigen, but exhibits various effector functions, such as involvement in antibody-dependent cell-mediated cytotoxicity (ADCC), phagocytosis via binding to an Fcy receptor, the rate of half-life/clearance via a neonate Fc receptor (FcRn), and complement-dependent cytotoxicity (CDC) via a C1q constituent of the complement cascade.

<Preparation of Antibody>

The term "anti-CAPRIN-1 antibody" as used herein refers to an antibody having immunological reactivity with a full-length CAPRIN-1 protein or a fragment thereof.

As used herein, the term "immunological reactivity" refers to the property of in vivo binding of an antibody to a CAPRIN-1 antigen. Through such an in vivo binding, the function of damaging tumor (e.g., death, suppression, or degeneration) is exhibited. Specifically, an antibody used in the present invention may be any type of antibody, as long as it binds to a CAPRIN-1 protein so as to be able to damage tumor, such as leukemia, lymphoma, breast cancer, brain tumor, lung cancer, esophageal cancer, gastric cancer, renal cancer, or colorectal cancer.

Examples of an antibody include a monoclonal antibody, a polyclonal antibody, a synthetic antibody, a multispecific antibody, a human antibody, a humanized antibody, a chimeric antibody, a single chain antibody, and an antibody fragment (e.g., Fab and F(ab')$_2$). Also, an antibody may be an immunoglobulin molecule of any class such as IgG, IgE, IgM, IgA, IgD, or IgY, or any subclass such as IgG1, IgG2, IgG3, IgG4, IgA1, or IgA2.

The antibody may further be modified by, in addition to glycosylation, acetylation, formylation, amidation, phosphorylation, pegylation (PEG), or the like.

Various antibody preparation examples are as described below.

When the antibody is a monoclonal antibody, for example, the breast cancer cell line SK-BR-3 expressing CAPRIN-1 is administered to a mouse for immunization, the spleen is removed from the mouse, cells are separated, and then the cells and mouse myeloma cells are fused. From among the thus obtained fusion cells (hybridomas), a clone producing an antibody having the effect of suppressing cancer cell proliferation is selected. A hybridoma producing a monoclonal antibody that has the effect of suppressing cancer cell proliferation is isolated, the hybridoma is cultured, and then an antibody is purified from the culture supernatant by general affinity purification, so that the antibody can be prepared.

The hybridoma producing a monoclonal antibody can also be prepared as described below, for example. First, an animal is immunized with a sensitizing antigen according to a known method. A general method is carried out by injecting a sensitizing antigen to a mammal intraperitoneally or subcutaneously. Specifically, a sensitizing antigen is diluted with PBS (Phosphate-Buffered Saline), saline, or the like to an appropriate amount, followed by suspension. The resultant is then mixed with an appropriate amount of a general adjuvant as necessary, such as Freund's complete adjuvant. After emulsification, the solution was administered to a mammal several times every 4 to 21 days. Furthermore, an appropriate carrier can also be used upon immunization with a sensitizing antigen.

A mammal is immunized as described above. After confirmation of a rise in a desired serum antibody level, immunized cells are collected from the mammal and then subjected to cell fusion. Preferable immunized cells are particularly splenocytes.

Mammalian myeloma cells are used as the other parent cells to be fused with the immunized cells. As the myeloma cells, various known cell lines are preferably used, such as P3U1 (P3-X63Ag8U1), P3 (P3x63Ag8. 653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), S194 (Trowbridge, I. S. J. Exp. Med. (1978) 148, 313-323), and 8210 (Galfre, G. et al., Nature (1979) 277, 131-133).

Fusion of the immunized cell and the myeloma cell can be carried out according to basically a known method such as Kohler and Milstein's technique (Kohler, G. and Milstein, C. Methods Enzymol. (1981) 73, 3-46), for example.

More specifically, the above cell fusion is carried out, for example, in the presence of a cell fusion accelerator in a usual nutrient culture medium. As this fusion accelerator, polyethyleneglycol (PEG), Sendai virus (HVJ), or the like is used. If desired, an auxiliary agent such as dimethylsulfoxide may be added and used in order to enhance fusion efficiency.

The ratio of the immunized cells to the myeloma cells to be used herein can be arbitrarily set. For example, the number of immunized cells that are preferably used is one to ten times the number of myeloma cells. As a culture medium to be used for the above-mentioned cell fusion, an RPMI1640 culture medium suitable for proliferation of the above-mentioned myeloma cell line, an MEM culture medium, and other culture media usually used for culturing this kind of cell can be used. Further, liquid that is supplemental to serum such as fetal bovine serum (FCS) can be used together therewith.

Cell fusion can be performed by thoroughly mixing the predetermined amounts of the above immunized cells and the myeloma cells in the above culture medium, and a PEG solution (for example, having an average molecular weight ranging from about 1000 to 6000) prewarmed at about 37° C. is added usually at a concentration of 30%-60% (w/v) and mixed, thereby forming a culture containing hybridomas of interest. Next, a suitable culture medium is successively added to the thus-obtained culture, which is then centrifuged to remove the supernatant, and this procedure is repeated to remove the cell fusion agent or the like which is not preferable for the growth of hybridomas.

The thus obtained hybridomas are cultured for selection in a usual selection culture medium (e.g., a HAT culture medium containing hypoxanthine, aminopterin and thymidine). Culturing in this HAT culture medium is continued for a sufficient period of time (usually several days to several weeks) so that the cells (non-fused cells) other than the target hybridomas die. Subsequently, screening and single cloning of the hybridoma which produces an antibody of interest are performed using the general limiting dilution method.

The above hybridomas are obtained by an immunizing non-human animal with an antigen. In addition to this method, hybridomas that produce a human antibody having desired activity (e.g., activity of suppressing cell proliferation) can also be obtained by in vitro sensitizing human lymphocytes, such as human lymphocytes that have been infected with the EB virus, with a protein, a protein-expressing cell, or a lysate thereof, followed by fusing of the thus sensitized lymphocytes with human-derived myeloma cells having an ability to permanently divide, such as U266 (registration no. TIB196).

The thus prepared hybridoma that produces a monoclonal antibody of interest can be passaged in a general culture medium and can be stored in liquid nitrogen over a long period of time.

Specifically, a hybridoma can be prepared by immunizing by a general immunization method using, as a sensitizing antigen, a desired antigen or a cell that expresses the desired antigen, fusing the thus obtained immunized cell with a known parent cell by a general cell fusion method, and then screening for a monoclonal antibody-producing cell (i.e., a hybridoma) by a general screening method.

Another example of an antibody that can be used in the present invention is a polyclonal antibody. A polyclonal antibody can be obtained as described below, for example.

A small animal, such as a mouse, a human antibody-producing mouse, or a rabbit, is immunized with a natural CAPRIN-1 protein, a recombinant CAPRIN-1 protein expressed in a microorganism such as *Escherichia coli* in the form of a fusion protein with GST or the like, or a partial peptide thereof, and then serum is obtained. The serum is purified by ammonium sulfate precipitation, protein A column, protein G column, DEAE ion exchange chromatography, affinity column to which a CAPRIN-1 protein or a synthetic peptide has been coupled, or the like, so that a polyclonal antibody can be prepared.

As a human antibody-producing mouse, a KM mouse (Kirin Pharma/Medarex) and a Xeno mouse (Amgen) are known (e.g., International Patent Publications WO02/43478 and WO02/092812), for example. When such a mouse is immunized with a CAPRIN-1 protein or a fragment thereof, a complete human polyclonal antibody can be obtained from blood. Also, splenocytes are collected from the immunized mouse and then a human-type monoclonal antibody can be prepared by a method for fusion with myeloma cells.

An antigen can be prepared according to a method using animal cells (JP Patent Publication (Kohyo) No. 2007-530068) or baculovirus (e.g., International Patent Publication WO98/46777), for example. When an antigen has low immunogenicity, the antigen may be bound to a macromolecule having immunogenicity, such as albumin, and then immunization is carried out.

Furthermore, an antibody gene is cloned from said hybridoma and then incorporated into an appropriate vector. The vector is then introduced into a host, and then the genetically recombined antibody produced using gene recombination techniques can be used (e.g., see Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA of a variable region (V region) of an antibody is synthesized from the mRNA of the hybridoma using reverse transcriptase. When DNA encoding the V region of an antibody of interest can be obtained, this DNA is ligated to DNA encoding the constant region (C region) of a desired antibody, and then the resultant fusion product is incorporated into an expression vector. Alternatively, DNA encoding the V region of an antibody may be incorporated into an expression vector containing the DNA for the C region of an antibody. At this time, the DNA can be incorporated into an expression vector so that it is expressed under the control of expression control regions, such as enhancer and promoter. Next, host cells are transformed with the expression vector, so that the antibody can be expressed.

The anti-CAPRIN-1 antibody of the present invention is preferably a monoclonal antibody. However, the anti-CAPRIN-1 antibody may also be a polyclonal antibody or a genetically-modified antibody (e.g., a chimeric antibody or a humanized antibody), for example.

Examples of a monoclonal antibody include human monoclonal antibodies, non-human animal monoclonal antibodies (e.g., a mouse monoclonal antibody, a rat monoclonal antibody, a rabbit monoclonal antibody, and a chicken monoclonal antibody), and chimeric monoclonal antibodies. A monoclonal antibody can be prepared by culturing a hybridoma obtained by cell fusion of a splenocyte from a non-human mammal (e.g., a mouse, a human antibody-producing mouse, a chicken, or a rabbit) immunized with a CAPRIN-1 protein, with a myeloma cell. A chimeric antibody is prepared by combining sequences from different animals, such as an antibody comprising heavy chain and light chain variable regions of a mouse antibody and heavy chain and light chain constant regions of a human antibody. A chimeric antibody can be prepared using a known method. For example, a chimeric antibody can be obtained by ligating DNA encoding an antibody V region to DNA encoding a human antibody C region, incorporating the resultant fusion product into an expression vector, and then introducing the vector into a host for production of the chimeric antibody. In Examples described later, human-chicken chimeric monoclonal antibodies were prepared and thus its anti-tumor effects were confirmed. These monoclonal antibodies contain a heavy chain variable (VH) region having the amino acid sequence of SEQ ID NO: 43 and a light chain variable (VL) region having the amino acid sequence of SEQ ID NO: 47 or SEQ ID NO: 53, wherein the VH region comprises CDR1 represented by the amino acid sequence of SEQ ID NO: 40, CDR2 represented by the amino acid sequence of SEQ ID NO: 41, and CDR3 represented by the amino acid sequence of SEQ ID NO: 42, and the VL region contains CDR1 represented by the amino acid sequence of SEQ ID NO: 44 or 50, CDR2 represented by the amino acid sequence of SEQ ID NO: 45 or 51, and CDR3 represented by the amino acid sequence of SEQ ID NO: 46 or 52.

Examples of a polyclonal antibody include an antibody obtained by immunizing a human antibody-producing animal (e.g., a mouse) with a CAPRIN-1 protein.

A humanized antibody is a modified antibody that is also referred to as a reshaped human antibody. A humanized antibody can be constructed by transplanting CDRs of an antibody from an immunized animal into the complementarity determining regions of a human antibody. General gene recombination techniques therefor are also known.

Specifically, DNA sequences designed to have each of the CDRs of a mouse or chicken antibody ligated to each of the framework regions (FRs) of a human antibody are synthesized by the PCR method from several oligonucleotides, which are prepared so as to have overlap portions at their terminal portions, for example. A humanized antibody can be obtained by ligating the thus obtained DNA to DNA encoding the constant region of a human antibody, incorporating the resultant fusion product into an expression vector, introducing the vector into a host, and thus causing the host to produce the gene product (see European Patent Publication No. 239400 and International Patent Publication WO96/02576). As the FRs of a human antibody, which is ligated via CDRs, FRs that allow the formation of an antigen-binding site with good complementarity determining regions are selected. If necessary, for the formation of an antigen-binding site having the appropriate complementarity determining regions of a reshaped human antibody, the amino acids of the framework regions of an antibody variable region may be substituted (Sato, K. et al., Cancer Research, 1993, 53: 851-856). Also, the amino acids of FRs may be substituted with those of framework regions from various human antibodies (see International Patent Publication WO99/51743).

As the framework regions (FRs) of a human antibody, which are ligated via CDRs, FRs that allows the formation of an antigen-binding site with good complementarity determining regions are selected. If necessary, for the formation of an antigen-binding site having the appropriate complementarity determining regions of a reshaped human antibody, the amino acids of the framework regions of an antibody variable region may be substituted (Sato K. et al., Cancer Research 1993, 53: 851-856).

After preparation of a chimeric antibody or a humanized antibody, amino acids in a variable region (e.g., FR) or a constant region may be substituted with other amino acids.

Amino acid substitution is a substitution of, for example, less than 15, less than 10, 8 or less, 7 or less, 6 or less, 5 or less, 4 or less, 3 or less, or 2 or less amino acids and is preferably a substitution of 1 to 5 amino acids, and more preferably 1 or 2 amino acids. A substituted antibody should be functionally equivalent to an unsubstituted antibody. Substitution is desirably a substitution of a conservative amino acid(s) between amino acids having analogous properties such as electric charge, side chain, polarity, and aromaticity. Amino acids having analogous properties can be classified into basic amino acids (arginine, lysine, and histidine), acidic amino acids (aspartic acid and glutamic acid), uncharged polar amino acids (glycine, asparagine, glutamine, serine, threonine, cysteine, and tyrosine), nonpolar amino acids (leucine, isoleucine, alanine, valine, proline, phenylalanine, tryptophan, and methionine), branched-chain amino acids (threonine, valine, and isoleucine), and aromatic amino acids (phenylalanine, tyrosine, tryptophan, and histidine), for example.

Examples of a modified antibody product include antibodies bound to various molecules such as polyethylene glycol (PEG). Substances to be bound in the modified antibody product of the present invention are not limited. Such a modified antibody product can be obtained by subjecting the thus obtained antibody to chemical modification. Methods therefor have already been established in the art.

As used herein, the term "functionally equivalent" refers to that a subject antibody has biological or biochemical activity similar to that of the antibody of the present invention, and specifically refers to that a subject antibody has the function of impairing tumor without essentially causing rejection upon its application to a human, for example. An example of such activity includes an activity to suppress cell proliferation or a binding activity.

As a method well known by persons skilled in the art for preparation of a polypeptide functionally equivalent to a polypeptide, a method for introducing a mutation into a polypeptide is known. For example, persons skilled in the art can prepare an antibody functionally equivalent to the antibody of the present invention by appropriately introducing a mutation into the antibody using site-directed mutagenesis (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. U.S.A. 82, 488-492; Kunkel (1988) Methods Enzymol. 85, 2763-2766), for example.

An antibody that recognizes an epitope of a CAPRIN-1 protein recognized by the above anti-CAPRIN-1 antibody can be obtained by a method known by persons skilled in the art. For example, such an antibody can be obtained by a method that involves determining an epitope of a CAPRIN-1 protein recognized by an anti-CAPRIN-1 antibody, by a general method (e.g., epitope mapping) and then preparing an antibody using a polypeptide having an amino acid sequence contained in the epitope as an immunogen, or a method that involves determining an epitope of such an antibody prepared by a general method, and then selecting an antibody having the epitope identical with that of an anti-CAPRIN-1 antibody. As used herein, the term "epitope" refers to, in a mammal and preferably a human, a polypeptide fragment having antigenicity or immunogenicity. The minimum size unit thereof consists of about 7 to 12 amino acids, and preferably 8 to 11 amino acids.

The affinity constant Ka ($k_{on}/k_{off}$) of the antibody of the present invention is preferably at least $10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, or at least $10^{13}$ M$^{-1}$.

The antibody of the present invention can be conjugated with an antitumor agent. Conjugation of the antibody with an antitumor agent can be carried out via a spacer having a group reactive to an amino group, a carboxyl group, a hydroxy group, a thiol group or the like (e.g., a succinimidyl succinate group, a formyl group, a 2-pyridyldithio group, a maleimidyl group, an alkoxy carbonyl group, and a hydroxy group).

Examples of the antitumor agent include the following known antitumor agents as in prior art literatures and the like, such as paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycinl, cryptophycin8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitomycinC, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elfornithine, elliptinium acetate, epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethyl hydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatrexate, daunomycin, aminopterin, xeloda, ibandronate, irinotecan, topoisomerase inhibitor, difluoromethylolnitine (DMFO), retinoic acid, capecitabine, and pharmaceutically acceptable salts or derivatives thereof.

Through administration of the antibody of the present invention in combination with an antitumor agent, even higher therapeutic effects can be obtained. This technique is applicable to both before and after surgery of a cancer patient with the expression of CAPRIN-1. In particular, through application of the technique after surgery, more effective prevention of cancer recurrences or prolonged survival period can be obtained against cancer with the expression of CAPRIN-1, which has been conventionally treated with an antitumor agent alone.

Examples of the antitumor agent to be administered in combination with the antibody of the present invention include the following known antitumor agents as in prior art literatures or the like, such as paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycinl, cryptophycin8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitomycinC, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elfornithine, elliptinium acetate, epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethyl hydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatrexate, daunomycin, aminopterin, xeloda, ibandronate, irinotecan, topoisomerase inhibitor, difluoromethylolnitine (DMFO), retinoic acid, capecitabine, and pharmaceutically acceptable (known) salts or (known) derivatives thereof. Of the above examples, particularly cyclophosphamide, paclitaxel, docetaxel, and vinorelbine are preferably used.

Alternatively, a known radio isotope as in prior art literatures or the like, such as $^{211}$At, $^{131}$I, $^{125}$I, $^{90}$Y, $^{186}$Re, $^{188}$Re, $^{153}$Sm, $^{212}$Bi, $^{32}$P, $^{175}$Lu, or $^{176}$Lu can be bound to the antibody of the present invention. A desired radio isotope is effective for treatment or diagnosis of tumor.

The antibody of the present invention is an antibody having immunological reactivity with CAPRIN-1, an antibody specifically recognizing CAPRIN-1, or an antibody specifically binding to CAPRIN-1, which exhibits cellular cytotoxic activity against cancer or the effect of suppressing tumor growth. The antibody should have a structure such that rejection is almost or completely avoided in a subject animal to which the antibody is administered. Examples of such an antibody include, when a subject animal is human, human antibody, humanized antibody, chimeric antibody (e.g., human-mouse chimeric antibody), single chain antibody, and bispecific antibody. These antibodies are: recombinant antibodies in which heavy chain and light chain constant regions and variable regions are both from a human antibody; recombinant antibodies in which complementarity determining regions (CDRs) (CDR1, CDR2, and CDR3) of heavy chain and light chain variable regions are from a non-human animal antibody, and, framework regions and heavy chain and light chain constant regions are from a human antibody; or recombinant antibodies in which heavy chain and light chain variable regions are from a non-human animal antibody, and, heavy chain and light chain constant regions are from a human antibody. Preferable antibodies are the former two antibodies.

These recombinant antibodies can be prepared as follows by cloning DNA encoding an anti-human CAPRIN-1 monoclonal antibody (e.g., a human monoclonal antibody, a mouse monoclonal antibody, a rat monoclonal antibody, a rabbit monoclonal antibody, or a chicken monoclonal antibody) from an antibody-producing cell such as a hybridoma, preparing DNA encoding a light chain variable region and a heavy chain variable region of the antibody by an RT-PCR method using it as a template, and then determining the sequence of each variable region of light chain and heavy chain or each sequence of CDR1, CDR2, and CDR3 based on a Kabat EU numbering system (Kabat et al., Sequences of Proteins of Immunological Interest, 5$^{th}$ Ed. Public Health Service, National Institute of Health, Bethesda, Md. (1991)).

Furthermore, DNA encoding each of these variable regions or DNA encoding each CDR is prepared using recombinant DNA techniques (Sambrook et al., Molecular Cloning: A Laboratory Manual, Cold Spring Harbor Laboratory Press (1989)) or a DNA synthesizer. Here, the above human monoclonal antibody-producing hybridoma can be prepared by immunizing a human antibody-producing animal (e.g., a mouse) with human CAPRIN-1 and then fusing splenocytes excised from the immunized animal to myeloma cells. Alternatively, DNAs encoding a light chain or heavy chain variable region and a constant region from a human antibody are prepared as necessary using gene recombination techniques or a DNA synthesizer.

In the case of humanized antibody, DNA is prepared by substituting a CDR coding sequence in DNA encoding a variable region of light chain or heavy chain derived from a human antibody, with a CDR coding sequence corresponding thereto of an antibody derived from a non-human animal (e.g., a mouse, a rat, or a chicken) and then ligating the DNA thus obtained to DNA encoding a constant region of light chain or heavy chain derived from a human antibody. Thus, DNA encoding humanized antibody can be prepared.

In the case of chimeric antibody, DNA encoding a chimeric antibody can be prepared by ligating DNA encoding a light chain or heavy chain variable region of an antibody from a non-human animal (e.g., a mouse, a rat, and a chicken) to DNA encoding a light chain or heavy chain constant region from a human antibody.

In the case of single chain antibody, this antibody is an antibody prepared by linearly ligating a heavy chain variable region to a light chain variable region via a linker. Thus, DNA encoding a single chain antibody can be prepared by binding DNA encoding a heavy chain variable region, DNA encoding a linker, and DNA encoding a light chain variable region. Herein, a heavy chain variable region and a light chain variable region are both from a human antibody, or, only CDRs are substituted with CDRs of an antibody from a non-human animal (e.g., a mouse, a rat, and a chicken) although the other regions are from a human antibody. Also, a linker comprises 12 to 19 amino acids, such as $(G_4S)_3$ of 15 amino acids (G. -B. Kim et al., Protein Engineering Design and Selection 2007, 20 (9): 425-432).

In the case of bispecific antibody (diabody), this antibody is capable of specifically binding to two different epitopes. For example, DNA encoding a bispecific antibody can be prepared by linking DNA encoding a heavy chain variable region A, DNA encoding a light chain variable region B, DNA encoding a heavy chain variable region B, and DNA encoding a light chain variable region A in this order (here, DNA encoding a light chain variable region B is bound to DNA encoding a heavy chain variable region B via DNA encoding the above linker). Here, a heavy chain variable region and a light chain variable region are both from a human antibody, or, only CDRs are substituted with CDRs of an antibody from a non-human animal (e.g., a mouse, a rat, or a chicken) although the other regions are from a human antibody.

The above-prepared recombinant DNA is incorporated into one or a plurality of appropriate vectors, they are introduced into host cells (e.g., mammalian cells, yeast cells, or insect cells), and then (co)expression is caused, so that a recombinant antibody can be prepared (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS; J. W. Goding., Monoclonal Antibodies: principles and practice., 1993 ACADEMIC PRESS).

Examples of the antibody of the present invention prepared by the above method include the following antibody (a) or (b):
(a) an antibody (e.g., the antibody composed of the heavy chain variable region of SEQ ID NO: 43 and the light chain variable region of SEQ ID NO: 47) comprising a heavy chain variable region comprising SEQ ID NOS: 40, 41, and 42 and a light chain variable region comprising SEQ ID NOS: 44, 45, and 46; and
(b) an antibody (e.g., the antibody composed of the heavy chain variable region of SEQ ID NO: 43 and the light chain variable region of SEQ ID NO: 53) comprising a heavy chain variable region comprising SEQ ID NOS: 40, 41, and 42 and a light chain variable region comprising SEQ ID NOS: 50, 51, and 52.

The amino acid sequences represented by SEQ ID NOS: 40, 41, and 42 are CDR1, CDR2, and CDR3 of a chicken antibody heavy chain variable region. Also, the amino acid sequences represented by SEQ ID NOS: 44, 45, and 46, and the amino acid sequences represented by SEQ ID NOS: 50, 51, and 52 are CDR1, CDR2, and CDR3 of a chicken antibody light chain variable region, respectively.

Also, the humanized antibody, the chimeric antibody, the single chain antibody, or the bispecific antibody of the present invention is the following antibody (exemplified as "antibody (a)"), for example:
(i) an antibody wherein the heavy chain variable region comprises the amino acid sequences of SEQ ID NOS: 40, 41, and 42 and the amino acid sequences of framework regions from a human antibody, and, a light chain variable region comprises the amino acid sequences of SEQ ID NOS: 44, 45, and 46 and the amino acid sequences of framework regions from a human antibody (e.g., the antibody wherein the heavy chain variable region comprises the amino acid sequence of SEQ ID NO: 43, and, the light chain variable region comprises the amino acid sequence of SEQ ID NO: 47).
(ii) an antibody wherein a heavy chain variable region comprises the amino acid sequences of SEQ ID NOS: 40, 41, and 42 and the amino acid sequences of framework regions from a human antibody, and, a heavy chain constant region comprises an amino acid sequence from a human antibody, and, a light chain variable region comprises the amino acid sequences of SEQ ID NOS: 44, 45, and 46 and the amino acid sequences of framework regions from a human antibody, and a light chain constant region comprises an amino acid sequence from a human antibody (e.g., the antibody wherein a heavy chain variable region comprises the amino acid sequence of SEQ ID NO: 43, and, a heavy chain constant region comprises an amino acid sequence from a human antibody, as well as, a light chain variable region comprises the amino acid sequence of SEQ ID NO: 47, and, a light chain constant region comprises an amino acid sequence from a human antibody).

In addition, the sequences of human antibody heavy chain and light chain constant regions and variable regions can be obtained from NCBI (e.g., U.S.A.: GenBank, UniGene), for example. For example, the sequence of Accession No. J00228 can be referred to for a human IgG1 heavy chain constant region, the sequence of Accession No. J00230 can be referred to for a human IgG2 heavy chain constant region, the sequence of Accession No. X03604 can be referred to for a human IgG3 heavy chain constant region, the sequence of Accession No K01316 can be referred to for a human IgG4 heavy chain constant region, the sequences of Accession Nos. V00557, X64135, X64133, and the like can be referred to for human light chain κ constant regions, and the sequences of Accession Nos. X64132, X64134, and the like can be referred to for human light chain λ constant regions.

The above antibodies preferably have cellular cytotoxic activity and thus can exhibit anti-tumor effects.

Also, the specific sequences of heavy chain and light chain variable regions or CDRs in the above antibodies are given simply for illustrative purposes, and thus are clearly not limited to such specific sequences. A hybridoma capable of producing another human antibody or non-human animal antibody (e.g., a mouse antibody) against human CAPRIN-1 is prepared, a monoclonal antibody that is produced by the hybridoma is collected, and then whether or not it is a target antibody is determined by immunological binding property with human CAPRIN-1 and cellular cytotoxic activity as indicators. After identification of a hybridoma producing the target monoclonal antibody in this manner, DNA encoding heavy chain and light chain variable regions of the target antibody is prepared from the hybridoma as described above, sequencing is carried out, and then the DNA is used for preparation of another antibody.

Furthermore, the above antibody of the present invention, the sequence of the above antibodies (a) and (b), particularly the sequence of the framework region and/or the sequence of the constant region of each of the antibodies may have a substitution, a deletion, or an addition of one or several (preferably, 1 or 2) amino acids, as long as it has specificity for specific recognition of CAPRIN-1. Here the term "several" refers to 2 to 5, and preferably 2 or 3.

The present invention further provides DNA encoding the above antibody of the present invention, or, DNA encoding the above antibody heavy chain or light chain, or, DNA encoding the above antibody heavy chain or light chain variable region. Examples of such DNA include, in the case of antibody (a), DNA encoding a heavy chain variable region comprising the nucleotide sequences encoding the amino acid sequences of SEQ ID NOS: 40, 41, and 42 and DNA encoding a light chain variable region comprising the nucleotide sequences encoding the amino acid sequences of SEQ ID NOS: 44, 45, and 46.

Complementarity determining regions (CDRs) encoded by the sequences of DNA are regions for determining the specificity of an antibody. Thus, sequences encoding regions in an antibody other than CDRs (specifically, a constant region and a framework region) may be from other antibodies. Here, examples of such "other antibodies" include antibodies from non-human organisms, and are preferably from a human in view of reduction of side effects. Thus, in the case of the above DNA, regions encoding each framework region and each contact region of heavy chains and light chains preferably comprise nucleotide sequences encoding corresponding amino acid sequences from a human antibody.

Further alternative examples of DNA encoding the antibody of the present invention include, in the case of antibody (a), DNA encoding a heavy chain variable region comprising the nucleotide sequence encoding the amino acid sequence of SEQ ID NO: 43 and DNA encoding a light chain variable region comprising the nucleotide sequence encoding the amino acid sequence of SEQ ID NO: 47. Here, an example of the nucleotide sequence encoding the amino acid sequence of SEQ ID NO: 43 is the nucleotide sequence of SEQ ID NO: 57. Also, an example of the nucleotide sequence encoding the amino acid sequence of SEQ ID NO: 47 is the nucleotide sequence of SEQ ID NO: 58. In these DNAs, regions encoding each constant region of heavy chains and light chains preferably comprise nucleotide sequences encoding the corresponding amino acid sequences from a human antibody.

The DNA of the present invention can be obtained by the above methods or the following method, for example. First, total RNA is prepared from a hybridoma relating to the antibody of the present invention using a commercially available RNA extraction kit, and then cDNA is synthesized with reverse transcriptase using random primers, and the like. Subsequently, cDNA encoding an antibody is amplified by a PCR method using as primers the oligonucleotides of sequences conserved in each variable region of known mouse antibody heavy chain and light chain genes. The sequence encoding a constant region can be obtained by amplifying a known sequence by a PCR method. The nucleotide sequence of DNA can be determined by a conventional method such as insertion of it into a plasmid or a phage for sequencing.

An anti-CAPRIN-1 antibody to be used in the present invention is considered to exhibit the anti-tumor effects against CAPRIN-1-expressing cancer cells due to antibody-dependent cellular cytotoxicity (ADCC) of effector cells against CAPRIN-1-expressing cells, or the complement-dependent cytotoxicity (CDC) against CAPRIN-1-expressing cells.

Therefore, the activity of an anti-CAPRIN-1 antibody to be used in the present invention can be evaluated by, as specifically described in Examples below, measuring ex vivo the above ADCC activity or CDC activity against CAPRIN-1-expressing cancer cells.

An anti-CAPRIN-1 antibody to be used in the present invention binds to a CAPRIN-1 protein on a cancer cell and exhibits anti-tumor effects due to the above activity, and thus it is useful for treating or preventing cancer. Specifically, the present invention provides a pharmaceutical composition for treating and/or preventing cancer, which comprises an anti-CAPRIN-1 antibody as an active ingredient. When the anti-CAPRIN-1 antibody is used for administration thereof to a human body (antibody therapy), it is preferably human antibody or humanized antibody in order to decrease immunogenicity.

In addition, the higher the binding affinity between an anti-CAPRIN-1 antibody and a CAPRIN-1 protein on the cancer cell surfaces, the stronger the anti-tumor activity of the anti-CAPRIN-1 antibody that can be obtained. Therefore, when an anti-CAPRIN-1 antibody having high binding affinity with a CAPRIN-1 protein can be acquired, stronger anti-tumor effects can be expected and such antibody's application as a pharmaceutical composition for the purpose of cancer treatment and/or prevention becomes possible. Such high binding affinity is desirably as follows. As described above, binding constant (affinity constant) Ka ($k_{on}/k_{off}$) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or, at least $10^{13}$ $M^{-1}$.

<Binding to Antigen-Expressing Cell>

The capacity of an antibody to bind to CAPRIN-1 can be specified by binding assay using ELISA, a Western blot method, immuno-fluorescence and flow cytometric analysis, or the like as described in Examples.

<Immunohistochemical Staining>

An antibody that recognizes CAPRIN-1 can be tested for reactivity to CAPRIN-1 by a method for immunohistochemistry known by persons skilled in the art using paraformaldehyde- or acetone-fixed frozen sections or paraformaldehyde-fixed paraffin-embedded tissue sections, which is prepared from tissue samples obtained from a patient during surgery, or tissue samples obtained from an animal having heterotransplant tissue inoculated with a cell line expressing CAPRIN-1, naturally or after transfection.

An antibody reactive to CAPRIN-1 can be stained by various methods for immunohistochemical staining. For example, a horseradish peroxidase-conjugated goat anti-mouse antibody or goat anti-chicken antibody is caused to undergo reaction, a target antibody can be visualized.

<Pharmaceutical Composition>

The present invention further provides a pharmaceutical composition for treating and/or preventing cancer, which is characterized by containing the above antibody or a fragment thereof as an active ingredient that has immunological reactivity with partial polypeptides of CAPRIN-1 represented by even-numbered SEQ ID NOS: 2 to 30, wherein the polypeptide has the amino acid sequence represented by SEQ ID NO: 37, or an amino acid sequence having 80% or more sequence identity with the amino acid sequence of SEQ ID NO: 37.

A target of the pharmaceutical composition for treating and/or preventing cancer of the present invention is not particularly limited, as long as it is cancer (cell) expressing a CAPRIN-1 gene.

The term "tumor" and "cancer" as used herein refers to malignant neoplasm and is used interchangeably.

Cancer to be subjected to the present invention is cancer expressing genes encoding CAPRIN-1 proteins having amino acid sequences of even-numbered SEQ ID NOS: 2 to 30. Examples of such cancer include preferably breast cancer, brain tumor, leukemia, lung cancer, lymphoma, mastocytoma, renal cancer, uterine cervix cancer, bladder cancer, esophageal cancer, gastric cancer, and colorectal cancer.

Examples of such specific cancer include, but are not limited to, breast adenocarcinoma, composite type breast adenocarcinoma, mammary gland malignant mixed tumor, intraductal papillary adenocarcinoma, lung adenocarcinoma, squamous cell carcinoma, small cell carcinoma, large cell carcinoma, glioma that is neural epithelial tissue tumor, ependymoma, neurocytoma, fetal neuroectodermal tumor, schwannoma, neurofibroma, meningioma, chronic lymphocytic leukemia, lymphoma, gastrointestinal lymphoma, digestive lymphoma, small-cell to medium-cell lymphoma, cancer of cecum, ascending colon cancer, descending colon cancer, transverse colon cancer, sigmoid colon cancer, and rectal cancer.

Moreover, preferable subjects are mammals including primates, pet animals, domestic animals, animals for race, and the like and are particularly preferably humans, dogs, and cats.

When an antibody to be used in the present invention is used as a pharmaceutical composition, it can be formulated by a method known by persons skilled in the art. For example, the antibody can be used parenterally in the form of an injection preparation such as an aseptic solution or a suspension prepared with water or a pharmacologically acceptable solution other than water. For example, it can be formulated by mixing in a unit dosage form required by generally accepted pharmaceutical practice in appropriate combination with a pharmacologically acceptable carrier or medium, specifically, sterile water or saline, vegetable oil, an emulsifier, a suspension, a surfactant, a stabilizer, a flavoring compound, an excipient, a vehicle, an antiseptic, a binder, and the like. The amounts of active ingredients in these preparations are determined so that an appropriate dose within the indicated range can be obtained.

An aseptic composition for injection can be prescribed according to general pharmaceutical practice using a vehicle such as distilled water for injection.

Examples of an aqueous solution for injection include saline, an isotonic solution containing dextrose or other adjuvants, such as D-sorbitol, D-mannose, D-mannitol, and sodium chloride. These examples may be used in combination with an appropriate solubilizing agent such as alcohol, specifically ethanol and polyalcohol (e.g., propylene glycol and polyethylene glycol), and nonionic surfactant (e.g., polysorbate 80™ and HCO-60).

Examples of the oil include sesame oil and soybean oil, which can be used in combination with a solubilizing agent such as benzyl benzoate or benzyl alcohol. Also, a buffering agent such as phosphate buffer or sodium acetate buffer, a soothing agent such as procaine hydrochloride, a stabilizer such as benzyl alcohol or phenol, and an antioxidant may be combined therewith. An appropriate amplus is generally filled with the thus prepared injection solution.

Administration is peroral or pereneteral administration and is preferably pereneteral administration. Specific examples of the route of administration include injection, transnasal administration, pulmonary administration, and transdermal administration. Examples of injection include intravenous injection, intramuscular injection, intraperitoneal injection, and subcutaneous injection, so that systemic or local administration is possible.

Also, administration methods can be appropriately selected depending on a patient's age, body weight, gender, symptoms, and the like. The dosage per administration of a pharmaceutical composition containing an antibody or a polynucleotide encoding the antibody can be selected from the range between 0.0001 mg and 1000 mg per kg of body weight, for example. Alternatively, for example, dosage can be selected from the range between 0.001 mg/body and 100000 mg/body per patient. However, the dosage range is not always limited to these numerical values. The dosage and administration method are varied depending on a patient's body weight, age, gender, symptoms, and the like, but can be appropriately selected by persons skilled in the art.

The above pharmaceutical composition containing the antibody or a fragment thereof of the present invention is administered to a subject, so that cancer, preferably, breast cancer, brain tumor, leukemia, lung cancer, lymphoma, mastocytoma, renal cancer, uterine cervix cancer, bladder cancer, esophageal cancer, gastric cancer, and colorectal cancer can be treated and/or prevented.

The present invention further encompasses a method for treating and/or preventing cancer, comprising administering to a subject the pharmaceutical composition of the present invention in combination with the above exemplified antitumor agent or pharmaceutical composition containing such antitumor agent. The antibody or a fragment thereof of the present invention and an antitumor agent may be administered simultaneously or separately to a subject. They can be separately administered regardless of the order of administration. The administration intervals, dosage, the route of administration, and the frequency of administration can be appropriately selected by a specialist. Examples of the other pharmaceutical formulation to be administered simultaneously include pharmaceutical compositions obtained by mixing the antibody or a fragment thereof of the present invention with an antitumor agent in a pharmacologically acceptable carrier (or a medium) followed by formulation. Furthermore, about either the above pharmaceutical composition containing an antitumor agent and formulation, explanations concerning prescription, formulation, the route of administration, dose, cancer, and the like for administering a pharmaceutical composition containing the antibody of the present invention and formulation are applicable. Therefore, the present invention also provides a pharmaceutical combination for treating and/or preventing cancer, comprising the pharmaceutical composition of the present invention, and the above exemplified pharmaceutical composition containing an antitumor agent. Also, the present invention provides a pharmaceutical composition for treating and/or preventing cancer, comprising the antibody or a fragment thereof of the present invention and an antitumor agent together with a pharmacologically acceptable carrier.

<Polypeptide and DNA>

The present invention further provides the following polypeptides and DNAs relating to the above antibodies (a) and (b).

(i) A polypeptide pharmaceutical combinationing the amino acid sequence of SEQ ID NO: 43, and DNA encoding the polypeptide.

(ii) A polypeptide comprising the amino acid sequences of SEQ ID NO: 47 and 53, and DNA encoding the polypeptide.

(iii) A heavy chain CDR polypeptide selected from the group consisting of the amino acid sequences represented by SEQ ID NOS: 40, 41, and 42, and DNA encoding the polypeptide.

(iv) A light chain CDR polypeptide selected from the group consisting of the amino acid sequences represented by SEQ ID NOS: 44, 45, and 46, and SEQ ID NOS: 50, 51, and 52, and DNA encoding the polypeptide.

These polypeptides and DNAs can be prepared using recombinant DNA techniques as described above.

SUMMARY OF THE PRESENT INVENTION

The above-explained present invention is as summarized as follows.

(1) A pharmaceutical composition for treating and/or preventing a cancer, comprising an antibody or a fragment thereof as an active ingredient that has immunological reactivity with a partial polypeptide of CAPRIN-1, wherein CAPRIN-1 is represented by any of the even-numbered sequences of SEQ ID NOS: 2 to 30, and wherein the partial polypeptide comprises the amino acid sequence represented by SEQ ID NO: 37 or an amino acid sequence having 80% or more sequence identity with the amino acid sequence of SEQ ID NO: 37.

(2) The pharmaceutical composition according to (1) above, wherein the cancer is breast cancer, brain tumor, leukemia, lymphoma, lung cancer, mastocytoma, renal cancer, uterine cervix cancer, bladder cancer, esophageal cancer, gastric cancer, or colorectal cancer.

(3) The pharmaceutical composition according to (1) or (2) above, wherein the antibody is a monoclonal antibody or a polyclonal antibody.

(4) The pharmaceutical composition according to any one of (1) to (3) above, wherein the antibody is a human antibody, humanized antibody, chimeric antibody, single chain antibody, or a bispecific antibody.

(5) An antibody having immunological reactivity with a polypeptide that comprise the amino acid sequence represented by SEQ ID NO: 37 or an amino acid sequence having 80% or more sequence identity with the amino acid sequence of SEQ ID NO: 37.

(6) The antibody according to (5) above, which has a cytotoxic activity against a cancer cell expressing a CAPRIN-1 protein.

(7) An antibody, which comprises a heavy chain variable region comprising SEQ ID NOS: 40, 41, and 42 and a light chain variable region comprising SEQ ID NOS: 44, 45, and 46, and has immunological reactivity with a CAPRIN-1 protein.

(8) An antibody, which comprises a heavy chain variable region comprising SEQ ID NOS: 40, 41, and 42 and a light chain variable region comprising SEQ ID NOS: 50, 51, and 52, and has immunological reactivity with a CAPRIN-1 protein.

(9) The antibody according to any one of (5) to (8) above, which is human antibody, humanized antibody, chimeric antibody, single chain antibody, or bispecific antibody.

(10) A pharmaceutical composition for treating and/or preventing a cancer, comprising the antibody or a fragment thereof of any one of (5) to (9) above as an active ingredient.

(11) The pharmaceutical composition according to (10) above, wherein the cancer is breast cancer, brain tumor, leukemia, lymphoma, lung cancer, mastocytoma, renal cancer, uterine cervix cancer, bladder cancer, esophageal cancer, gastric cancer, or colorectal cancer.

(12) A pharmaceutical combination for treating and/or preventing a cancer, comprising the pharmaceutical composition of any one of (1) to (4) above or the pharmaceutical composition of (10) or (11) above, and a pharmaceutical composition containing an antitumor agent.

(13) A method for treating and/or preventing a cancer, comprising administering to a subject the antibody or a fragment thereof of any one of (5) to (9) above or the pharmaceutical composition according to (10) or (11) above.

(14) A method for treating and/or preventing a cancer, comprising using pharmaceutical compositions of the pharmaceutical combination of (12) above in combination in a subject.

EXAMPLES

The present invention is described more specifically based on Examples, but the scope of the present invention is not limited by these specific examples.

Example 1

Identification of Novel Cancer Antigen Protein by SEREX Method (1) Preparation of cDNA Library Total RNA was extracted from a testis tissue of a healthy dog by an acid guanidium-phenol-chloroform method. PolyA RNA was purified according to protocols included with an Oligotex-dT30 mRNA purification Kit (Takara Shuzo Co., Ltd.) using the kit.

A dog testis cDNA phage library was synthesized using the thus obtained mRNA (5 μg). For preparation of the cDNA phage library, a cDNA synthesis kit, a ZAP-cDNA synthesis kit, and a ZAP-cDNA gigapack III gold cloning kit (STRATAGENE) were used and the library was prepared according to protocols included with the kit. The size of the thus prepared cDNA phage library was 7.73×10$^5$ pfu/ml.

(2) Screening of cDNA Library Using Serum

Immuno screening was carried out using the above-prepared dog testis cDNA phage library. Specifically, host *Escherichia coli* (XL1-Blue MRF') was infected with the phage so that 2210 clones were present on a φ90×15 mm NZY agarose plate. Cells were cultured at 42° C. for 3 to 4 hours, so as to cause plaque formation. The plate was covered with a nitrocellulose membrane (Hybond C Extra: GE Healthcare Bio-Science) impregnated with IPTG (isopropyl-β-D-thiogalactoside) at 37° C. for 4 hours. Proteins were induced, expressed, and then transferred to the membrane. Subsequently, the membrane was recovered, immersed, and shaken in TBS (10 mM Tris-HCl, 150 mM NaCl pH 7.5) containing 0.5% powdered skim milk at 4° C. overnight, so that nonspecific reaction was suppressed. The filter was caused to react with 500-fold diluted sera of dogs with cancer at room temperature for 2 to 3 hours.

As the above sera from dogs with cancer, sera collected from dogs with breast cancer were used. The sera were stored at −80° C. and then subjected to pretreatment immediately before use. Pretreatment for sera was performed by the following method. Specifically, host *Escherichia coli* (XL1-Blure MRF') was infected with λ ZAP Express phage into which no foreign gene had been inserted, and then cultured on NZY plate medium at 37° C. overnight. Subsequently, a 0.2 M NaHCO$_3$ buffer (pH 8.3) containing 0.5 M NaCl was added to the plate and then the plate was left to stand at 4° C. for 15 hours. The supernatants were collected as *Escherichia coli*/phage extracts. Next, the collected *Escherichia coli*/phage extract was passed through a NHS-column (GE Healthcare Bio-Science), so as to immobilize the *Escherichia coli* phage-derived protein. The serum of a dog with cancer was passed through the column to which the protein had been immobilized for reaction, thereby removing *Escherichia coli* and antibodies adsorbed to the phage from the serum. Each serum fraction that had passed through the column was diluted 500-fold with TBS containing 0.5% powdered skim milk, and the resultant was used as an immunoscreening material.

A membrane, to which the thus treated serum and the fusion protein had been blotted, was washed 4 times with TBS-T (0.05% Tween20/TBS). The membrane was reacted with goat anti-dog IgG (Goat anti Dog IgG-h+l HRP conjugated: BETHYL Laboratories) diluted 5000-fold as a secondary antibody with TBS containing 0.5% powdered skim milk at room temperature for 1 hour. Detection was carried out by enzyme color reaction using an NBT/BCIP reaction solution (Roche). Colonies corresponding to the color reaction positive site were collected from the φ90×15 mm NZY agarose plate, and then dissolved in 500 µl of SM buffer (100 mM NaCl, 10 mM MgClSO$_4$, 50 mM Tris-HCl, 0.01% gelatin, pH 7.5). Until unification of color reaction positive colonies, secondary screening and tertiary screening were repeated by a method similar to the above. Thus, 30940 phage clones that had reacted with serum IgG were screened so that 5 positive clones were isolated.

(3) Homology Search for Isolated Antigen Gene

A procedure for conversion of phage vectors to plasmid vectors was performed for the 5 positive clones isolated by the above method for the purpose of subjecting the clones to nucleotide sequence analysis. Specifically, 200 µl of a solution of host Escherichia coli (XL1-Blue MRF') prepared to give an absorbance OD$_{600}$ of 1.0, 250 µl of a purified phage solution, and 1 µl of ExAssist helper phage (STRATAGENE) were mixed and allowed to react at 37° C. for 15 minutes. After that, 3 ml of LB medium was added, cells were cultured at 37° C. for 2.5 to 3 hours, and then the resultant was immediately put in water bath at 70° C. for incubation for 20 minutes. Centrifugation was carried out at 4° C., 1000×g for 15 minutes, and then the supernatant was collected as a phagemid solution. Subsequently, 200 µl of a solution prepared from phagemid host Escherichia coli SOLR to give an absorbance OD$_{600}$ of 1.0 and 10 µl of the purified phage solution were mixed, followed by 15 minutes of reaction at 37° C. 50 µl of the resultant was plated on LB agar medium containing ampicillin (at final concentration of 50 µg/ml) and then cultured overnight at 37° C. A single colony of transformed SOLR was collected and then cultured on LB medium containing ampicillin (at final concentration of 50 µg/ml) at 37° C. After culture, plasmid DNA carrying an insert of interest was purified using a QIAGEN plasmid Miniprep Kit (QIAGEN).

The purified plasmid was subjected to the analysis of the entire sequence of the insert by the primer walking method using the T3 primer of SEQ ID NO: 31 and the T7 primer of SEQ ID NO: 32. The gene sequences of SEQ ID NOS: 5, 7, 9, 11, and 13 were obtained by the sequence analysis. With the use of the nucleotide sequences of the genes and the amino acid sequences thereof (SEQ ID NOS: 6, 8, 10, 12, and 14), homology search program BLAST search (www.ncbi.nlm.nih.gov/BLAST/) was conducted for searching homology with known genes. As a result, it was revealed that all the five obtained genes were genes encoding CAPRIN-1. The sequence identities among the five genes were 100% at the nucleotide sequence level and 99% at the amino acid sequence level in the regions to be translated into proteins. The sequence identities of these genes and the human homologue-encoding gene were 94% at the nucleotide sequence level and 98% at the amino acid sequence level in the regions to be translated into proteins. The nucleotide sequences of the human homologues are represented by SEQ ID NOS: 1 and 3 and the amino acid sequences of the same are represented by SEQ ID NOS: 2 and 4. Also, the sequence identities of the obtained dog genes and the cattle homologue-encoding gene were 94% at the nucleotide sequence level and 97% at the amino acid sequence level in the regions to be translated into proteins. The nucleotide sequence of the cattle homologue is represented by SEQ ID NO: 15 and the amino acid sequence of the same is represented by SEQ ID NO: 16. In addition, the sequence identities of the human homologue-encoding genes and the cattle homologue-encoding gene were 94% at the nucleotide sequence level and 93% to 97% at the amino acid sequence level in the regions to be translated into proteins. Also, the sequence identities of the obtained dog genes and the horse homologue-encoding gene were 93% at the nucleotide sequence level and 97% at the amino acid sequence level in the regions to be translated into proteins. The nucleotide sequence of the horse homologue is represented by SEQ ID NO: 17 and the amino acid sequence of the same is represented by SEQ ID NO: 18. In addition, the sequence identities of the human homologue-encoding genes and the horse homologue-encoding gene were 93% at the nucleotide sequence level and 96% at the amino acid sequence level in the regions to be translated into proteins. Also, the sequence identities of the obtained dog genes and the mouse homologue-encoding genes were 87% to 89% at the nucleotide sequence level and 95% to 97% at the amino acid sequence level in the regions to be translated into proteins. The nucleotide sequences of the mouse homologues are represented by SEQ ID NOS: 19, 21, 23, 25, and 27 and the amino acid sequences of the same are represented by SEQ ID NOS: 20, 22, 24, 26, and 28. In addition, the sequence identities of the human homologue-encoding genes and the mouse homologue-encoding genes were 89% to 91% at the nucleotide sequence level and were 95% to 96% at the amino acid sequence level in the regions to be translated into proteins. Also, the sequence identities of the obtained dog genes and the chicken homologue-encoding gene were 82% at the nucleotide sequence level and 87% at the amino acid sequence level in the regions to be translated into proteins. The nucleotide sequence of the chicken homolog is represented by SEQ ID NO: 29 and the amino acid sequence of the same is represented by SEQ ID NO: 30. In addition, the sequence identities of the human homologue-encoding genes and the chicken homologue-encoding gene were 81% to 82% at the nucleotide sequence level and 86% at the amino acid sequence level in the regions to be translated into proteins.

(4) Gene Expression Analysis in Each Tissue

The expression of genes obtained by the above method was examined in dog and human normal tissues and various cell lines by an RT-PCR method. Reverse transcription reaction was performed as follows. Specifically, total RNA was extracted from 50 mg to 100 mg of the tissue or 5 to 10×10$^6$ cells of the cell line using a TRIZOL reagent (Invitrogen) according to the accompanying protocols. cDNA was synthesized with the total RNA using a Superscript First-Strand Synthesis System for RT-PCR (Invitrogen) according to the accompanying protocols. PCR was performed as follows using primers of SEQ ID NOS: 33 and 34 specific to the obtained genes. Specifically, reagents and an accompanying buffer were added to 0.25 µl of the sample prepared by the reverse transcription reaction to a total volume of 25 µl, so that the resultant contained the above primers of 2 µM each, dNTPs of 0.2 mM each, and 0.65 U ExTaq polymerase (Takara Shuzo Co., Ltd.). PCR was carried out by repeating a cycle of 94° C. for 30 seconds, 60° C. for 30 seconds, and 72° C. for 30 seconds 30 times using a Thermal Cycler (BIO RAD). The above gene-specific primers are capable of amplifying the region ranging from nucleotides 206 to 632 in the nucleotide sequence of SEQ ID NO: 5 (dog CAPRIN-1 gene) and the region ranging from nucleotides 698 to 1124 in the nucleotide sequence of SEQ ID NO: 1 (human CAPRIN-1 gene). As a control for comparison, GAPDH-specific primers of SEQ ID NOS: 35 and 36 were also used concurrently. As a result, as shown in FIG. 1, strong expression was observed in testis among normal dog tissues, while expression was observed in dog breast cancer and adenocarcinoma tissues. Moreover, the observation of the expression of the human homologues from the obtained genes was also carried out. As a result, similarly to the case of the dog CAPRIN-1 gene, expression could be observed in only testis among normal tissues. However, in the case of cancer cells, expression was detected in many types of cancer cell lines, including breast cancer, brain tumor, leukemia, lung cancer, and esophageal cancer cell lines. Expression was observed particularly in many breast cancer cell lines. It was confirmed by the results that the expression of CAPRIN-1 is not observed in normal tissues other than testis, while CAPRIN-1 was expressed in many cancer cells and particularly in breast cancer cell lines.

In FIG. 1, reference number 1 on each vertical axis indicates the expression patterns of genes identified above and reference number 2 indicates the expression patterns of the GAPDH gene as a control.

(5) Immunohistochemical Staining (5)-1 CAPRIN-1 Expression in Mouse and Dog Normal Tissues Mice (Balb/c, female) and dogs (beagles, female) were exsanguinated under ether anesthesia and ketamine/isoflurane anesthesia. After laparotomy, each organ (stomach, liver, eyeball, thymus gland, muscle, bone marrow, uterus, small bowel, esophagus, heart, kidney, salivary gland, large bowel, mammary gland, brain, lung, skin, adrenal gland, ovary, pancreas, spleen, and bladder) was transferred to a 10-cm dish containing PBS. Each organ was cut open in PBS and then subjected to perfusion fixation overnight in 0.1 M phosphate buffer (pH 7.4) containing 4% paraformaldehyde (PFA). The perfusion solution was discarded, the tissue surface of each organ was rinsed with PBS, a PBS solution containing 10% sucrose was added to a 50-ml centrifuge tube, each tissue was added to the tube, and then the tube was shaken using a rotor at 4° C. for 2 hours. The solution was replaced by a PBS solution containing 20% sucrose, and then left to stand at 4° C. until the tissue sank. The solution was replaced by a PBS solution containing 30% sucrose and then left to stand at 4° C. until the tissue sank. The tissue was removed and then needed portions were excised with a surgical scalpel. Next, an OCT compound (Tissue Tek) was added to the tissue so that it was thoroughly applied to the tissue surface, and then the tissue was placed in a cryomold. The cryomold was placed on dry ice for quick freezing. Thereafter, the tissue was sliced to 10 µm to 20 µm using a cryostat (LEICA). Slices were air-dried on slide glasses using a hair dryer for 30 minutes, to prepare the sliced tissue mounted on a slide glass. Next, each sample was placed in a staining bottle filled with PBS-T (saline containing 0.05% Tween20) and then subjected to replacement with PBS-T being repeated three times every 5 minutes. Excess water around the sections was removed with Kimwipes, and then the sections were circled using a DAKOPEN (DAKO). As blocking solutions, an MOM mouse Ig blocking reagent (VECTASTAIN) and a PBS-T solution containing 10% FBS were overlaid on mouse tissue and dog tissue, respectively, and then left to stand in a moist chamber at room temperature for 1 hour. Next, a solution of the monoclonal antibody against CAPRIN-1 (monoclonal antibody #1) of 10 µg/ml adjusted with a blocking solution, which reacts with cancer cell surfaces and has the heavy chain variable region of SEQ ID NO: 43 and the light chain variable region of SEQ ID NO: 47, which had been prepared in Example 4, was placed on and then left to stand overnight in a moist chamber at 4° C. 10 minutes of washing with PBS-T was performed 3 times, and then an MOM biotin-labeled anti-IgG antibody (VECTASTAIN) diluted 250-fold with the blocking solution was placed and then left to stand at room temperature for 1 hour in a moist chamber. After ten (10) minutes of washing with PBS-T was performed 3 times, an avidin-biotin ABC reagent (VECTASTAIN) was placed on, and then the sample was left to stand in a moist chamber at room temperature for 5 minutes. After ten (10) minutes of washing with PBS-T was performed 3 times, a DAB coloring solution (DAB 10 mg+30% $H_2O_2$ 10 µl/0.05 M Tris-HCl (pH 7.6) 50 ml) was placed on, and then the sample was left to stand in a moist chamber at room temperature for 30 minutes. After rinsing with distilled water, a hematoxylin reagent (DAKO) was placed on, the sample was left to stand at room temperature for 1 minute, and then rinsed with distilled water. The slide glass was immersed in 70%, 80%, 90%, 95%, and then 100% ethanol solutions in such order for 1 minute each and then left to stand overnight in xylene. The slide glass was removed, sealed in Glycergel Mounting Medium (DAKO), and then observed. As a result, the expression of CAPRIN-1 was slightly observed within cells of each tissue of salivary gland, kidney, colon, and stomach, but the expression of the same was not observed on cell surfaces. Furthermore, no expression was observed in tissues from other organs. In addition, similar results were obtained in the case of using a monoclonal antibody against CAPRIN-1 (monoclonal antibody #2) having the heavy chain variable region of SEQ ID NO: 43 and the light chain variable region of SEQ ID NO: 53.

(5)-2 CAPRIN-1 Expression in Dog Breast Cancer Tissue

Frozen section slides were prepared by a method similar to the above using 108 frozen breast cancer tissue specimens of dogs pathologically diagnosed as having malignant breast cancer, and immunohistochemical staining was performed using the monoclonal antibody #1 prepared in Example 4. As a result, the expression of CAPRIN-1 was observed in 100 out of 108 specimens (92.5%) and CAPRIN-1 was strongly expressed on the surfaces of cancer cells with a particularly high grade of atypism. In addition, similar results were obtained when the monoclonal antibody #2 had been used.

(5)-3 CAPRIN-1 Expression in Human Breast Cancer Tissues

Immunohistochemical staining was performed using 188 breast cancer tissue specimens on a paraffin-embedded human breast cancer tissue array (BIOMAX). After 3 hours of treatment of the human breast cancer tissue array at 60° C., the array was placed in a staining bottle filled with xylene, followed by xylene replacement being repeated three times every 5 minutes. Next, a similar procedure was performed with ethanol and PBS-T instead of xylene. The human breast cancer tissue array was placed in a staining bottle filled with 10 mM citrate buffer (pH 6.0) containing 0.05% Tween20. After 5 minutes of treatment at 125° C., the array was left to stand at room temperature for 40 minutes or more. Excess water around the sections was removed with Kimwipes, the sections were circled with a DAKOPEN, and Peroxidase Block (DAKO) was added dropwise in appropriate amounts. After left to stand at room temperature for 5 minutes, the array was placed in a staining bottle filled with PBS-T, followed by PBS-T replacement being repeated three times every 5 minutes. As a blocking solution, a PBS-T solution containing 10% FBS was placed on the array, and then the array was left to stand in a moist chamber at room temperature for 1 hour. Next, a solution of the monoclonal antibody #1 of 10 µg/ml adjusted with a PBS-T solution containing 5% FBS, which reacts with cancer cell surfaces and had been prepared in Example 4, was placed on, and the array was left to stand overnight in a moist chamber at 4° C. After ten (10) minutes of washing with PBS-T was performed 3 times, Peroxidase Labeled Polymer Conjugated (DAKO) was added dropwise in appropriate amounts and then the array was left to stand in a moist chamber at room temperature for 30 minutes. After ten (10) minutes of washing with PBS-T was performed 3 times, a DAB coloring solution (DAKO) was placed on and then it was left to stand at room temperature for about 10 minutes. The coloring solution was discarded, 10 minutes of washing with PBS-T was performed 3 times, and then it was rinsed with distilled water. The array was immersed in 70%, 80%, 90%, 95%, and then 100% ethanol solutions in such order for 1 minute each, and then left to stand in xylene overnight. The slide glass was removed, sealed in Glycergel Mounting Medium (DAKO), and then observed. As a result, the strong expression of CAPRIN-1 was observed in 138 out of a total of 188 breast cancer tissue specimens (73%). In addition, similar results were obtained when the monoclonal antibody #2 had been used.

(5)-4 CAPRIN-1 Expression in Human Malignant Brain Tumor

Immunohistochemical staining was performed according to a method similar to that used in (5)-3 above with 247 malignant brain tumor tissue specimens on a paraffin-embedded human malignant brain tumor tissue array (BIOMAX), using the monoclonal antibody #1 prepared in Example 4. As a result, the strong expression of CAPRIN-1 was observed in 227 out of a total of 247 malignant brain tumor tissue specimens (92%). In addition, similar results were obtained when the monoclonal antibody #2 had been used.

(5)-5 CAPRIN-1 Expression in Human Breast Cancer Metastasized Lymph Node

Immunohistochemical staining was performed according to a method similar to that in (5)-3 above with 150 breast cancer metastasized lymph node tissue specimens on a paraffin-embedded human breast cancer metastasized lymph node tissue array (BIOMAX), using the monoclonal antibody #1 prepared in Example 4. As a result, the strong expression of CAPRIN-1 was observed in 136 out of a total of 150 breast cancer metastasized lymph node tissue specimens (90%). Specifically, it was revealed that CAPRIN-1 was strongly expressed also in cancer tissues that had metastasized from breast cancer. In addition, similar results were obtained when the monoclonal antibody #2 had been used.

(5)-6 CAPRIN-1 Expression in Various Human Cancer Tissues

Immunohistochemical staining was performed according to a method similar to the above with specimens on various paraffin-embedded human cancer tissue arrays (BIOMAX), using the monoclonal antibody #1 prepared in Example 4. As a result, the strong expression of CAPRIN-1 was observed in esophageal cancer, colon cancer, rectal cancer, lung cancer, renal cancer, bladder cancer, and uterine cervix cancer. In addition, similar results were obtained when the monoclonal antibody #2 had been used.

Example 2

Preparation of Novel Human Cancer Antigen Protein (1) Preparation of Recombinant Protein Based on the gene of SEQ ID NO: 1 obtained in Example 1, a recombinant protein from the human homologous gene was prepared by the following method. PCR was performed in a total volume of 50 µl with 1 µl of cDNA, two primers (SEQ ID NOS: 38 and 39 comprising Sac I and Xho I restriction enzyme cleavage sequences) of 0.4 µM each, 0.2 mM dNTP, and 1.25U PrimeSTAR HS polymerase (Takara Shuzo Co., Ltd.), prepared by adding the reagents and an accompanying buffer. The expression had been confirmed by an RT-PCR method for the cDNA used herein from among various tissue or cell-derived cDNAs prepared in Example 1. PCR was preformed by repeating a cycle of 98° C. for 10 seconds and 68° C. for 2.5 minutes 30 times using a Thermal Cycler (BIO RAD). The above two primers are capable of amplifying a region encoding the entire amino acid sequence of SEQ ID NO: 2. After PCR, the thus amplified DNA was subjected to electrophoresis on 1% agarose gel, and then an about 2.1 kbp DNA fragment was purified using a QIAquick Gel Extraction Kit (QIAGEN).

The thus purified DNA fragment was ligated to a cloning vector PCR-Blunt (Invitrogen). After transformation of *Escherichia coli* with it, plasmid was collected. It was verified by sequencing that the thus amplified gene fragment has the sequence of interest. The plasmid having a matched sequence with the sequence of interest was treated with Sac I and Xho I restriction enzymes and then purified with a QIAquick Gel Extraction Kit. The gene sequence of interest was inserted into an *Escherichia coli* expression vector pET30a (Novagen) treated with Sac I and Xho I restriction enzymes. A His-tag fused recombinant protein can be produced using the vector. The plasmid was transformed into *Escherichia coli* for recombinant expression, BL21(DE3), and then expression was induced with 1 mM IPTG, so that the protein of interest was expressed in *Escherichia coli*.

(2) Purification of Recombinant Protein

The above-obtained recombinant *Escherichia coli* expressing the gene of SEQ ID NO: 1 was cultured in LB medium containing 30 µg/ml kanamycin at 37° C. until absorbance at 600 nm reached around 0.7, isopropyl-β-D-1-thiogalactopyranoside was added at a final concentration of 1 mM, and then cells were cultured at 37° C. for 4 hours. Subsequently, centrifugation was performed at 4800 rpm for 10 minutes and then cells were collected. The resulting cell pellet was suspended in phosphate buffered saline and centrifuged at 4800 rpm for 10 minutes, and then cells were washed.

The cells were suspended in phosphate buffered saline and then disrupted by ultrasonication on ice. The resulting lysate of the ultrasonicated *Escherichia coli* was subjected to centrifugation at 6000 rpm for 20 minutes, and then the resulting supernatant was regarded as a soluble fraction and the precipitate was regarded as an insoluble fraction.

The soluble fraction was added to a nickel chelate column adjusted according to a conventional method (carrier: Chelating Sepharose™ Fast Flow (GE HealthCare); column capacity of 5 ml; and equilibration buffer: 50 mM hydrochloride buffer (pH 8.0)). Unadsorbed fractions were washed off with 50 mM hydrochloride buffer (pH 8.0) in an amount 10 times the column capacity and 20 mM phosphate buffer (pH 8.0) containing 20 mM imidazole. Immediately after washing, 6 beds were eluted with 20 mM phosphate buffer (pH 8.0) containing 100 mM imidazole. The elution of the protein of interest was confirmed by Coomassie staining on the elution fraction with 20 mM phosphate buffer (pH 8.0) containing 100 mM imidazole, and then the elution fraction was added to a strong anion exchange column (carrier: Q Sepharose™ Fast Flow (GE HealthCare); column capacity of 5 ml; and 20 mM phosphate buffer (pH 8.0) as an equilibration buffer). An unadsorbed fraction was washed off with 20 mM phosphate buffer (pH 7.0) in an amount 10 times the column capacity and 20 mM phosphate buffer (pH 7.0) containing 200 mM sodium chloride. Immediately after washing, 5 beds were eluted with 20 mM phosphate buffer (pH 7.0) containing 400 mM sodium chloride, and thus the purified fraction of the protein having the amino acid sequence represented by SEQ ID NO: 2 was obtained.

200 µl of each purified sample obtained by the above method was dispensed into 1 ml of reaction buffer (20 mM Tris-Hcl, 50 mM, NaCl, 2 mM $CaCl_2$, pH 7.4), followed by addition of 2 µl of enterokinase (Novagen). After that, the resultant was left to stand overnight at room temperature for reaction so that His-tag was cleaved off, and then purification was performed using an Enterokinase Cleavage Capture Kit (Novagen) according to the accompanying protocols. Next, 1.2 ml of the purified sample obtained by the above method was subjected to the buffer replacement with physiological phosphate buffer (Nissui Pharmaceutical Co., Ltd.) using an ultrafiltration NANOSEP 10K OMEGA (PALL). Further, sterile filtration was performed using HT Tuffryn Acrodisc 0.22 μm (PALL) and then the resultant was used for the following experiment.

Example 3

Preparation of Chicken Monoclonal Antibody Against CAPRIN-1

300 μg of the antigen protein (human CAPRIN-1) ( ) shown by SEQ ID NO: 2 prepared in Example 2 was mixed with an equivalent amount of Freund's complete adjuvant, and then this was used as an antigen solution per one chicken. The antigen solution was intraperitoneally administered to 7-week-old chickens, and then the administration was performed 7 times every 4 weeks, and thus immunization was completed. Each spleen was excised on day 4 after the final immunization, and sandwiched between two sterilized slide glasses and then crushed. The resultant was washed with PBS(–) (Nissui) and then centrifuged at 1500 rpm for 10 minutes to remove the supernatant. This procedure was repeated 3 times, so that splenocytes were obtained. The thus obtained splenocytes and chicken myeloma cells deficient in light chain were mixed at a ratio of 5:1. The used chicken myeloma cells had been established from a chicken by a transformation using an avian reticuloendotheliosis virus. A PEG solution prepared by mixing 200 μl of IMDM medium containing 10% FBS heated at 37° C. and 800 μl of PEG1500 (Boehringer) was added to the mixture, left to stand for 5 minutes for cell fusion, and then subjected to centrifugation at 1700 rpm for 5 minutes. After removal of the supernatant, cells were suspended in 300 ml of IMDM medium containing 10% FBS, supplemented with a HAT solution (Gibco) (2% equivalent) (HAT selective medium), and then the cell suspension was plated on thirty 96-well plates (Nunc) at 100 μl per well. Cells were cultured under conditions of 7 days, at 37° C., under 5% $CO_2$, so that hybridoma prepared by fusion of splenocytes and chicken myeloma cells were obtained.

Hybridomas were selected using as a marker the binding affinity of the antibody produced by the prepared hybridomas to the CAPRIN-1 protein. The CAPRIN-1 protein solution (1 μg/ml) prepared in Example 2 was added to a 96-well plate at 100 μl per well and then left to stand at 4° C. for 18 hours. Each well was washed 3 times with PBS-T, 400 μl of a 0.5% Bovine Serum Albumin (BSA) solution (Sigma) was added per well, and then the plate was left to stand at room temperature for 3 hours. The solution was removed, and then the wells were washed three times with 400 μl of PBS-T per well. The culture supernatant of the above-obtained hybridomas was added at 100 μl per well, and then left to stand at room temperature for 2 hours. After washing each well three times with PBS-T, an HRP-labeled anti-chicken IgY antibody (SIGMA) diluted 5000-fold with PBS was added at 100 μl per well and the resultant was then left to stand at room temperature for 1 hour. After washing the wells three times with PBS-T, 100 μl of a TMB substrate solution (Thermo) was added per well and then left to stand for 15 to 30 minutes for coloring reaction. After color development, 100 μl of 1N sulfuric acid was added per well to stop the reaction, and then absorbances at 450 nm and 595 nm were measured using an absorption spectrometer. As a result, several hybridomas producing antibodies with high absorbance values were selected.

The thus selected hybridomas were added to a 96-well plate at 0.5 cells per well and then cultured. After 1 week, hybridomas that had formed single colonies in wells were observed. These cells in the wells were further cultured, and then hybridomas were selected using as a marker the binding affinity of antibodies produced by the cloned hybridomas to the CAPRIN-1 protein. The CAPRIN-1 protein solution (1 μg/ml) prepared in Example 2 was added to a 96-well plate at 100 μl per well, and then left to stand at 4° C. for 18 hours. Each well was washed with PBS-T three times, 400 μl of a 0.5% BSA solution was added per well, and then the resultant was left to stand at room temperature for 3 hours. The solution was removed, and then the wells were washed three times with 400 μl of PBS-T per well. 100 μl of each culture supernatant of the above-obtained hybridomas was added per well, and then the plate was left to stand at room temperature for 2 hours. After washing each well three times with PBS-T, 100 μl of an HRP-labeled anti-chicken IgY antibody (SIGMA) diluted 5000-fold with PBS was added per well and then left to stand at room temperature for 1 hour. After washing the wells three times with PBS-T, 100 μl of a TMB substrate solution (Thermo) was added per well, and then left to stand for 15 to 30 minutes for coloring reaction. After color development, 100 μl of 1N sulfuric acid was added per well to stop the reaction and then absorbances at 450 nm and 595 nm were measured using an absorption spectrometer. As a result, several hybridoma cell lines producing monoclonal antibodies reactive to the CAPRIN-1 protein were obtained.

Next, of those monoclonal antibodies, antibodies reactive to the cell surfaces of breast cancer cells expressing CAPRIN-1 were selected. Specifically, $5 \times 10^5$ cells of the human breast cancer cell line MDA-MB-231V were subjected to centrifugation with a 1.5-ml microcentrifuge tube, and 100 μl of the culture supernatant of each of the above hybridomas was added to the tube, and then the tube was left to stand on ice for 1 hour. After washing with PBS, an FITC-labeled goat anti-chicken IgG (H+L) antibody (SouthernBiotech) diluted 30-fold with PBS containing 0.1% FBS was added, and then the resultant was left to stand on ice for 1 hour. After washing with PBS, fluorescence intensity was measured using a FACS caliber (Becton, Dickinson and Company). Meanwhile, procedures similar to the above were performed for medium for culturing hybridomas, so that a control sample was obtained. As a result, two monoclonal antibodies (monoclonal antibodies #1 and #2) that had exhibited fluorescence intensity stronger than that of the control, and that is, that reacted with the cell surfaces of CAPRIN-1-expressing breast cancer cells, were selected.

Example 4

Characterization of Selected Antibodies (1) Cloning of Anti-CAPRIN-1 Monoclonal Antibody Variable Region Gene mRNA was extracted from each hybridoma cell line producing either one of the two monoclonal antibodies selected in Example 3. An RT-PCR method using primers specific to the chicken FR1-derived sequence and the chicken FR4-derived sequence was performed therefor, and the gene of the heavy chain variable (VH) region and the gene of the light chain variable (VL) region of each antibody were obtained. For sequencing, these genes were cloned into a pCR2.1 vector (Invitrogen).

(1)-1 RT-PCR

After extraction of total RNA from 10⁶ cells of each hybridoma cell line using a High Pure RNA Isolation Kit (Roche), cDNA was synthesized using a PrimeScriptII 1st strand cDNA Synthesis Kit (Takara). These procedures were performed according to protocols attached to each kit.

The gene of the chicken antibody heavy chain variable region and the gene of the chicken antibody light chain variable region were amplified by a PCR method according to a conventional method using the thus synthesized cDNA as a template and KOD-Plus-DNA Polymerase (TOYOBO).

To obtain the gene of the VH region, a primer specific to the chicken heavy chain FR1 sequence and a primer specific to the chicken heavy chain FR4 sequence were used. Furthermore, to obtain the gene of the VL region, a primer specific to the chicken light chain FR1 sequence and a primer specific to the chicken light chain FR4 were used.

The thus obtained PCR products were each subjected to agarose gel electrophoresis, and DNA bands of the VH region and the VL region were excised. DNA fragments were purified using a QIAquick Gel purification kit (QIAGEN) according to the accompanying protocols. The purified DNA was cloned into a pCR2.1 vector using a TA cloning kit (Invitrogen). The ligated vector was transformed into DH5 competent cells (TOYOBO) according to a conventional method. 10 clones of each transformant were cultured overnight in medium (100 µg/ml ampicillin) at 37° C., and then plasmid DNA was purified using a Qiaspin Miniprep kit (QIAGEN).

(1)-2 Sequence Determination

The gene sequences of the VH region and the VL region in each plasmid obtained above were analyzed with an M13 forward primer (SEQ ID NO: 48) and an M13 reverse primer (SEQ ID NO: 49) on a fluorescence sequencer (DNA sequencer 3130XL; ABI), using a Big Dye Terminator Ver3.1 Cycle Sequencing Kit (ABI) according to the accompanying protocols. As a result, each gene sequence was determined. The sequences were identical among the 10 clones.

The thus obtained amino acid sequence of the monoclonal antibody heavy chain variable region is represented by SEQ ID NO: 43 and the thus obtained amino acid sequences of the light chain variable regions are represented by SEQ ID NO: 47 and SEQ ID NO: 53.

Specifically, it was revealed that the monoclonal antibody #1 comprises the heavy chain variable region of SEQ ID NO: 43 and the light chain variable region of SEQ ID NO: 47, wherein CDR1, CDR2, and CDR3 in the heavy chain variable region consist of the amino acid sequences of SEQ ID NOS: 40, 41, and 42, respectively, and the CDR1, CDR2, and CDR3 in the light chain variable region consist of the amino acid sequences of SEQ ID NOS: 44, 45, and 46, respectively. It was also revealed that monoclonal antibody #2 comprises the heavy chain variable region of SEQ ID NO: 43 and the light chain variable region of SEQ ID NO: 53, wherein CDR1, CDR2, and CDR3 in the heavy chain variable region consist of the amino acid sequences of SEQ ID NOS: 40, 41, and 42, respectively, and CDR1, CDR2, and CDR3 in the light chain variable region consist of the amino acid sequences of SEQ ID NOS: 50, 51, and 52, respectively.

(2) Preparation of Human-Chicken Chimeric Recombinant Antibody

An amplification fragment of the gene of the heavy chain variable region (SEQ ID NO: 43) of the chicken monoclonal antibodies #1 and #2 obtained in (1) above were treated at both ends with restriction enzymes and then purified. The resulting fragment was inserted into a pcDNA4/myc-His (Invitrogen) vector according to a conventional method, into which a human antibody-derived leader sequence comprising SEQ ID NO: 54 and a human IgG1 H-chain constant region comprising SEQ ID NO: 55 had already been inserted. Furthermore, an amplification fragment of the gene of the chicken monoclonal antibody #1 light chain variable region (SEQ ID NO: 47) were treated at both ends with restriction enzymes and then purified. The resulting fragment was inserted into a pcDNA3.1/myc-His (Invitrogen) vector according to a conventional method, into which a chicken antibody-derived leader sequence comprising SEQ ID NO: 54 and a human IgG1 L-chain constant region comprising SEQ ID NO: 56 had already been inserted. Similarly, An amplification fragment of the gene of the chicken monoclonal antibody #2 light chain variable region (SEQ ID NO: 53) were treated at both ends with restriction enzymes and then purified. The resulting fragment was inserted into a pcDNA3.1/myc-His vector according to a conventional method, into which the chicken antibody-derived leader sequence and the human IgG1 L-chain constant region had already been inserted.

Next, the above recombinant vector into which the heavy chain variable region (SEQ ID NO: 43) of the chicken monoclonal antibodies #1 and #2 had been inserted, and the above recombinant vector into which the chicken monoclonal antibody #1 light chain variable region (SEQ ID NO: 47) had been inserted, were introduced into CHO-K1 cells (obtained from RIKEN Cell Bank). Specifically, 2×10⁵ CHO-K1 cells cultured in 1 ml of Ham's F12 medium (Invitrogen) containing 10% FBS per well of a 12-well culture plate were washed with PBS(−). 1 ml of Ham's F12 medium containing 10% FBS was further added per well and then a mixture of 250 ng of each of the above vectors dissolved in 30 µl of OptiMEM (Invitrogen) and 30 µl of a Polyfect transfection reagent (QIAGEN) was added to each well. CHO-K1 cells into which the above recombinant vector had been introduced were cultured in Ham's F12 medium containing 10% FBS, supplemented with 200 µg/ml Zeocin (Invitrogen) and 200 µg/ml geneticin (Roche). CHO-K1 cells into which the above recombinant vector had been introduced were plated in a 96-well plate at 0.5 cells per well. Thus, a cell line stably producing a human-chicken chimeric antibody #1 (also referred to as #1) having the chicken monoclonal antibody #1 variable region was prepared. The thus prepared cell line was cultured in a 150 cm² flask containing 30 ml of serum-free OptiCHO medium (Invitrogen) at 5×10⁵ cells/ml for 5 days. Then, a culture supernatant containing #1 was obtained.

With a method similar to the above, the above recombinant vector into which the heavy chain variable region represented by SEQ ID NO: 43 had been inserted, and the above recombinant vector into which the chicken monoclonal antibody #2 light chain variable region represented by SEQ ID NO: 53 had been inserted, were introduced into CHO-K1 cells. Thus, a cell line stably producing a human-chicken chimeric antibody #2 (also referred to as #2) having the chicken monoclonal antibody #2-derived variable regions was prepared. The thus prepared cell line was cultured in a 150 cm² flask containing a serum-free OptiCHO medium (Invitrogen) for 5 days, and then a culture supernatant containing #2 was obtained.

(3) CAPRIN-1 Expression on Various Cancer Cell Surfaces Using Anti-CAPRIN-1 Antibodies #1 and #2

Next, 7 breast cancer cell lines (MDA-MB-157, T47D, MRK-nu-1, MDA-MB-231V, BT20, SK-BR-3, and DA-MB-231T) for which CAPRIN-1 gene expression had been observed, and the other 3 breast cancer cell lines (MDA-MB-231C, MCF-7, and ZR75-1), 5 glioma cell lines (T98G, SNB19, U251, U87MG, and U373), 4 renal cancer cell lines (Caki-1, Caki-2, A498, and ACHN), 2 gastric cancer cell lines (MKN28 and MKN45), 5 colorectal cancer cell lines (HT29, LoVo, Caco2, SW480, and HCT116), 3 lung cancer cell lines (A549, QG56, and PC8), 4 leukemia cell lines (AML5, Namalwa, BDCM, RPI1788), one uterine cervix cancer cell line (SW756), one bladder cancer cell line (T24), one esophageal cancer cell line (KYSE180), and one lymphoma cell line (Ramos) were examined for CAPRIN-1 protein expression on the cell surfaces using the culture supernatants (obtained in (2) above) of CHO-K1 cells containing #1 and #2. $10^6$ cells of each cell line were centrifuged in a 1.5 ml microcentrifuge tube. Each cell culture supernatant (100 µl) containing #1 or #2 obtained in (2) above was added and then left to stand on ice for 1 hour. After washing with PBS, a FITC-labeled goat-anti human IgG (H+L) antibody (SouthernBiotech) diluted 500-fold with PBS containing 0.1% FBS was added and then the resultant was left to stand on ice for 1 hour. After washing with PBS, fluorescence intensity was measured using a FACS Calibur (Becton, Dickinson and Company). Meanwhile, as a negative control, procedures similar to the above were performed using a culture supernatant of CHO-K1 cells into which no antibody gene had been introduced, instead of the culture supernatant of CHO-K1 cells containing #1 and #2. As a result, cells to which the human-chicken chimeric antibodies #1 and #2 had been added exhibited fluorescence intensity stronger by 20% or more than that of the control. Specifically, when the antibody #1 was used, fluorescence intensity was enhanced to 217% in the case of MDA-MB-157, 326% in the case of T47D, 125% in the case of MRK-nu-1, 527% in the case of MDA-MB-231V, 200% in the case of BT20, and 327% in the case of MDA-MB-231T. Also, when the antibody #2 was used, fluorescence intensity was enhanced to levels almost equivalent to the levels when the antibody #1 was used. It was revealed by these results that the CAPRIN-1 protein was expressed on the cell membrane surfaces of the above various human cancer cell lines. The percentage of enhancement in the above fluorescence intensity was expressed as percentage of increase in mean fluorescence intensity (MFI level) in each type of cell and calculated by the following formula.

Percentage of increase in mean fluorescence intensity (percentage of enhancement in fluorescence intensity)(%)=((MFI level in cells having reacted with anti-human CAPRIN-1 antibody)−(MFI level of the control))/(MFI level of control)×100.

Figure 2:
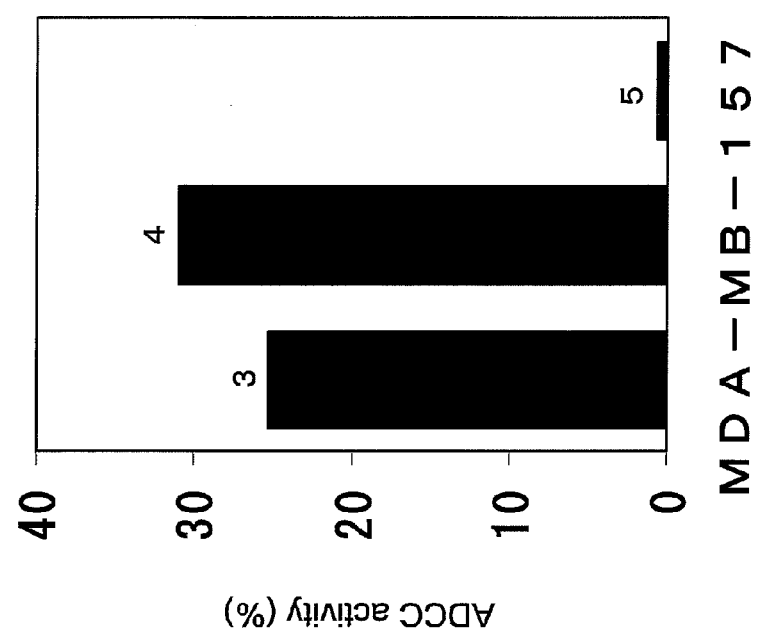
FIG. 2 shows the cytotoxicity to the MDA-MB-157 breast cancer cell line expressing CAPRIN-1 by anti-CAPRIN-1 monoclonal antibodies (#1 and #2) that are reactive with the surfaces of the cancer cells. Reference No. 3 indicates the activity exhibited when the anti-CAPRIN-1 monoclonal antibody #1 was added. Reference No. 4 indicates the activity exhibited when the anti-CAPRIN-1 monoclonal antibody #2 was added. Reference No. 5 indicates the activity exhibited when PBS was added instead of the antibodies.

(4) Anti-Tumor Effects (ADCC Activity) of Anti-CAPRIN-1 Antibodies #1 and #2 on Cancer Cells Next, the anti-CAPRIN-1 antibodies #1 and #2 were evaluated for their cellular cytotoxicity against cancer cells. Each cell culture supernatant producing #1 or #2 obtained in (2) above was purified using Hitrap ProteinA Sepharose FF (GE HEALTHCARE), subjected to buffer replacement with PBS (−), and then filtered with a 0.22 µm filter (Millipore). The resultants were used as antibodies for activity measurement. $10^6$ cells of MDA-MB-157 human breast cancer cell line were collected in a 50-ml centrifuge tube, 100 µCi chromium-51 was added, and then incubation was performed at 37° C. for 2 hours. Subsequently, the resultant was washed three times with RPMI 1640 medium containing 10% FBS. Cells were added to a 96-well V-bottom plate at $10^3$ cells per well for use as target cells. The above purified antibodies (1 µg) were added to the cells. $10^5$ cells of lymphocytes separated from human peripheral blood according to a conventional method were further added and then cultured under conditions of 37° C. and 5% $CO_2$ for 4 hours. After culture, the amount of chromium-51 released from damaged tumor cells in a culture supernatant was measured, and the cytotoxic activity of each anti-CAPRIN-1 antibody against cancer cells was calculated. As negative control samples, a sample prepared by adding PBS instead of the anti-CAPRIN-1 antibodies and a sample prepared by adding an isotype control antibody instead of anti-CAPRIN-1 antibodies were used. As a result, the antibodies #1 and #2 exhibited 25.3% activity and 31% activity, respectively, against MDA-MB-157 (see FIG. 2). In contrast, the activity in the sample prepared by adding PBS as a negative control and the activity in the sample prepared by adding the isotype control antibody as a negative control were 1.6% and 3.3%, respectively. Similarly, the antibodies #1 and #2 were examined for their cytotoxic activity against other cancer cells including glioma cell lines T98G and U373, lung cancer cell lines A549 and QG56, renal cancer cell lines Caki-1 and ACHN, a uterine cervix cancer cell line SW756, a bladder cancer cell line T24, an esophageal cancer cell line KYSE180, gastric cancer cell lines MKN28 and MKN45, a colorectal cancer cell line SW480, a leukemia cell line AML5, and a lymphoma cell line Ramos. As a result, the antibody #1 exhibited 10.5% activity against T98G (1.3% in the case of the isotype control), 10.9% against U373 (3% in the case of the isotype control), 14.0% against A549 (2.6% in the case of the isotype control), 15.9% against QG56 (0.2% in the case of the isotype control), 10.9% against Caki-1 (3.0% in the case of the isotype control), 12.6% against ACHN (1.5% in the case of the isotype control), 11.8% against SW756 (2.5% in the case of the isotype control), 12.3% against T24 (2.1% in the case of the isotype control), 17.7% against KYSE180 (3.0% in the case of the isotype control), 10.1% against MKN28 (1.7% in the case of the isotype control), 9.4% against MKN45 (2.3% in the case of the isotype control), 10.3% against SW480 (1.3% in the case of the isotype control), 8.3% against AML5 (2.1% in the case of the isotype control), and 9.5% against Ramos (3.8% in the case of the isotype control). Also, similar results were shown in the case of the antibody #2. It was demonstrated by the above results that the thus obtained anti-CAPRIN-1 antibodies #1 and #2 damage various human cancer cells expressing CAPRIN-1.

(5) Anti-Tumor Effects (CDC Activity) of Anti-CAPRIN-1 Antibodies #1 and #2 Against Cancer Cell Next, anti-CAPRIN-1 antibodies #1 and #2 were evaluated for their cytotoxic activity (CDC activity) against cancer cells. Blood collected from a rabbit was added to an Eppendorf tube, left to stand at room temperature for 60 minutes, and then subjected to 5 minutes of centrifugation at 3000 rpm. Thus, serum for measurement of CDC activity was prepared. $10^5$ cells of human breast cancer cells MDA-MB-231V were collected in a 50-ml centrifuge tube, 100 µCi chromium-51 was added, and then incubation was performed at 37° C. for 2 hours. The resultant was washed three times with RPMI medium containing 10% FBS. Subsequently, the cells were suspended in RPMI medium containing the above-prepared rabbit serum (50%), and then added to a 96-well V-bottom plate at $10^3$ cells per well. 1 µg of #1 and #2 obtained in (4) above were separately added to the cells and then cells were cultured under conditions of 37° C. and 5% $CO_2$ for 4 hours. After culture, the amount of chromium-51 released from damaged tumor cells in a culture supernatant was measured, and then the CDC activity of each antibody against MDA-MB-231V was calculated. As a result, the antibodies #1 and #2 both exhibited at least 30% CDC activity. Therefore, it was revealed that #1 and #2 can damage tumor cells expressing CAPRIN-1 also by CDC activity.

Example 5

In Vivo Anti-Tumor Effects of Anti-CAPRIN-1 Antibodies #1 and #2 in Mice

Next, the thus obtained anti-CAPRIN-1 antibodies #1 and #2 were evaluated for their in vivo anti-tumor effects in tumor-bearing mice. Antibodies used herein were prepared by column purification of the culture supernatant of each cell producing #1 or #2 in the same manner as described above.

Figure 3:
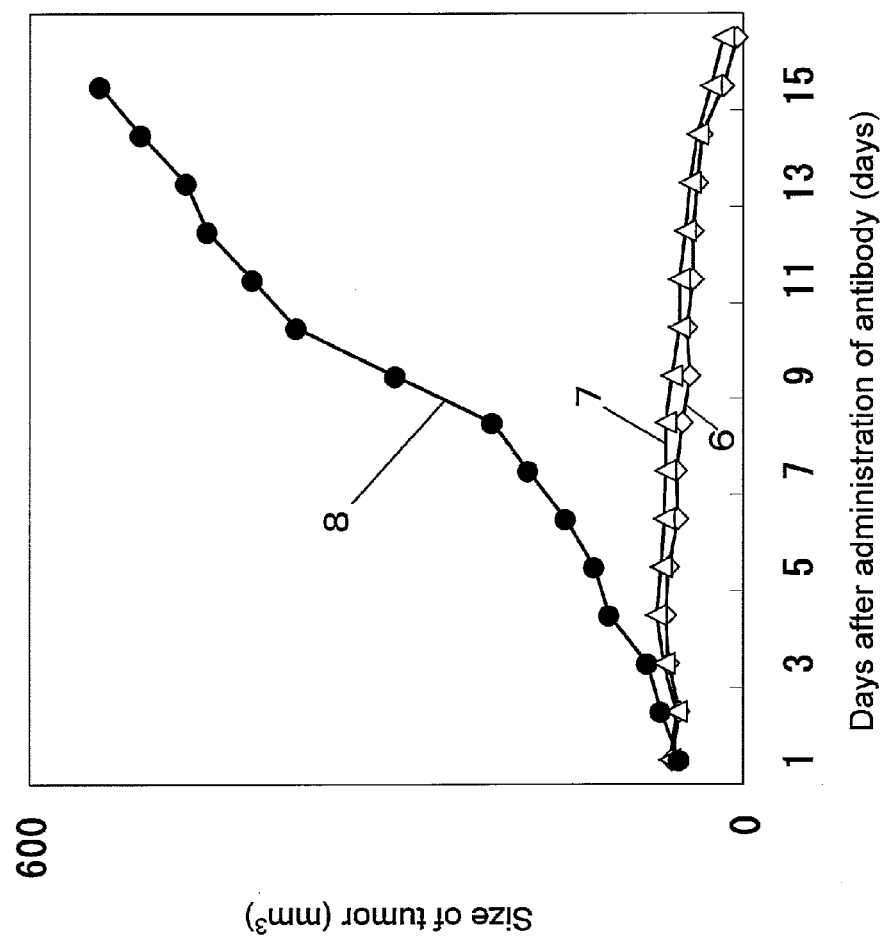
FIG. 3 shows the anti-tumor effect of the anti-CAPRIN-1 monoclonal antibodies (#1 and #2), which are reactive with the surfaces of cancer cells, on Balb/c mice into which the mouse breast cancer cell line 4T1 expressing CAPRIN-1 was transplanted. Reference No. 6 indicates the tumor size of a mouse to which the anti-CAPRIN-1 monoclonal antibody #1 was administered. Reference No. 7 indicates the tumor size of a mouse to which the anti-CAPRIN-1 monoclonal antibody #2 was administered. Reference No. 8 indicates the tumor size of a mouse to which PBS was administered instead of the antibodies.

The anti-tumor effects of the antibodies #1 and #2 were examined using tumor-bearing mice into which a mouse-derived cancer cell line expressing CAPRIN-1 had been transplanted. 4T1 cells (purchased from ATCC) were transplanted subcutaneously to the dorsal region of 30 Balb/c mice (Japan SLC Inc.) at $10^6$ cells per mouse. Tumor was allowed to grow to reach a size of about 5 mm in diameter. The antibodies #1 and #2 were each administered intraperitoneally to 10 mice from among the 30 tumor-bearing mice in an amount of 300 µg (in 300 µl) per mouse. Subsequently, the same amount of the antibody was administered intraperitoneally to each tumor-bearing mouse 3 times in total within 2 days. Tumor sizes were measured every day and anti-tumor effects were examined by observation. Meanwhile, as a control group, PBS (−) was administered instead of the antibodies to the remaining 10 tumor-bearing mice. As a result of the observation of the anti-tumor effects, in the test group to which the anti-CAPRIN-1 antibody #1 or #2 had been administered, tumors were found to have regressed to 70% and 80%, respectively, on day 11 and 8% and 26%, respectively, on day 15, compared to the tumor volume at the initiation of the antibody administration being 100% (see FIG. 3). In the control group to which PBS(−) had been administered, the tumor size was increased to about 230%, 340%, 550%, and 840% on days 4, 6, 8, and 11, respectively (see FIG. 3). It was demonstrated by the results that the obtained antibodies #1 and #2 exhibit strong anti-tumor effects in vivo against cancer cells expressing CAPRIN-1. The tumor size was calculated as a volume using the formula: length of major axis×length of minor axis×length of minor axis×0.5.

Example 6

Identification of Epitope in CAPRIN-1 Protein, to Which Anti-CAPRIN-1 Antibodies #1 and #2 Bind With the use of the anti-CAPRIN-1 antibodies #1 and #2 obtained in Example 4 (2) reacting with the cell surfaces of cancer cells, an epitope peptide in a CAPRIN-1 protein to be recognized by the antibodies was identified. 93 candidate peptides, each consisting of 12 to 16 amino acids in the amino acid sequence of the human CAPRIN-1 protein, were synthesized. Each peptide was dissolved in DMSO at a concentration of 1 mg/ml.

Each peptide was dissolved in 0.1M sodium carbonate buffer (pH 9.6) at a concentration of 30 µg/ml, added to a 96-well plate (Nunc, Product No. 436006) at 100 µl per well, and then left to stand at 4° C. overnight. The solution was discarded, 10 mM ethanolamine/0.1M sodium carbonate buffer (PH 9.6) was added at 200 µl per well, and then the plate was left to stand at room temperature for 1 hour. The solution was discarded, the plate was washed twice with PBS (PBST) containing 0.5% Tween20, so that the plate with each peptide immobilized thereto was prepared.

A cell culture supernatant containing the human-chicken chimeric monoclonal antibody obtained in Example 4 (2) was added to the plate at 50 µl per well. After 1 hour of shaking at room temperature, the solution was removed, and then the plate was washed three times with PBST. Next, an HRP-labeled anti-human IgG (Invitrogen, catalog No. 62-7120) antibody diluted 3000- to 4000-fold with PBST (a secondary antibody solution) was added at 50 µl per well and then the solution was removed, followed by washing six times with PBST.

A TMB substrate solution (Thermo) was added at 100 µl per well, and the plate was left to stand for 15 to 30 minutes for coloring reaction. After color development, 1N sulfuric acid was added at 100 µl per well to stop the reaction and then absorbances at 450 nm and 595 nm were measured using an absorption spectrometer. As a result, it was revealed that both #1 and #2 antibodies recognize the polypeptide of SEQ ID NO: 37, which is a partial sequence peptide in the CAPRIN-1 protein, and thus this polypeptide contains an epitope region for the anti-CAPRIN-1 antibodies #1 and #2.

INDUSTRIAL APPLICABILITY

The antibodies of the present invention are useful for treating and/or preventing cancer.

All publications, patents, and patent applications cited herein are incorporated herein by reference in their entirety.

SEQUENCE LISTING FREE TEXT

SEQ ID NOS: 31 to 36, 38, 39, 48, and 49: primer

The invention claimed is:

1. A method for treating and/or preventing recurrence of a CAPRIN-1 expressing cancer, comprising administering to a subject an antibody or a fragment thereof having immunological reactivity with a polypeptide that consists of the amino acid sequence of SEQ ID NO: 37.

2. A method for treating and/or preventing recurrence of a CAPRIN-1 expressing cancer, comprising administering to a subject a pharmaceutical combination comprising an antitumor agent, and
   an antibody or a fragment thereof as an active ingredient that has immunological reactivity with a partial polypeptide of CAPRIN-1, wherein CAPRIN-1 is any of the even-numbered sequences of SEQ ID NOS: 2 to 30, and wherein the partial polypeptide consists of the amino acid sequence of SEQ ID NO: 37, or
   an antibody or a fragment thereof having immunological reactivity with a polypeptide that consists of the amino acid sequence of SEQ ID NO: 37.

3. A method for treating and/or preventing recurrence of a CAPRIN-1 expressing cancer, comprising
   administering to a subject an antibody or a fragment thereof as an active ingredient that has immunological reactivity with a partial polypeptide of CAPRIN-1,
   wherein CAPRIN-1 is any of the even-numbered sequences of SEQ ID NOS: 2 to 30, and
   wherein the partial polypeptide of CAPRIN-1 consists of the amino acid sequence of SEQ ID NO: 37.

4. The method of claim 1, wherein the cancer is breast cancer, brain tumor, leukemia, lymphoma, lung cancer, mastocytoma, renal cancer, uterine cervix cancer, bladder cancer, esophageal cancer, gastric cancer, or colorectal cancer.

5. The method of claim 1, wherein the antibody is a monoclonal antibody or a polyclonal antibody.

6. The method of claim 1, wherein the antibody is a human antibody, humanized antibody, chimeric antibody, single chain antibody, or bispecific antibody.

7. The method of claim 2, wherein the cancer is breast cancer, brain tumor, leukemia, lymphoma, lung cancer, mastocytoma, renal cancer, uterine cervix cancer, bladder cancer, esophageal cancer, gastric cancer, or colorectal cancer.

8. The method of claim 2, wherein the antibody is a monoclonal antibody or a polyclonal antibody.

9. The method of claim 2, wherein the antibody is a human antibody, humanized antibody, chimeric antibody, single chain antibody, or bispecific antibody.

10. The method of claim 2, wherein the antibody or a fragment thereof has a cytotoxic activity against a cancer cell expressing a CAPRIN-1 protein.

11. The method of claim 3, wherein the cancer is breast cancer, brain tumor, leukemia, lymphoma, lung cancer, mastocytoma, renal cancer, uterine cervix cancer, bladder cancer, esophageal cancer, gastric cancer, or colorectal cancer.

12. The method of claim 3, wherein the antibody is a monoclonal antibody or a polyclonal antibody.

13. The method of claim 3, wherein the antibody is a human antibody, humanized antibody, chimeric antibody, single chain antibody, or bispecific antibody.

* * * * *

SEQUENCE LISTING

```
<160> NUMBER OF SEQ ID NOS: 58

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccttg cccctcagc tgcccactcg tgatttccag cggcctccgc      180 gcgcgcacg atg ccc tcg gcc acc agc cac agc ggg agc ggc agc aag tcg     231
            Met Pro Ser Ala Thr Ser His Ser Gly Ser Gly Ser Lys Ser
            1               5                  10
```

-continued

| | | |
|---|---|---|
| tcc gga ccg cca ccg ccg tcg ggt tcc tcc ggg agt gag gcg gcc gcg<br>Ser Gly Pro Pro Pro Pro Ser Gly Ser Ser Gly Ser Glu Ala Ala Ala<br>15                              20                      25                     30 | 279 |
| gga gcc ggg gcc gcc gcg ccg gct tct cag cac ccc gca acc ggc acc<br>Gly Ala Gly Ala Ala Ala Pro Ala Ser Gln His Pro Ala Thr Gly Thr<br>                         35                      40                         45 | 327 |
| ggc gct gtc cag acc gag gcc atg aag cag att ctc ggg gtg atc gac<br>Gly Ala Val Gln Thr Glu Ala Met Lys Gln Ile Leu Gly Val Ile Asp<br>                50                      55                      60 | 375 |
| aag aaa ctt cgg aac ctg gag aag aaa aag ggt aag ctt gat gat tac<br>Lys Lys Leu Arg Asn Leu Glu Lys Lys Lys Gly Lys Leu Asp Asp Tyr<br>            65                      70                      75 | 423 |
| cag gaa cga atg aac aaa ggg gaa agg ctt aat caa gat cag ctg gat<br>Gln Glu Arg Met Asn Lys Gly Glu Arg Leu Asn Gln Asp Gln Leu Asp<br>80                            85                      90 | 471 |
| gcc gtt tct aag tac cag gaa gtc aca aat aat ttg gag ttt gca aaa<br>Ala Val Ser Lys Tyr Gln Glu Val Thr Asn Asn Leu Glu Phe Ala Lys<br>95                           100                    105                110 | 519 |
| gaa tta cag agg agt ttc atg gca cta agt caa gat att cag aaa aca<br>Glu Leu Gln Arg Ser Phe Met Ala Leu Ser Gln Asp Ile Gln Lys Thr<br>                         115                    120                125 | 567 |
| ata aag aag aca gca cgt cgg gag cag ctt atg aga gaa gaa gct gaa<br>Ile Lys Lys Thr Ala Arg Arg Glu Gln Leu Met Arg Glu Glu Ala Glu<br>              130                    135                    140 | 615 |
| cag aaa cgt tta aaa act gta ctt gag cta cag tat gtt ttg gac aaa<br>Gln Lys Arg Leu Lys Thr Val Leu Glu Leu Gln Tyr Val Leu Asp Lys<br>                145                    150                    155 | 663 |
| ttg gga gat gat gaa gtg cgg act gac ctg aaa caa ggt ttg aat gga<br>Leu Gly Asp Asp Glu Val Arg Thr Asp Leu Lys Gln Gly Leu Asn Gly<br>160                             165                    170 | 711 |
| gtg cca ata ttg tcc gaa gag gag ttg tca ttg ttg gat gaa ttc tat<br>Val Pro Ile Leu Ser Glu Glu Glu Leu Ser Leu Leu Asp Glu Phe Tyr<br>175                         180                    185                190 | 759 |
| aag cta gta gac cct gaa cgg gac atg agc ttg agg ttg aat gaa cag<br>Lys Leu Val Asp Pro Glu Arg Asp Met Ser Leu Arg Leu Asn Glu Gln<br>                    195                    200                    205 | 807 |
| tat gaa cat gcc tcc att cac ctg tgg gac ctg ctg gaa ggg aag gaa<br>Tyr Glu His Ala Ser Ile His Leu Trp Asp Leu Leu Glu Gly Lys Glu<br>              210                    215                    220 | 855 |
| aaa cct gta tgt gga acc acc tat aaa gtt cta aag gaa att gtt gag<br>Lys Pro Val Cys Gly Thr Thr Tyr Lys Val Leu Lys Glu Ile Val Glu<br>              225                    230                    235 | 903 |
| cgt gtt ttt cag tca aac tac ttt gac agc acc cac aac cac cag aat<br>Arg Val Phe Gln Ser Asn Tyr Phe Asp Ser Thr His Asn His Gln Asn<br>240                             245                    250 | 951 |
| ggg ctg tgt gag gaa gaa gag gca gcc tca gca cct gca gtt gaa gac<br>Gly Leu Cys Glu Glu Glu Glu Ala Ala Ser Ala Pro Ala Val Glu Asp<br>255                             260                    265                270 | 999 |
| cag gta cct gaa gct gaa cct gag cca gca gaa gag tac act gag caa<br>Gln Val Pro Glu Ala Glu Pro Glu Pro Ala Glu Glu Tyr Thr Glu Gln<br>                    275                    280                    285 | 1047 |
| agt gaa gtt gaa tca aca gag tat gta aat aga cag ttc atg gca gaa<br>Ser Glu Val Glu Ser Thr Glu Tyr Val Asn Arg Gln Phe Met Ala Glu<br>              290                    295                    300 | 1095 |
| aca cag ttc acc agt ggt gaa aag gag cag gta gat gag tgg aca gtt<br>Thr Gln Phe Thr Ser Gly Glu Lys Glu Gln Val Asp Glu Trp Thr Val<br>                    305                    310                    315 | 1143 |
| gaa acg gtt gag gtg gta aat tca ctc cag cag caa cct cag gct gca<br>Glu Thr Val Glu Val Val Asn Ser Leu Gln Gln Gln Pro Gln Ala Ala<br>320                             325                    330 | 1191 |

| | |
|---|---|
| tcc cct tca gta cca gag ccc cac tct ttg act cca gtg gct cag gca<br>Ser Pro Ser Val Pro Glu Pro His Ser Leu Thr Pro Val Ala Gln Ala<br>335                         340                     345                   350 | 1239 |
| gat ccc ctt gtg aga aga cag cga gta caa gac ctt atg gca caa atg<br>Asp Pro Leu Val Arg Arg Gln Arg Val Gln Asp Leu Met Ala Gln Met<br>                    355                   360                   365 | 1287 |
| cag ggt ccc tat aat ttc ata cag gat tca atg ctg gat ttt gaa aat<br>Gln Gly Pro Tyr Asn Phe Ile Gln Asp Ser Met Leu Asp Phe Glu Asn<br>           370                   375                   380 | 1335 |
| cag aca ctt gat cct gcc att gta tct gca cag cct atg aat cca aca<br>Gln Thr Leu Asp Pro Ala Ile Val Ser Ala Gln Pro Met Asn Pro Thr<br>385                         390                     395 | 1383 |
| caa aac atg gac atg ccc cag ctg gtt tgc cct cca gtt cat tct gaa<br>Gln Asn Met Asp Met Pro Gln Leu Val Cys Pro Pro Val His Ser Glu<br>        400                   405                   410 | 1431 |
| tct aga ctt gct cag cct aat caa gtt cct gta caa cca gaa gcg aca<br>Ser Arg Leu Ala Gln Pro Asn Gln Val Pro Val Gln Pro Glu Ala Thr<br>415                         420                   425                430 | 1479 |
| cag gtt cct ttg gta tca tcc aca agt gag ggg tac aca gca tct caa<br>Gln Val Pro Leu Val Ser Ser Thr Ser Glu Gly Tyr Thr Ala Ser Gln<br>                    435                   440                   445 | 1527 |
| ccc ttg tac cag cct tct cat gct aca gag caa cga cca cag aag gaa<br>Pro Leu Tyr Gln Pro Ser His Ala Thr Glu Gln Arg Pro Gln Lys Glu<br>           450                   455                   460 | 1575 |
| cca att gat cag att cag gca aca atc tct tta aat aca gac cag act<br>Pro Ile Asp Gln Ile Gln Ala Thr Ile Ser Leu Asn Thr Asp Gln Thr<br>465                         470                     475 | 1623 |
| aca gca tca tca tcc ctt cct gct gcg tct cag cct caa gta ttt cag<br>Thr Ala Ser Ser Ser Leu Pro Ala Ala Ser Gln Pro Gln Val Phe Gln<br>        480                   485                   490 | 1671 |
| gct ggg aca agc aaa cct tta cat agc agt gga atc aat gta aat gca<br>Ala Gly Thr Ser Lys Pro Leu His Ser Ser Gly Ile Asn Val Asn Ala<br>495                         500                     505                510 | 1719 |
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                    515                   520                   525 | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>       530                   535                   540 | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>545                         550                     555 | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>        560                   565                   570 | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                         580                     585                590 | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                    595                   600                   605 | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>           610                   615                   620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>625                         630                     635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser | 2151 |

```
                640             645             650
cag ttc agt gct ccc cgg gat tac tct ggc tat caa cgg gat gga tat    2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc    2247
Gln Gln Asn Phe Lys Arg Gly Ser Gly Gln Ser Gly Pro Arg Gly Ala
                675                 680                 685 cca cga ggt cgt gga ggg ccc cca aga ccc aac aga ggg atg ccg caa    2295
Pro Arg Gly Arg Gly Gly Pro Pro Arg Pro Asn Arg Gly Met Pro Gln
            690                 695                 700 atg aac act cag caa gtg aat taa tctgattcac aggattatgt ttaatcgcca   2349
Met Asn Thr Gln Gln Val Asn
            705 aaaacacact ggccagtgta ccataatatg ttaccagaag agttattatc tatttgttct   2409 cccctttcagg aaacttattg taaagggact gttttcatcc cataaagaca ggactacaat  2469
```

```
catctgcctg ggatgtacca caaccatatg ttacctgtat cttaggggaa tggataaaat    4269
atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaagggatg ggggagaaaa tgccttctag    4449
gttttgaact tctatgcatt agtgcagatg ttgtgaatgt gtaaaggtgt tcatagtttg    4509
actgttctta tgtatgtttt ttcaaagaat tgttcctttt tttgaactat aattttctt    4569 tttttggtta ttttaccatc acagtttaaa tgtatatctt ttatgtctct actcagacca    4629
tatttttaaa ggggtgcctc attatggggc agagaacttt tcaataagtc tcattaagat    4689
ctgaatcttg gttctaagca ttctgtataa tatgtgattg cttgtcctag ctgcagaagg    4749
ccttttgttt ggtcaaatgc atattttagc agagtttcaa ggaaatgatt gtcacacatg    4809
tcactgtagc ctcttggtgt agcaagctca catacaaaat acttttgtat atgcataata    4869
taaatcatct catgtggata tgaaacttct tttttaaaac ttaaaaggt agaatgttat    4929 tgattacctt gattagggca gttttatttc cagatcctaa taattcctaa aaaatatgga    4989
aaagtttttt ttcaatcatt gtaccttgat attaaaacaa atatccttta agtatttcta    5049
atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
tcattttatg tttaagctcc tgaatctgca ttccacttgg gttgttttta agcattctaa    5349
attttagttg attataagtt agatttcaca gaatcagtat tgcccttgat cttgtccttt    5409
ttatggagtt aacggggagg aagaccctc aggaaaacga agtaaattg ttaaggctca    5469 tcttcatacc ttttccatt ttgaatccta caaaatact gcaaagact agtgaatgtt    5529 taaaattaca ctagattaaa aatatgaaa gtc                                  5562
```

<210> SEQ ID NO 2
<211> LENGTH: 709
<212> TYPE: PRT
<213> ORGANISM: Homo sapiens

<400> SEQUENCE: 2

Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
            35                  40                  45

Val Gln Thr Glu Ala Met Lys Gln Ile Leu Gly Val Ile Asp Lys Lys
        50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

```
Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
            195                 200                 205

His Ala Ser Ile His Leu Trp Asp Leu Leu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
            275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
            355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
            435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
    515                 520                 525

Val Asn Glu Pro Glu Thr Leu Lys Gln Gln Asn Gln Tyr Gln Ala Ser
530                 535                 540

Tyr Asn Gln Ser Phe Ser Ser Gln Pro His Gln Val Glu Gln Thr Glu
```

```
                545                 550                 555                 560
Leu Gln Gln Glu Gln Leu Gln Thr Val Val Gly Thr Tyr His Gly Ser
                    565                 570                 575

Pro Asp Gln Ser His Gln Val Thr Gly Asn His Gln Pro Pro Gln
                580                 585                 590

Gln Asn Thr Gly Phe Pro Arg Ser Asn Gln Pro Tyr Tyr Asn Ser Arg
                595                 600                 605

Gly Val Ser Arg Gly Ser Arg Gly Ala Arg Gly Leu Met Asn Gly
            610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
                660                 665                 670

Asn Phe Lys Arg Gly Ser Gly Gln Ser Gly Pro Arg Gly Ala Pro Arg
                675                 680                 685

Gly Arg Gly Gly Pro Pro Arg Pro Asn Arg Gly Met Pro Gln Met Asn
            690                 695                 700

Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 3
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc     180 gcgcgcacg atg ccc tcg gcc acc agc cac agc ggg agc ggc agc aag tcg    231
            Met Pro Ser Ala Thr Ser His Ser Gly Ser Gly Ser Lys Ser
            1               5                   10 tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac      375
Gly Ala Val Gln Thr Glu Ala Met Lys Gln Ile Leu Gly Val Ile Asp
        50                  55                  60 aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
    65                  70                  75 cag gaa cga atg aac aaa ggg gaa agg ctt aat caa gat cag ctg gat      471
Gln Glu Arg Met Asn Lys Gly Glu Arg Leu Asn Gln Asp Gln Leu Asp
80                  85                  90 gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca      567
Glu Leu Gln Arg Ser Phe Met Ala Leu Ser Gln Asp Ile Gln Lys Thr
```

-continued

|  |  |  |  |  |  |  |  |  |  |  |  |  |  |  |  |
|---|---|---|---|---|---|---|---|---|---|---|---|---|---|---|---|
|  |  |  | 115 |  |  |  | 120 |  |  |  | 125 |  |  |  |  |
| ata | aag | aag | aca | gca | cgt | cgg | gag | cag | ctt | atg | aga | gaa | gaa | gct | gaa | 615 |
| Ile | Lys | Lys | Thr | Ala | Arg | Arg | Glu | Gln | Leu | Met | Arg | Glu | Glu | Ala | Glu |  |
|  |  |  | 130 |  |  |  | 135 |  |  |  | 140 |  |  |  |  |
| cag | aaa | cgt | tta | aaa | act | gta | ctt | gag | cta | cag | tat | gtt | ttg | gac | aaa | 663 |
| Gln | Lys | Arg | Leu | Lys | Thr | Val | Leu | Glu | Leu | Gln | Tyr | Val | Leu | Asp | Lys |  |
|  |  | 145 |  |  |  |  | 150 |  |  |  |  | 155 |  |  |  |  |
| ttg | gga | gat | gat | gaa | gtg | cgg | act | gac | ctg | aaa | caa | ggt | ttg | aat | gga | 711 |
| Leu | Gly | Asp | Asp | Glu | Val | Arg | Thr | Asp | Leu | Lys | Gln | Gly | Leu | Asn | Gly |  |
|  | 160 |  |  |  |  | 165 |  |  |  |  | 170 |  |  |  |  |  |
| gtg | cca | ata | ttg | tcc | gaa | gag | gag | ttg | tca | ttg | ttg | gat | gaa | ttc | tat | 759 |
| Val | Pro | Ile | Leu | Ser | Glu | Glu | Glu | Leu | Ser | Leu | Leu | Asp | Glu | Phe | Tyr |  |
| 175 |  |  |  |  | 180 |  |  |  |  | 185 |  |  |  |  | 190 |  |
| aag | cta | gta | gac | cct | gaa | cgg | gac | atg | agc | ttg | agg | ttg | aat | gaa | cag | 807 |
| Lys | Leu | Val | Asp | Pro | Glu | Arg | Asp | Met | Ser | Leu | Arg | Leu | Asn | Glu | Gln |  |
|  |  |  |  | 195 |  |  |  |  | 200 |  |  |  |  | 205 |  |  |
| tat | gaa | cat | gcc | tcc | att | cac | ctg | tgg | gac | ctg | ctg | gaa | ggg | aag | gaa | 855 |
| Tyr | Glu | His | Ala | Ser | Ile | His | Leu | Trp | Asp | Leu | Leu | Glu | Gly | Lys | Glu |  |
|  |  |  | 210 |  |  |  | 215 |  |  |  | 220 |  |  |  |  |
| aaa | cct | gta | tgt | gga | acc | acc | tat | aaa | gtt | cta | aag | gaa | att | gtt | gag | 903 |
| Lys | Pro | Val | Cys | Gly | Thr | Thr | Tyr | Lys | Val | Leu | Lys | Glu | Ile | Val | Glu |  |
|  |  | 225 |  |  |  |  | 230 |  |  |  |  | 235 |  |  |  |  |
| cgt | gtt | ttt | cag | tca | aac | tac | ttt | gac | agc | acc | cac | aac | cac | cag | aat | 951 |
| Arg | Val | Phe | Gln | Ser | Asn | Tyr | Phe | Asp | Ser | Thr | His | Asn | His | Gln | Asn |  |
|  | 240 |  |  |  |  | 245 |  |  |  |  | 250 |  |  |  |  |  |
| ggg | ctg | tgt | gag | gaa | gaa | gag | gca | gcc | tca | gca | cct | gca | gtt | gaa | gac | 999 |
| Gly | Leu | Cys | Glu | Glu | Glu | Glu | Ala | Ala | Ser | Ala | Pro | Ala | Val | Glu | Asp |  |
| 255 |  |  |  |  | 260 |  |  |  |  | 265 |  |  |  |  | 270 |  |
| cag | gta | cct | gaa | gct | gaa | cct | gag | cca | gca | gaa | gag | tac | act | gag | caa | 1047 |
| Gln | Val | Pro | Glu | Ala | Glu | Pro | Glu | Pro | Ala | Glu | Glu | Tyr | Thr | Glu | Gln |  |
|  |  |  |  | 275 |  |  |  |  | 280 |  |  |  |  | 285 |  |  |
| agt | gaa | gtt | gaa | tca | aca | gag | tat | gta | aat | aga | cag | ttc | atg | gca | gaa | 1095 |
| Ser | Glu | Val | Glu | Ser | Thr | Glu | Tyr | Val | Asn | Arg | Gln | Phe | Met | Ala | Glu |  |
|  |  |  | 290 |  |  |  | 295 |  |  |  | 300 |  |  |  |  |
| aca | cag | ttc | acc | agt | ggt | gaa | aag | gag | cag | gta | gat | gag | tgg | aca | gtt | 1143 |
| Thr | Gln | Phe | Thr | Ser | Gly | Glu | Lys | Glu | Gln | Val | Asp | Glu | Trp | Thr | Val |  |
|  |  | 305 |  |  |  |  | 310 |  |  |  |  | 315 |  |  |  |  |
| gaa | acg | gtt | gag | gtg | gta | aat | tca | ctc | cag | cag | caa | cct | cag | gct | gca | 1191 |
| Glu | Thr | Val | Glu | Val | Val | Asn | Ser | Leu | Gln | Gln | Gln | Pro | Gln | Ala | Ala |  |
|  | 320 |  |  |  |  | 325 |  |  |  |  | 330 |  |  |  |  |  |
| tcc | cct | tca | gta | cca | gag | ccc | cac | tct | ttg | act | cca | gtg | gct | cag | gca | 1239 |
| Ser | Pro | Ser | Val | Pro | Glu | Pro | His | Ser | Leu | Thr | Pro | Val | Ala | Gln | Ala |  |
| 335 |  |  |  |  | 340 |  |  |  |  | 345 |  |  |  |  | 350 |  |
| gat | ccc | ctt | gtg | aga | aga | cag | cga | gta | caa | gac | ctt | atg | gca | caa | atg | 1287 |
| Asp | Pro | Leu | Val | Arg | Arg | Gln | Arg | Val | Gln | Asp | Leu | Met | Ala | Gln | Met |  |
|  |  |  |  | 355 |  |  |  |  | 360 |  |  |  |  | 365 |  |  |
| cag | ggt | ccc | tat | aat | ttc | ata | cag | gat | tca | atg | ctg | gat | ttt | gaa | aat | 1335 |
| Gln | Gly | Pro | Tyr | Asn | Phe | Ile | Gln | Asp | Ser | Met | Leu | Asp | Phe | Glu | Asn |  |
|  |  |  | 370 |  |  |  | 375 |  |  |  | 380 |  |  |  |  |
| cag | aca | ctt | gat | cct | gcc | att | gta | tct | gca | cag | cct | atg | aat | cca | aca | 1383 |
| Gln | Thr | Leu | Asp | Pro | Ala | Ile | Val | Ser | Ala | Gln | Pro | Met | Asn | Pro | Thr |  |
|  |  | 385 |  |  |  |  | 390 |  |  |  |  | 395 |  |  |  |  |
| caa | aac | atg | gac | atg | ccc | cag | ctg | gtt | tgc | cct | cca | gtt | cat | tct | gaa | 1431 |
| Gln | Asn | Met | Asp | Met | Pro | Gln | Leu | Val | Cys | Pro | Pro | Val | His | Ser | Glu |  |
|  | 400 |  |  |  |  | 405 |  |  |  |  | 410 |  |  |  |  |  |
| tct | aga | ctt | gct | cag | cct | aat | caa | gtt | cct | gta | caa | cca | gaa | gcg | aca | 1479 |
| Ser | Arg | Leu | Ala | Gln | Pro | Asn | Gln | Val | Pro | Val | Gln | Pro | Glu | Ala | Thr |  |
| 415 |  |  |  |  | 420 |  |  |  |  | 425 |  |  |  |  | 430 |  |
| cag | gtt | cct | ttg | gta | tca | tcc | aca | agt | gag | ggg | tac | aca | gca | tct | caa | 1527 |

-continued

| | | | | | | | | | | | | |
|---|---|---|---|---|---|---|---|---|---|---|---|---|
|Gln|Val|Pro|Leu|Val|Ser|Ser|Thr|Ser|Glu|Gly|Tyr|Thr|Ala|Ser|Gln|
| | | | |435| | | |440| | | |445|

```
ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460 cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490 gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540 gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555 aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570 ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605 agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620 aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635 tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650 cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                675                 680                 685 cca cga ggt aat att ttg tgg tgg tga tcctagctcc taagtggagc            2294
Pro Arg Gly Asn Ile Leu Trp Trp
            690 ttctgttctg gccttggaag agctgttaat agtctgcatg ttaggaatac atttatcctt    2354 tccagacttg ttgctaggga ttaaatgaaa tgctctgttt ctaaaactta atcttggacc    2414 caaatttaa ttttgaatg atttaatttt ccctgttact atataaactg tcttgaaaac      2474 tagaacatat tctcttctca gaaaagtgt ttttccaact gaaaattatt tttcaggtcc     2534 taaaacctgc taaatgtttt taggaagtac ttactgaaac attttgtaa gacattttg      2594 gaatgagatt gaacatttat ataaatttat tattcctctt tcattttttt gaaacatgcc    2654
```

| | |
|---|---|
| tattatattt tagggccaga caccctttaa tggccggata agccatagtt aacatttaga | 2714 |
| gaaccattta gaagtgatag aactaatgga atttgcaatg cctttggac ctctattagt | 2774 |
| gatataaata tcaagttatt tctgactttt aaacaaaact cccaaattcc taacttattg | 2834 |
| agctatactt aaaaaaaatt acaggtttag agagttttt gttttctttt tactgttgga | 2894 |
| aaactacttc ccattttggc aggaagttaa cctatttaac aattagagct agcatttcat | 2954 |
| gtagtctgaa attctaaatg gttctctgat tgagggagg ttaaacatca aacaggtttc | 3014 |
| ctctattggc cataacatgt ataaaatgtg tgttaaggag gaattacaac gtactttgat | 3074 |
| ttgaatacta gtagaaactg gccaggaaaa aggtacattt ttctaaaaat taatggatca | 3134 |
| cttgggaatt actgacttga ctagaagtat caaaggatgt ttgcatgtga atgtgggtta | 3194 |
| tgttctttcc caccttgtag catattcgat gaaagttgag ttaactgata gctaaaaatc | 3254 |
| tgttttaaca gcatgtaaaa agttatttta tctgttaaaa gtcattatac agttttgaat | 3314 |
| gttatgtagt ttcttttaa cagtttaggt aataaggtct gttttcattc tggtgctttt | 3374 |
| attaattttg atagtatgat gttacttact actgaaatg aagctagagt gtacactaga | 3434 |
| atgtaagctc catgagagca ggtaccttgt ctgtcttctc tgctgtatct attcccaacg | 3494 |
| cttgatgatg gtgcctggca catagtaggc actcaataaa tatttgttga atgaatgaa | 3553 |

```
<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Gly
1               5                   10                  15

Pro Pro Pro Ser Gly Ser Ser Gly Ser Glu Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Gly Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220
```

```
Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
            245                 250                 255

Cys Glu Glu Glu Ala Ala Ser Ala Pro Ala Val Glu Asp Gln Val
        260                 265                 270

Pro Glu Ala Glu Pro Pro Ala Glu Glu Tyr Thr Glu Gln Ser Glu
        275                 280                 285

Val Glu Ser Thr Glu Tyr Val Asn Arg Gln Phe Met Ala Glu Thr Gln
290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
            325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
            355                 360                 365

Pro Tyr Asn Phe Ile Gln Asp Ser Met Leu Asp Phe Glu Asn Gln Thr
            370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
            405                 410                 415

Leu Ala Gln Pro Asn Gln Val Pro Gln Pro Glu Ala Thr Gln Val
            420                 425                 430

Pro Leu Val Ser Ser Thr Ser Glu Gly Tyr Thr Ala Ser Gln Pro Leu
            435                 440                 445

Tyr Gln Pro Ser His Ala Thr Glu Gln Arg Pro Gln Lys Glu Pro Ile
            450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
            515                 520                 525

Val Asn Glu Pro Glu Thr Leu Lys Gln Gln Asn Gln Tyr Gln Ala Ser
            530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Pro Pro Gln
            580                 585                 590

Gln Asn Thr Gly Phe Pro Arg Ser Asn Gln Pro Tyr Tyr Asn Ser Arg
            595                 600                 605

Gly Val Ser Arg Gly Gly Ser Arg Gly Ala Arg Gly Leu Met Asn Gly
            610                 615                 620

Tyr Arg Gly Pro Ala Asn Gly Phe Arg Gly Gly Tyr Asp Gly Tyr Arg
625                 630                 635                 640
```

```
Pro Ser Phe Ser Asn Thr Pro Asn Ser Gly Tyr Thr Gln Ser Gln Phe
            645                 650                 655
Ser Ala Pro Arg Asp Tyr Ser Gly Tyr Gln Arg Asp Gly Tyr Gln Gln
            660                 665                 670
Asn Phe Lys Arg Gly Ser Gly Gln Ser Gly Pro Arg Gly Ala Pro Arg
            675                 680                 685
Gly Asn Ile Leu Trp Trp
            690

<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5
gtcacaaata acttggagtt tgcaaaagaa ttacagagga gtttc atg gca tta agt        57
                                                 Met Ala Leu Ser
                                                  1 caa gat att cag aaa aca ata aag aag act gca cgt cgg gag cag ctt        105
Gln Asp Ile Gln Lys Thr Ile Lys Lys Thr Ala Arg Arg Glu Gln Leu
 5                  10                  15                  20 atg aga gag gaa gcg gaa caa aaa cgt tta aaa act gta ctt gag ctc        153
Met Arg Glu Glu Ala Glu Gln Lys Arg Leu Lys Thr Val Leu Glu Leu
                25                  30                  35 cag tat gtt ttg gac aaa ttg gga gat gat gaa gtg aga act gac ctg        201
Gln Tyr Val Leu Asp Lys Leu Gly Asp Asp Glu Val Arg Thr Asp Leu
        40                  45                  50 aag caa ggt ttg aat gga gtg cca ata ttg tct gaa gaa gaa ttg tcg        249
Lys Gln Gly Leu Asn Gly Val Pro Ile Leu Ser Glu Glu Glu Leu Ser
    55                  60                  65 ttg ttg gat gaa ttc tac aaa tta gca gac cct gaa cgg gac atg agc        297
Leu Leu Asp Glu Phe Tyr Lys Leu Ala Asp Pro Glu Arg Asp Met Ser
70                  75                  80 ttg agg ttg aat gag cag tat gaa cat gct tcc att cac ctg tgg gac        345
Leu Arg Leu Asn Glu Gln Tyr Glu His Ala Ser Ile His Leu Trp Asp
85                  90                  95                 100 ttg ctg gaa gga aag gaa aag tct gta tgt gga aca acc tat aaa gca        393
Leu Leu Glu Gly Lys Glu Lys Ser Val Cys Gly Thr Thr Tyr Lys Ala
                105                 110                 115 cta aag gaa att gtt gag cgt gtt ttc cag tca aat tac ttt gac agc        441
Leu Lys Glu Ile Val Glu Arg Val Phe Gln Ser Asn Tyr Phe Asp Ser
            120                 125                 130 act cac aac cac cag aat ggg cta tgt gag gaa gaa gag gca gcc tca        489
Thr His Asn His Gln Asn Gly Leu Cys Glu Glu Glu Glu Ala Ala Ser
        135                 140                 145 gca cct aca gtt gaa gac cag gta gct gaa gct gag cct gag cca gca        537
Ala Pro Thr Val Glu Asp Gln Val Ala Glu Ala Glu Pro Glu Pro Ala
    150                 155                 160 gaa gaa tac act gaa caa agt gaa gtt gaa tca aca gag tat gta aat        585
Glu Glu Tyr Thr Glu Gln Ser Glu Val Glu Ser Thr Glu Tyr Val Asn
165                 170                 175                 180 aga caa ttt atg gca gaa aca cag ttc agc agt ggt gaa aag gag cag        633
Arg Gln Phe Met Ala Glu Thr Gln Phe Ser Ser Gly Glu Lys Glu Gln
                185                 190                 195 gta gat gag tgg acg gtc gaa aca gtg gag gtg gtg aat tca ctc cag        681
Val Asp Glu Trp Thr Val Glu Thr Val Glu Val Val Asn Ser Leu Gln
            200                 205                 210
```

```
cag caa cct cag gct gcg tct cct tca gta cca gag ccc cac tct ttg    729
Gln Gln Pro Gln Ala Ala Ser Pro Ser Val Pro Glu Pro His Ser Leu
        215                 220                 225 act ccg gtg gct cag gca gat ccc ctt gtg aga aga cag cga gtc cag    777
Thr Pro Val Ala Gln Ala Asp Pro Leu Val Arg Arg Gln Arg Val Gln
230                 235                 240 gac ctt atg gcg cag atg cag ggg ccc tat aat ttc ata cag gat tca    825
Asp Leu Met Ala Gln Met Gln Gly Pro Tyr Asn Phe Ile Gln Asp Ser
245                 250                 255                 260 atg ctg gat ttt gaa aac cag aca ctc gat cct gcc att gta tct gca    873
Met Leu Asp Phe Glu Asn Gln Thr Leu Asp Pro Ala Ile Val Ser Ala
                265                 270                 275 cag cct atg aat ccg aca caa aac atg gac atg ccc cag ctg gtt tgc    921
Gln Pro Met Asn Pro Thr Gln Asn Met Asp Met Pro Gln Leu Val Cys
            280                 285                 290 cct cca gtt cat tct gaa tct aga ctt gct caa cct aat caa gtt cct    969
Pro Pro Val His Ser Glu Ser Arg Leu Ala Gln Pro Asn Gln Val Pro
        295                 300                 305 gta caa cca gaa gct aca cag gtt cct ttg gtt tca tcc aca agt gag   1017
Val Gln Pro Glu Ala Thr Gln Val Pro Leu Val Ser Ser Thr Ser Glu
    310                 315                 320 ggg tat aca gca tct caa ccc ttg tac cag cct tct cat gct aca gag   1065
Gly Tyr Thr Ala Ser Gln Pro Leu Tyr Gln Pro Ser His Ala Thr Glu
325                 330                 335                 340 caa cga cca caa aag gaa cca att gac cag att cag gca aca atc tct   1113
Gln Arg Pro Gln Lys Glu Pro Ile Asp Gln Ile Gln Ala Thr Ile Ser
                345                 350                 355 tta aat aca gac cag act aca gcg tca tca tcc ctt ccg gct gct tct   1161
Leu Asn Thr Asp Gln Thr Thr Ala Ser Ser Ser Leu Pro Ala Ala Ser
            360                 365                 370 cag cct cag gta ttc cag gct ggg aca agc aaa cca tta cat agc agt   1209
Gln Pro Gln Val Phe Gln Ala Gly Thr Ser Lys Pro Leu His Ser Ser
        375                 380                 385 gga atc aat gta aat gca gct cca ttc caa tcc atg caa acg gtg ttc   1257
Gly Ile Asn Val Asn Ala Ala Pro Phe Gln Ser Met Gln Thr Val Phe
    390                 395                 400 aat atg aat gcc cca gtt cct cct gtt aat gaa cca gaa act ttg aaa   1305
Asn Met Asn Ala Pro Val Pro Pro Val Asn Glu Pro Glu Thr Leu Lys
405                 410                 415                 420 caa caa aat cag tac cag gcc agt tat aac cag agc ttt tct agt cag   1353
Gln Gln Asn Gln Tyr Gln Ala Ser Tyr Asn Gln Ser Phe Ser Ser Gln
                425                 430                 435 cct cac caa gta gaa caa aca gag gga tgc cgc aaa tga acactcagca   1402
Pro His Gln Val Glu Gln Thr Glu Gly Cys Arg Lys
            440                 445 agtgaattaa tctgattcac aggattatgt ttaaacgcca aaaacacact ggccagtgta   1462
ccataatatg ttaccagaag agttattatc tatttgttct ccctttcagg aaacttattg   1522
taaagggact gttttcatcc cataaagaca ggactacaat tgtcagcttt atattacctg   1582
gaaaaaaaaa aaaaaaaaaa aaa                                           1605

<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15
```

```
Arg Glu Gln Leu Met Arg Glu Glu Ala Glu Gln Lys Arg Leu Lys Thr
                20                  25                  30

Val Leu Glu Leu Gln Tyr Val Leu Asp Lys Leu Gly Asp Asp Glu Val
            35                  40                  45

Arg Thr Asp Leu Lys Gln Gly Leu Asn Gly Val Pro Ile Leu Ser Glu
50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
```

<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)

<400> SEQUENCE: 7

| | | | | | | | | | | | | | | | | |
|---|---|---|---|---|---|---|---|---|---|---|---|---|---|---|---|---|
| atg | ccg | tcg | gcc | acc | agc | ctc | agc | gga | agc | ggc | agc | aag | tcg | tcg | ggc | 48 |
| Met | Pro | Ser | Ala | Thr | Ser | Leu | Ser | Gly | Ser | Gly | Ser | Lys | Ser | Ser | Gly | |
| 1 | | | | 5 | | | | | 10 | | | | | 15 | | |
| ccg | ccg | ccc | ccg | tcg | ggt | tcc | tcc | ggg | agc | gag | gcg | gcg | gcg | gcg | gcg | 96 |
| Pro | Pro | Pro | Pro | Ser | Gly | Ser | Ser | Gly | Ser | Glu | Ala | Ala | Ala | Ala | Ala | |
| | | | 20 | | | | | 25 | | | | | 30 | | | |
| ggg | gcg | gcg | ggg | gcg | gcg | ggg | gcc | ggg | gcg | gct | gcg | ccc | gcc | tcc | cag | 144 |
| Gly | Ala | Ala | Gly | Ala | Ala | Gly | Ala | Gly | Ala | Ala | Ala | Pro | Ala | Ser | Gln | |
| | | 35 | | | | | 40 | | | | | 45 | | | | |
| cac | ccc | gcg | acc | ggc | acc | ggc | gct | gtc | cag | acc | gag | gcc | atg | aag | cag | 192 |
| His | Pro | Ala | Thr | Gly | Thr | Gly | Ala | Val | Gln | Thr | Glu | Ala | Met | Lys | Gln | |
| 50 | | | | | 55 | | | | | 60 | | | | | | |
| atc | ctc | ggg | gtg | atc | gac | aag | aaa | ctc | cgg | aac | ctg | gag | aag | aaa | aag | 240 |
| Ile | Leu | Gly | Val | Ile | Asp | Lys | Lys | Leu | Arg | Asn | Leu | Glu | Lys | Lys | Lys | |
| 65 | | | | | 70 | | | | | 75 | | | | | 80 | |
| ggc | aag | ctt | gat | gat | tac | cag | gaa | cga | atg | aac | aaa | ggg | gaa | agg | ctt | 288 |
| Gly | Lys | Leu | Asp | Asp | Tyr | Gln | Glu | Arg | Met | Asn | Lys | Gly | Glu | Arg | Leu | |
| | | | | 85 | | | | | 90 | | | | | 95 | | |
| aat | caa | gat | cag | ctg | gat | gcc | gta | tct | aag | tac | cag | gaa | gtc | aca | aat | 336 |
| Asn | Gln | Asp | Gln | Leu | Asp | Ala | Val | Ser | Lys | Tyr | Gln | Glu | Val | Thr | Asn | |
| | | | 100 | | | | | 105 | | | | | 110 | | | |
| aac | ttg | gag | ttt | gca | aaa | gaa | tta | cag | agg | agt | ttc | atg | gca | tta | agt | 384 |
| Asn | Leu | Glu | Phe | Ala | Lys | Glu | Leu | Gln | Arg | Ser | Phe | Met | Ala | Leu | Ser | |
| | | 115 | | | | | 120 | | | | | 125 | | | | |
| caa | gat | att | cag | aaa | aca | ata | aag | aag | act | gca | cgt | cgg | gag | cag | ctt | 432 |
| Gln | Asp | Ile | Gln | Lys | Thr | Ile | Lys | Lys | Thr | Ala | Arg | Arg | Glu | Gln | Leu | |
| 130 | | | | | 135 | | | | | 140 | | | | | | |
| atg | aga | gag | gaa | gcg | gaa | caa | aaa | cgt | tta | aaa | act | gta | ctt | gag | ctc | 480 |
| Met | Arg | Glu | Glu | Ala | Glu | Gln | Lys | Arg | Leu | Lys | Thr | Val | Leu | Glu | Leu | |
| 145 | | | | | 150 | | | | | 155 | | | | | 160 | |
| cag | tat | gtt | ttg | gac | aaa | ttg | gga | gat | gat | gaa | gtg | aga | act | gac | ctg | 528 |
| Gln | Tyr | Val | Leu | Asp | Lys | Leu | Gly | Asp | Asp | Glu | Val | Arg | Thr | Asp | Leu | |
| | | | | 165 | | | | | 170 | | | | | 175 | | |
| aag | caa | ggt | ttg | aat | gga | gtg | cca | ata | ttg | tct | gaa | gaa | gaa | ttg | tcg | 576 |
| Lys | Gln | Gly | Leu | Asn | Gly | Val | Pro | Ile | Leu | Ser | Glu | Glu | Glu | Leu | Ser | |
| | | | 180 | | | | | 185 | | | | | 190 | | | |
| ttg | ttg | gat | gaa | ttc | tac | aaa | tta | gca | gac | cct | gaa | cgg | gac | atg | agc | 624 |
| Leu | Leu | Asp | Glu | Phe | Tyr | Lys | Leu | Ala | Asp | Pro | Glu | Arg | Asp | Met | Ser | |
| | | 195 | | | | | 200 | | | | | 205 | | | | |
| ttg | agg | ttg | aat | gag | cag | tat | gaa | cat | gct | tcc | att | cac | ctg | tgg | gac | 672 |
| Leu | Arg | Leu | Asn | Glu | Gln | Tyr | Glu | His | Ala | Ser | Ile | His | Leu | Trp | Asp | |
| 210 | | | | | 215 | | | | | 220 | | | | | | |
| ttg | ctg | gaa | gga | aag | gaa | aag | tct | gta | tgt | gga | aca | acc | tat | aaa | gca | 720 |
| Leu | Leu | Glu | Gly | Lys | Glu | Lys | Ser | Val | Cys | Gly | Thr | Thr | Tyr | Lys | Ala | |
| 225 | | | | | 230 | | | | | 235 | | | | | 240 | |
| cta | aag | gaa | att | gtt | gag | cgt | gtt | ttc | cag | tca | aat | tac | ttt | gac | agc | 768 |
| Leu | Lys | Glu | Ile | Val | Glu | Arg | Val | Phe | Gln | Ser | Asn | Tyr | Phe | Asp | Ser | |
| | | | | 245 | | | | | 250 | | | | | 255 | | |
| act | cac | aac | cac | cag | aat | ggg | cta | tgt | gag | gaa | gaa | gag | gca | gcc | tca | 816 |
| Thr | His | Asn | His | Gln | Asn | Gly | Leu | Cys | Glu | Glu | Glu | Glu | Ala | Ala | Ser | |

-continued

```
              260                 265                 270
gca cct aca gtt gaa gac cag gta gct gaa gct gag cct gag cca gca        864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat        912
Glu Glu Tyr Thr Glu Gln Ser Glu Val Glu Ser Thr Glu Tyr Val Asn
290                 295                 300 aga caa ttt atg gca gaa aca cag ttc agc agt ggt gaa aag gag cag        960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag       1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg       1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag       1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca       1152
Asp Leu Met Ala Gln Met Gln Gly Pro Tyr Asn Phe Ile Gln Asp Ser
370                 375                 380 atg ctg gat ttt gaa aac cag aca ctc gat cct gcc att gta tct gca       1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc       1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct       1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag       1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag       1392
Gly Tyr Thr Ala Ser Gln Pro Leu Tyr Gln Pro Ser His Ala Thr Glu
450                 455                 460 caa cga cca caa aag gaa cca att gac cag att cag gca aca atc tct       1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct       1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt       1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc       1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa       1632
Asn Met Asn Ala Pro Val Pro Pro Val Asn Glu Pro Glu Thr Leu Lys
530                 535                 540 caa caa aat cag tac cag gcc agt tat aac cag agc ttt tct agt cag       1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca       1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act       1776
```

```
                    Val Val Gly Thr Tyr His Gly Ser Gln Asp Gln Pro His Gln Val Thr
                                    580                 585                 590 ggt aac cat cag cag cct ccc cag cag aac act gga ttt cca cgt agc                    1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt                    1872
Ser Gln Pro Tyr Tyr Asn Ser Arg Gly Val Ser Arg Gly Gly Ser Arg
        610                 615                 620 ggt gct aga ggc tta atg aat gga tac agg ggc cct gcc aat gga ttc                    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac                    1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc                    2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag                    2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc                    2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa                            2154
Asn Arg Gly Met Pro Gln Met Asn Thr Gln Gln Val Asn
705                 710                 715 tctgattcac aggattatgt ttaaacgcca aaaacacact ggccagtgta ccataatatg                  2214
ttaccagaag agttattatc tatttgttct ccctttcagg aaacttattg taaagggact                  2274
gttttcatcc cataaagaca ggactacaat tgtcagcttt atattacctg gatatggaag                  2334
gaaactattt ttattctgca tgttcttcct aagcgtcatc ttgagcctg cacatgatac                   2394 tcagattcct caccettget taggagtaaa acataataca ctttacaggg tgatatctcc                  2454
atagttattt gaagtggctt ggaaaaagca agattaactt ctgacattgg ataaaaatca                  2514
acaaatcagc cctagagtta ttcaaatggt aattgacaaa aactaaaata tttcccttcg                  2574
agaaggagtg aatgtggtt tggcagaaca actgcatttc acagcttttc cggttaaatt                   2634
ggagcactaa acgtttagat gcataccaaa ttatgcatgg gcccttaata taaaaggctg                  2694
gctaccagct ttgacacagc actattcatc ctctggccaa acaactgtgg ttaaacaaca                  2754
catgtaaatt gcttttttaac agctgatact ataataagac aaagccaaaa tgcaaaaatt                 2814
gggctttgat tggcactttt tgaaaaatat gcaacaaata tgggatgtaa tctggatggc                  2874
cgcttctgta cttaatgtga agtatttaga tacctttttg aacacttaac agtttcttct                  2934
gacaatgact tttgtaagga ttggtactat ctatcattcc ttataatgta cattgtctgt                  2994
cactaatcct cagatcttgc tgtattgtca cctaaattgg tacaggtact gatgaaaata                  3054
tctaatggat aatcataaca ctcttggtca catgttttc ctgcagcctg aaggtttta                    3114 aaagaaaaag atatcaaatg cctgctgcta ccacccttt aaattgctat cttttgaaaa                   3174
gcaccagtat gtgttttaga ttgatttccc tattttaggg aaatgacaga cagtagtttc                  3234
agttctgatg gtataagcaa aacaaataaa acatgtttat aaaagttgta tcttgaaaca                  3294
ctggtgttca acagctagca gcttatgtgg ttcaccccat gcattgttag tgtttcagat                  3354
tttatggtta tctccagcag ctgtttctgt agtacttgca tttatctttt gtctaaccct                  3414
aatattctca cggaggcatt tatattcaaa gtggtgatcc cttcacttag acgcataggg                  3474
```

```
agagtcacaa gtttgatgaa gaggacagtg tagtaattta tatgctgttg gaatttgtgc    3534
tagcagtttg agcactagtt ctgtgtgcct atgaacttaa tgctgcttgt catattccac    3594
tttgacttca tggagaatta atcccatcta ctcagcaaag gctatactaa tactaagtta    3654
atggtatttt ctgtgcagaa attgaatttt gttttattag catttagcta aggaattttt    3714
ccagtaggtg ctcagctact aaagaaaaac aaaaacaaga cacaaaacta ttctcaaaca    3774
ttcattgtta gacaactgga gttttgctg gttttgtaac ctactaaaat ggataggctg     3834
ttgaacattc cacattcaaa agttttttgt agggtggtgg ggaagggggg gtgtcttcaa    3894
tgtttatttt aaaataaaat aagttcttga ctttttctcat gtgtggttgt ggtacatcat   3954
attggaaggg ttatctgttt acttttgcaa atgagtattt ctcttgctag cacctcccgt    4014
tgtgcgcttt aaatgacatc tgcctgggat gtaccacaac catatgttag ctgtatttta    4074
tggggaatag ataaaatatt cgtggtttat tgggtaatcc ctagatgtgt atgcttacaa    4134
tcctatatat aaaactaaat                                                4154

<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255
```

```
Thr His Asn His Gln Asn Gly Leu Cys Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
            405                 410                 415

Pro Pro Val His Ser Glu Ser Arg Leu Ala Gln Pro Asn Gln Val Pro
        420                 425                 430

Val Gln Pro Glu Ala Thr Gln Val Pro Leu Val Ser Ser Thr Ser Glu
    435                 440                 445

Gly Tyr Thr Ala Ser Gln Pro Leu Tyr Gln Pro Ser His Ala Thr Glu
450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
            485                 490                 495

Gln Pro Gln Val Phe Gln Ala Gly Thr Ser Lys Pro Leu His Ser Ser
        500                 505                 510

Gly Ile Asn Val Asn Ala Ala Pro Phe Gln Ser Met Gln Thr Val Phe
    515                 520                 525

Asn Met Asn Ala Pro Val Pro Pro Val Asn Glu Pro Glu Thr Leu Lys
530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Leu Gln Thr
            565                 570                 575

Val Val Gly Thr Tyr His Gly Ser Gln Asp Gln Pro His Gln Val Thr
        580                 585                 590

Gly Asn His Gln Gln Pro Pro Gln Gln Asn Thr Gly Phe Pro Arg Ser
    595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
            645                 650                 655

Ser Gly Tyr Thr Gln Ser Gln Phe Ser Ala Pro Arg Asp Tyr Ser Gly
        660                 665                 670
```

```
Tyr Gln Arg Asp Gly Tyr Gln Gln Asn Phe Lys Arg Ser Gly Gln
            675                 680                 685

Ser Gly Pro Arg Gly Ala Pro Arg Gly Arg Gly Pro Pro Arg Pro
        690                 695                 700

Asn Arg Gly Met Pro Gln Met Asn Thr Gln Gln Val Asn
705                 710                 715

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
            35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
        50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat     336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt     384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt     432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc     480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg     528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg     576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc     624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac     672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca     720
Leu Leu Glu Gly Lys Glu Lys Ser Val Cys Gly Thr Thr Tyr Lys Ala
225                 230                 235                 240
```

| | | |
|---|---|---|
| cta aag gaa att gtt gag cgt gtt ttc cag tca aat tac ttt gac agc | 768 | |
| Leu Lys Glu Ile Val Glu Arg Val Phe Gln Ser Asn Tyr Phe Asp Ser | | |
|     245             250             255 | | |
| act cac aac cac cag aat ggg cta tgt gag gaa gaa gag gca gcc tca | 816 | |
| Thr His Asn His Gln Asn Gly Leu Cys Glu Glu Glu Glu Ala Ala Ser | | |
| 260             265             270 | | |
| gca cct aca gtt gaa gac cag gta gct gaa gct gag cct gag cca gca | 864 | |
| Ala Pro Thr Val Glu Asp Gln Val Ala Glu Ala Glu Pro Glu Pro Ala | | |
|     275             280             285 | | |
| gaa gaa tac act gaa caa agt gaa gtt gaa tca aca gag tat gta aat | 912 | |
| Glu Glu Tyr Thr Glu Gln Ser Glu Val Glu Ser Thr Glu Tyr Val Asn | | |
| 290             295             300 | | |
| aga caa ttt atg gca gaa aca cag ttc agc agt ggt gaa aag gag cag | 960 | |
| Arg Gln Phe Met Ala Glu Thr Gln Phe Ser Ser Gly Glu Lys Glu Gln | | |
| 305             310             315             320 | | |
| gta gat gag tgg acg gtc gaa aca gtg gag gtg gtg aat tca ctc cag | 1008 | |
| Val Asp Glu Trp Thr Val Glu Thr Val Glu Val Val Asn Ser Leu Gln | | |
|     325             330             335 | | |
| cag caa cct cag gct gcg tct cct tca gta cca gag ccc cac tct ttg | 1056 | |
| Gln Gln Pro Gln Ala Ala Ser Pro Ser Val Pro Glu Pro His Ser Leu | | |
| 340             345             350 | | |
| act ccg gtg gct cag gca gat ccc ctt gtg aga aga cag cga gtc cag | 1104 | |
| Thr Pro Val Ala Gln Ala Asp Pro Leu Val Arg Arg Gln Arg Val Gln | | |
|     355             360             365 | | |
| gac ctt atg gcg cag atg cag ggg ccc tat aat ttc ata cag gat tca | 1152 | |
| Asp Leu Met Ala Gln Met Gln Gly Pro Tyr Asn Phe Ile Gln Asp Ser | | |
| 370             375             380 | | |
| atg ctg gat ttt gaa aac cag aca ctc gat cct gcc att gta tct gca | 1200 | |
| Met Leu Asp Phe Glu Asn Gln Thr Leu Asp Pro Ala Ile Val Ser Ala | | |
| 385             390             395             400 | | |
| cag cct atg aat ccg aca caa aac atg gac atg ccc cag ctg gtt tgc | 1248 | |
| Gln Pro Met Asn Pro Thr Gln Asn Met Asp Met Pro Gln Leu Val Cys | | |
|     405             410             415 | | |
| cct cca gtt cat tct gaa tct aga ctt gct caa cct aat caa gtt cct | 1296 | |
| Pro Pro Val His Ser Glu Ser Arg Leu Ala Gln Pro Asn Gln Val Pro | | |
| 420             425             430 | | |
| gta caa cca gaa gct aca cag gtt cct ttg gtt tca tcc aca agt gag | 1344 | |
| Val Gln Pro Glu Ala Thr Gln Val Pro Leu Val Ser Ser Thr Ser Glu | | |
|     435             440             445 | | |
| ggg tat aca gca tct caa ccc ttg tac cag cct tct cat gct aca gag | 1392 | |
| Gly Tyr Thr Ala Ser Gln Pro Leu Tyr Gln Pro Ser His Ala Thr Glu | | |
| 450             455             460 | | |
| caa cga cca caa aag gaa cca att gac cag att cag gca aca atc tct | 1440 | |
| Gln Arg Pro Gln Lys Glu Pro Ile Asp Gln Ile Gln Ala Thr Ile Ser | | |
| 465             470             475             480 | | |
| tta aat aca gac cag act aca gcg tca tca tcc ctt ccg gct gct tct | 1488 | |
| Leu Asn Thr Asp Gln Thr Thr Ala Ser Ser Ser Leu Pro Ala Ala Ser | | |
|     485             490             495 | | |
| cag cct cag gta ttc cag gct ggg aca agc aaa cca tta cat agc agt | 1536 | |
| Gln Pro Gln Val Phe Gln Ala Gly Thr Ser Lys Pro Leu His Ser Ser | | |
| 500             505             510 | | |
| gga atc aat gta aat gca gct cca ttc caa tcc atg caa acg gtg ttc | 1584 | |
| Gly Ile Asn Val Asn Ala Ala Pro Phe Gln Ser Met Gln Thr Val Phe | | |
|     515             520             525 | | |
| aat atg aat gcc cca gtt cct cct gtt aat gaa cca gaa act ttg aaa | 1632 | |
| Asn Met Asn Ala Pro Val Pro Pro Val Asn Glu Pro Glu Thr Leu Lys | | |
| 530             535             540 | | |
| caa caa aat cag tac cag gcc agt tat aac cag agc ttt tct agt cag | 1680 | |
| Gln Gln Asn Gln Tyr Gln Ala Ser Tyr Asn Gln Ser Phe Ser Ser Gln | | |

```
                                                              -continued
545                 550                 555                 560 cct cac caa gta gaa caa aca gac ctt cag caa gaa cag ctt caa aca          1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act          1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc          1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt          1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc          1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac          1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc          2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag          2064
Tyr Gln Arg Asp Gly Tyr Gln Gln Asn Phe Lys Arg Gly Ser Gly Gln
        675                 680                 685 agt gga cca cgg gga gcc cca cga ggt aat att ttg tgg tgg tga              2109
Ser Gly Pro Arg Gly Ala Pro Arg Gly Asn Ile Leu Trp Trp
    690                 695                 700 tcctagctcc taagtggagc ttctgttctg gccttggaag agctgttcca tagtctgcat        2169
gtaggttaca tgttaggaat acatttatca ttaccagact tgttgctagg gattaaatga        2229
aatgctctgt ttctaaaact tctcttgaac ccaaatttaa ttttttgaat gactttccct        2289
gttactatat aaattgtctt gaaaactaga acatttctcc tcctcagaaa aagtgttttt        2349
ccaactgcaa attatttttc aggtcctaaa acctgctaaa tgttttagg aagtacttac         2409 tgaaacattt ttgtaagaca ttttggaat gagattgaac atttatataa atttattatt         2469
attcctcttt cattttgaa catgcatatt atatttagg gtcagaaatc ctttaatggc          2529
caaataagcc atagttacat ttagagaacc atttagaagt gatagaacta actgaaattt        2589
caatgccttt ggatcattaa tagcgatata aatttcaaat tgtttctgac ttttaaataa        2649
aacatccaaa atcctaacta acttcctgaa ctatatttaa aaattacagg tttaaggagt        2709
ttctggtttt ttttctctta ccataggaaa actgtttcct gtttggccag gaagtcaacc        2769
tgtgtaataa ttagaagtag catttcatat gatctgaagt tctaaatggt tctctgattt        2829
aagggaagtt aaattgaata ggtttcctct agttattggc cataacatgt ataaaatgta        2889
tattaaggag gaatacaaag tactttgatt tcaatgctag tagaaactgg ccagcaaaaa        2949
ggtgcatttt attttaaat taatggatca ctttgggaatt actgacttga agtatcaaag        3009
gatatttgca tgtgaatgtg ggttatgttc tttctcacct tgtagcatat tctatgaaag        3069
ttgagttgac tggtagctaa aaatctgttt taacagcatg taaaaagtta ttttatctgt        3129
tacaagtcat tatacaattt tgaatgttat gtagtttctt tttaacagtt taggtaacaa        3189
ggtctgtttt tcattctggt gcttttatta attttgatag tatgatgtta cttactactg        3249
aaatgtaagc tagagtgtac actagaatgt aagctccatg agagcaggta ccttgtctgt        3309
cttcactgct gtatctattt ccaacgcctg atgacagtgc ctgacacata gtaggcactc        3369
```

```
aataaatact tgttgaatga atgaatgaat gagtactggt ggaatactcc attagctcta    3429
ctcttctttt agctagagaa catgagcaaa tttgcgcatg acaacttcca ggacaggtga    3489
acactgaaga attgacctct taaacctaat aatgtggtga caagctgccc acatgcttct    3549
tgacttcaga tgaaaatctg cttgaaggca agcaaataa tatttgaaag aaaaaccaaa    3609
tgccattttt gtcttctagg tcgtggaggg cccccaagac ccaacagagg gatgccgcaa    3669
atgaacactc agcaagtgaa ttaatctgat tcacaggatt atgtttaaac gccaaaaaca    3729
cactggccag tgtaccataa tatgttacca gaagagttat tatctatttg ttctcccttt    3789
caggaaactt attgtaaagg gactgttttc atcccataaa gacaggacta caattgtcag    3849
ctttatatta cctggatatg aaggaaact attttttatc tgcatgttct tcctaagcgt    3909
catcttgagc cttgcacatg atactcagat tcctcaccct tgcttaggag taaaacataa    3969
tacactttac agggtgatat ctccatagtt atttgaagtg gcttggaaaa agcaagatta    4029
acttctgaca ttggataaaa atcaacaaat cagccctaga gttattcaaa tggtaattga    4089
caaaaactaa atatttccc ttcgagaagg agtggaatgt ggtttggcag aacaactgca    4149
tttcacagct tttccggtta aattggagca ctaaacgttt agatgcatac caaattatgc    4209
atgggccctt aatataaaag gctggctacc agctttgaca cagcactatt catcctctgg    4269
ccaaacaact gtggttaaac aacacatgta aattgctttt taacagctga tactataata    4329
agacaaagcc aaaatgcaaa aattgggctt tgattggcac ttttttgaaaa atatgcaaca    4389 aatatgggat gtaatctgga tggccgcttc tgtacttaat gtgaagtatt tagataccttt    4449 tttgaacact taacagtttc ttctgacaat gactttgta aggattggta ctatctatca    4509
ttccttataa tgtacattgt ctgtcactaa tcctcagatc ttgctgtatt gtcacctaaa    4569
ttggtacagg tactgatgaa aatatctaat ggataatcat aacactcttg gtcacatgtt    4629
tttcctgcag cctgaaggtt tttaaaagaa aaagatatca aatgcctgct gctaccaccc    4689
ttttaaattg ctatcttttg aaaagcacca gtatgtgttt tagattgatt tccctatttt    4749
agggaaatga cagacagtag tttcagttct gatggtataa gcaaaacaaa taaaacatgt    4809
ttataaaagt tgtatcttga aacactggtg ttcaacagct agcagcttat gtggttcacc    4869
ccatgcattg ttagtgtttc agattttatg gttatctcca gcagctgttt ctgtagtact    4929
tgcatttatc                                                          4939

<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
```

```
            85                  90                  95
Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
            115                 120                 125

Gln Asp Ile Gln Lys Thr Ile Lys Lys Thr Ala Arg Arg Glu Gln Leu
            130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Glu Val Arg Thr Asp Leu
                165                 170                 175

Lys Gln Gly Leu Asn Gly Val Pro Ile Leu Ser Glu Glu Leu Ser
                180                 185                 190

Leu Leu Asp Glu Phe Tyr Lys Leu Ala Asp Pro Glu Arg Asp Met Ser
            195                 200                 205

Leu Arg Leu Asn Glu Gln Tyr Glu His Ala Ser Ile His Leu Trp Asp
            210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                260                 265                 270

Ala Pro Thr Val Glu Asp Gln Val Ala Glu Ala Glu Pro Glu Pro Ala
            275                 280                 285

Glu Glu Tyr Thr Glu Gln Ser Glu Val Glu Ser Thr Glu Tyr Val Asn
            290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
            370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
            405                 410                 415

Pro Pro Val His Ser Glu Ser Arg Leu Ala Gln Pro Asn Gln Val Pro
                420                 425                 430

Val Gln Pro Glu Ala Thr Gln Val Pro Leu Val Ser Ser Thr Ser Glu
            435                 440                 445

Gly Tyr Thr Ala Ser Gln Pro Leu Tyr Gln Pro Ser His Ala Thr Glu
            450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
                485                 490                 495

Gln Pro Gln Val Phe Gln Ala Gly Thr Ser Lys Pro Leu His Ser Ser
            500                 505                 510
```

```
Gly Ile Asn Val Asn Ala Ala Pro Phe Gln Ser Met Gln Thr Val Phe
            515                 520                 525

Asn Met Asn Ala Pro Val Pro Pro Val Asn Glu Pro Glu Thr Leu Lys
        530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
690                 695                 700

<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)

<400> SEQUENCE: 11 atg ccg tcg gcc acc agc ctc agc gga agc ggc agc aag tcg tcg ggc    48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg    96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag   144
Gly Ala Ala Gly Ala Ala Gly Ala Gly Ala Ala Ala Pro Ala Ser Gln
        35                  40                  45 cac ccc gcg acc ggc acc ggc gct gtc cag acc gag gcc atg aag cag   192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag   240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt   288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat   336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt   384
Asn Leu Glu Phe Ala Lys Glu Leu Gln Arg Ser Phe Met Ala Leu Ser
        115                 120                 125
```

| | | | | | | | | | | | | | | | | |
|---|---|---|---|---|---|---|---|---|---|---|---|---|---|---|---|---|
| caa | gat | att | cag | aaa | aca | ata | aag | aag | act | gca | cgt | cgg | gag | cag | ctt | 432 |
| Gln | Asp | Ile | Gln | Lys | Thr | Ile | Lys | Lys | Thr | Ala | Arg | Arg | Glu | Gln | Leu | |
| | | 130 | | | | 135 | | | | 140 | | | | | | |
| atg | aga | gag | gaa | gcg | gaa | caa | aaa | cgt | tta | aaa | act | gta | ctt | gag | ctc | 480 |
| Met | Arg | Glu | Glu | Ala | Glu | Gln | Lys | Arg | Leu | Lys | Thr | Val | Leu | Glu | Leu | |
| 145 | | | | | 150 | | | | | 155 | | | | | 160 | |
| cag | tat | gtt | ttg | gac | aaa | ttg | gga | gat | gat | gaa | gtg | aga | act | gac | ctg | 528 |
| Gln | Tyr | Val | Leu | Asp | Lys | Leu | Gly | Asp | Asp | Glu | Val | Arg | Thr | Asp | Leu | |
| | | | | 165 | | | | | 170 | | | | | 175 | | |
| aag | caa | ggt | ttg | aat | gga | gtg | cca | ata | ttg | tct | gaa | gaa | gaa | ttg | tcg | 576 |
| Lys | Gln | Gly | Leu | Asn | Gly | Val | Pro | Ile | Leu | Ser | Glu | Glu | Glu | Leu | Ser | |
| | | | 180 | | | | | 185 | | | | | 190 | | | |
| ttg | ttg | gat | gaa | ttc | tac | aaa | tta | gca | gac | cct | gaa | cgg | gac | atg | agc | 624 |
| Leu | Leu | Asp | Glu | Phe | Tyr | Lys | Leu | Ala | Asp | Pro | Glu | Arg | Asp | Met | Ser | |
| | | | 195 | | | | | 200 | | | | | 205 | | | |
| ttg | agg | ttg | aat | gag | cag | tat | gaa | cat | gct | tcc | att | cac | ctg | tgg | gac | 672 |
| Leu | Arg | Leu | Asn | Glu | Gln | Tyr | Glu | His | Ala | Ser | Ile | His | Leu | Trp | Asp | |
| | | 210 | | | | | 215 | | | | | 220 | | | | |
| ttg | ctg | gaa | gga | aag | gaa | aag | tct | gta | tgt | gga | aca | acc | tat | aaa | gca | 720 |
| Leu | Leu | Glu | Gly | Lys | Glu | Lys | Ser | Val | Cys | Gly | Thr | Thr | Tyr | Lys | Ala | |
| 225 | | | | | 230 | | | | | 235 | | | | | 240 | |
| cta | aag | gaa | att | gtt | gag | cgt | gtt | ttc | cag | tca | aat | tac | ttt | gac | agc | 768 |
| Leu | Lys | Glu | Ile | Val | Glu | Arg | Val | Phe | Gln | Ser | Asn | Tyr | Phe | Asp | Ser | |
| | | | | 245 | | | | | 250 | | | | | 255 | | |
| act | cac | aac | cac | cag | aat | ggg | cta | tgt | gag | gaa | gaa | gag | gca | gcc | tca | 816 |
| Thr | His | Asn | His | Gln | Asn | Gly | Leu | Cys | Glu | Glu | Glu | Glu | Ala | Ala | Ser | |
| | | | 260 | | | | | 265 | | | | | 270 | | | |
| gca | cct | aca | gtt | gaa | gac | cag | gta | gct | gaa | gct | gag | cct | gag | cca | gca | 864 |
| Ala | Pro | Thr | Val | Glu | Asp | Gln | Val | Ala | Glu | Ala | Glu | Pro | Glu | Pro | Ala | |
| | | 275 | | | | | 280 | | | | | 285 | | | | |
| gaa | gaa | tac | act | gaa | caa | agt | gaa | gtt | gaa | tca | aca | gag | tat | gta | aat | 912 |
| Glu | Glu | Tyr | Thr | Glu | Gln | Ser | Glu | Val | Glu | Ser | Thr | Glu | Tyr | Val | Asn | |
| | 290 | | | | | 295 | | | | | 300 | | | | | |
| aga | caa | ttt | atg | gca | gaa | aca | cag | ttc | agc | agt | ggt | gaa | aag | gag | cag | 960 |
| Arg | Gln | Phe | Met | Ala | Glu | Thr | Gln | Phe | Ser | Ser | Gly | Glu | Lys | Glu | Gln | |
| 305 | | | | | 310 | | | | | 315 | | | | | 320 | |
| gta | gat | gag | tgg | acg | gtc | gaa | aca | gtg | gag | gtg | gtg | aat | tca | ctc | cag | 1008 |
| Val | Asp | Glu | Trp | Thr | Val | Glu | Thr | Val | Glu | Val | Val | Asn | Ser | Leu | Gln | |
| | | | | 325 | | | | | 330 | | | | | 335 | | |
| cag | caa | cct | cag | gct | gcg | tct | cct | tca | gta | cca | gag | ccc | cac | tct | ttg | 1056 |
| Gln | Gln | Pro | Gln | Ala | Ala | Ser | Pro | Ser | Val | Pro | Glu | Pro | His | Ser | Leu | |
| | | | 340 | | | | | 345 | | | | | 350 | | | |
| act | ccg | gtg | gct | cag | gca | gat | ccc | ctt | gtg | aga | aga | cag | cga | gtc | cag | 1104 |
| Thr | Pro | Val | Ala | Gln | Ala | Asp | Pro | Leu | Val | Arg | Arg | Gln | Arg | Val | Gln | |
| | | | 355 | | | | | 360 | | | | | 365 | | | |
| gac | ctt | atg | gcg | cag | atg | cag | ggg | ccc | tat | aat | ttc | ata | cag | gat | tca | 1152 |
| Asp | Leu | Met | Ala | Gln | Met | Gln | Gly | Pro | Tyr | Asn | Phe | Ile | Gln | Asp | Ser | |
| | 370 | | | | | 375 | | | | | 380 | | | | | |
| atg | ctg | gat | ttt | gaa | aac | cag | aca | ctc | gat | cct | gcc | att | gta | tct | gca | 1200 |
| Met | Leu | Asp | Phe | Glu | Asn | Gln | Thr | Leu | Asp | Pro | Ala | Ile | Val | Ser | Ala | |
| 385 | | | | | 390 | | | | | 395 | | | | | 400 | |
| cag | cct | atg | aat | ccg | aca | caa | aac | atg | gac | atg | ccc | cag | ctg | gtt | tgc | 1248 |
| Gln | Pro | Met | Asn | Pro | Thr | Gln | Asn | Met | Asp | Met | Pro | Gln | Leu | Val | Cys | |
| | | | | 405 | | | | | 410 | | | | | 415 | | |
| cct | cca | gtt | cat | tct | gaa | tct | aga | ctt | gct | caa | cct | aat | caa | gtt | cct | 1296 |
| Pro | Pro | Val | His | Ser | Glu | Ser | Arg | Leu | Ala | Gln | Pro | Asn | Gln | Val | Pro | |
| | | | 420 | | | | | 425 | | | | | 430 | | | |
| gta | caa | cca | gaa | gct | aca | cag | gtt | cct | ttg | gtt | tca | tcc | aca | agt | gag | 1344 |
| Val | Gln | Pro | Glu | Ala | Thr | Gln | Val | Pro | Leu | Val | Ser | Ser | Thr | Ser | Glu | |

|  |  |  |  |  |  |  |  |  |  |  |  |  |  |  |  |
|---|---|---|---|---|---|---|---|---|---|---|---|---|---|---|---|
|  |  | 435 |  |  |  | 440 |  |  |  | 445 |  |  |  |  |  |
| ggg | tat | aca | gca | tct | caa | ccc | ttg | tac | cag | cct | tct | cat | gct | aca | gag | 1392 |
| Gly | Tyr | Thr | Ala | Ser | Gln | Pro | Leu | Tyr | Gln | Pro | Ser | His | Ala | Thr | Glu |  |
|  | 450 |  |  |  |  | 455 |  |  |  |  | 460 |  |  |  |  |  |
| caa | cga | cca | caa | aag | gaa | cca | att | gac | cag | att | cag | gca | aca | atc | tct | 1440 |
| Gln | Arg | Pro | Gln | Lys | Glu | Pro | Ile | Asp | Gln | Ile | Gln | Ala | Thr | Ile | Ser |  |
| 465 |  |  |  |  | 470 |  |  |  |  | 475 |  |  |  |  | 480 |  |
| tta | aat | aca | gac | cag | act | aca | gcg | tca | tca | tcc | ctt | ccg | gct | gct | tct | 1488 |
| Leu | Asn | Thr | Asp | Gln | Thr | Thr | Ala | Ser | Ser | Ser | Leu | Pro | Ala | Ala | Ser |  |
|  |  |  |  | 485 |  |  |  |  | 490 |  |  |  |  | 495 |  |  |
| cag | cct | cag | gta | ttc | cag | gct | ggg | aca | agc | aaa | cca | tta | cat | agc | agt | 1536 |
| Gln | Pro | Gln | Val | Phe | Gln | Ala | Gly | Thr | Ser | Lys | Pro | Leu | His | Ser | Ser |  |
|  |  |  | 500 |  |  |  |  | 505 |  |  |  |  | 510 |  |  |  |
| gga | atc | aat | gta | aat | gca | gct | cca | ttc | caa | tcc | atg | caa | acg | gtg | ttc | 1584 |
| Gly | Ile | Asn | Val | Asn | Ala | Ala | Pro | Phe | Gln | Ser | Met | Gln | Thr | Val | Phe |  |
|  |  | 515 |  |  |  |  | 520 |  |  |  |  | 525 |  |  |  |  |
| aat | atg | aat | gcc | cca | gtt | cct | cct | gtt | aat | gaa | cca | gaa | act | ttg | aaa | 1632 |
| Asn | Met | Asn | Ala | Pro | Val | Pro | Pro | Val | Asn | Glu | Pro | Glu | Thr | Leu | Lys |  |
|  | 530 |  |  |  |  | 535 |  |  |  |  | 540 |  |  |  |  |  |
| caa | caa | aat | cag | tac | cag | gcc | agt | tat | aac | cag | agc | ttt | tct | agt | cag | 1680 |
| Gln | Gln | Asn | Gln | Tyr | Gln | Ala | Ser | Tyr | Asn | Gln | Ser | Phe | Ser | Ser | Gln |  |
| 545 |  |  |  |  | 550 |  |  |  |  | 555 |  |  |  |  | 560 |  |
| cct | cac | caa | gta | gaa | caa | aca | gac | ctt | cag | caa | gaa | cag | ctt | caa | aca | 1728 |
| Pro | His | Gln | Val | Glu | Gln | Thr | Asp | Leu | Gln | Gln | Glu | Gln | Leu | Gln | Thr |  |
|  |  |  |  | 565 |  |  |  |  | 570 |  |  |  |  | 575 |  |  |
| gtg | gtt | ggc | act | tac | cat | ggt | tcc | cag | gac | cag | ccc | cac | caa | gtg | act | 1776 |
| Val | Val | Gly | Thr | Tyr | His | Gly | Ser | Gln | Asp | Gln | Pro | His | Gln | Val | Thr |  |
|  |  |  | 580 |  |  |  |  | 585 |  |  |  |  | 590 |  |  |  |
| ggt | aac | cat | cag | cag | cct | ccc | cag | cag | aac | act | gga | ttt | cca | cgt | agc | 1824 |
| Gly | Asn | His | Gln | Gln | Pro | Pro | Gln | Gln | Asn | Thr | Gly | Phe | Pro | Arg | Ser |  |
|  |  | 595 |  |  |  |  | 600 |  |  |  |  | 605 |  |  |  |  |
| agt | cag | ccc | tat | tac | aat | agt | cgt | ggt | gtg | tct | cgt | ggt | ggt | tcc | cgt | 1872 |
| Ser | Gln | Pro | Tyr | Tyr | Asn | Ser | Arg | Gly | Val | Ser | Arg | Gly | Gly | Ser | Arg |  |
|  | 610 |  |  |  |  | 615 |  |  |  |  | 620 |  |  |  |  |  |
| ggt | gct | aga | ggc | tta | atg | aat | gga | tac | agg | ggc | cct | gcc | aat | gga | ttc | 1920 |
| Gly | Ala | Arg | Gly | Leu | Met | Asn | Gly | Tyr | Arg | Gly | Pro | Ala | Asn | Gly | Phe |  |
| 625 |  |  |  |  | 630 |  |  |  |  | 635 |  |  |  |  | 640 |  |
| aga | gga | gga | tat | gat | ggt | tac | cgc | cct | tca | ttc | tct | aac | act | cca | aac | 1968 |
| Arg | Gly | Gly | Tyr | Asp | Gly | Tyr | Arg | Pro | Ser | Phe | Ser | Asn | Thr | Pro | Asn |  |
|  |  |  |  | 645 |  |  |  |  | 650 |  |  |  |  | 655 |  |  |
| agt | ggt | tat | aca | cag | tct | cag | ttc | agt | gct | ccc | cgg | gac | tac | tct | ggc | 2016 |
| Ser | Gly | Tyr | Thr | Gln | Ser | Gln | Phe | Ser | Ala | Pro | Arg | Asp | Tyr | Ser | Gly |  |
|  |  |  | 660 |  |  |  |  | 665 |  |  |  |  | 670 |  |  |  |
| tat | cag | cgg | gga | tgc | cgc | aaa | tga | acactcagca | agtgaattaa | tctgattcac |  |  |  |  |  | 2070 |
| Tyr | Gln | Arg | Gly | Cys | Arg | Lys |  |  |  |  |  |  |  |  |  |  |
|  | 675 |  |  |  |  |  |  |  |  |  |  |  |  |  |  |  | aggattatgt ttaaacgcca aaaacacact ggccagtgta ccataatatg ttaccagaag 2130 agttattatc tatttgttct cccctttcagg aaacttattg taaagggact gttttcatcc 2190 cataaagaca ggactacaat tgtcagcttt atattacctg gatatggaag gaaactattt 2250 ttattctgca tgttcttcct aagcgtcatc ttgagccttg cacatgatac tcagattcct 2310 cacccttgct taggagtaaa acataataca ctttacaggg tgtatctcc atagttattt 2370 gaagtggctt ggaaaaagca agattaactt ctgacattgg ataaaatca acaaatcagc 2430 cctagagtta ttcaaatggt aattgacaaa aactaaaata tttcccttcg agaaggagtg 2490 gaatgtggtt tggcagaaca actgcatttc acagcttttc cggttaaatt ggagcactaa 2550 acgtttagat gcataccaaa ttatgcatgg gcccttaata taaaaggctg gctaccagct 2610

-continued

```
ttgacacagc actattcatc ctctggccaa acaactgtgg ttaaacaaca catgtaaatt    2670 gcttttaac agctgatact ataataagac aaagccaaaa tgcaaaaatt gggctttgat    2730
tggcactttt tgaaaaatat gcaacaaata tgggatgtaa tctggatggc cgcttctgta    2790
cttaatgtga agtatttaga tacctttttg aacacttaac agtttcttct gacaatgact    2850
tttgtaagga ttggtactat ctatcattcc ttataatgta cattgtctgt cactaatcct    2910
cagatcttgc tgtattgtca cctaaattgg tacaggtact gatgaaaata tctaatggat    2970
aatcataaca ctcttggtca catgttttc ctgcagcctg aaggttttta aagaaaaag     3030 atatcaaatg cctgctgcta ccacccttt aaattgctat cttttgaaaa gcaccagtat    3090
gtgttttaga ttgatttccc tattttaggg aaatgacaga cagtagtttc agttctgatg    3150
gtataagcaa acaaataaa acatgtttat aaaagttgta tcttgaaaca ctggtgttca    3210
acagctagca gcttatgtgg ttcaccccat gcattgttag tgtttcagat tttatggtta    3270
tctccagcag ctgtttctgt agtacttgca tttatc                            3306
```

<210> SEQ ID NO 12
<211> LENGTH: 679
<212> TYPE: PRT
<213> ORGANISM: Canis familiaris

<400> SEQUENCE: 12

```
Met Pro Ser Ala Thr Ser Leu Ser Gly Ser Gly Ser Lys Ser Gly
1               5                   10                  15

Pro Pro Pro Pro Ser Gly Ser Ser Gly Ser Glu Ala Ala Ala Ala
            20                  25                  30

Gly Ala Ala Gly Ala Ala Gly Ala Gly Ala Ala Pro Ala Ser Gln
            35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
```

```
                245                 250                 255
Thr His Asn His Gln Asn Gly Leu Cys Glu Glu Glu Ala Ala Ser
            260                 265                 270
Ala Pro Thr Val Glu Asp Gln Val Ala Glu Glu Pro Glu Pro Ala
            275                 280                 285
Glu Glu Tyr Thr Glu Gln Ser Glu Val Glu Ser Thr Glu Tyr Val Asn
        290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Asn Ser Leu Gln
            325                 330                 335
Gln Gln Pro Gln Ala Ala Ser Pro Ser Val Pro Glu Pro His Ser Leu
        340                 345                 350
Thr Pro Val Ala Gln Ala Asp Pro Leu Val Arg Arg Gln Arg Val Gln
            355                 360                 365
Asp Leu Met Ala Gln Met Gln Gly Pro Tyr Asn Phe Ile Gln Asp Ser
        370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
            405                 410                 415
Pro Pro Val His Ser Glu Ser Arg Leu Ala Gln Pro Asn Gln Val Pro
            420                 425                 430
Val Gln Pro Glu Ala Thr Gln Val Pro Leu Val Ser Ser Thr Ser Glu
            435                 440                 445
Gly Tyr Thr Ala Ser Gln Pro Leu Tyr Gln Pro Ser His Ala Thr Glu
        450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Leu Pro Ala Ala Ser
            485                 490                 495
Gln Pro Gln Val Phe Gln Ala Gly Thr Ser Lys Pro Leu His Ser Ser
        500                 505                 510
Gly Ile Asn Val Asn Ala Ala Pro Phe Gln Ser Met Gln Thr Val Phe
        515                 520                 525
Asn Met Asn Ala Pro Val Pro Pro Val Asn Glu Pro Glu Thr Leu Lys
        530                 535                 540
Gln Gln Asn Gln Tyr Gln Ala Ser Tyr Asn Gln Ser Phe Ser Ser Gln
545                 550                 555                 560
Pro His Gln Val Glu Gln Thr Asp Leu Gln Gln Glu Gln Leu Gln Thr
            565                 570                 575
Val Val Gly Thr Tyr His Gly Ser Gln Asp Gln Pro His Gln Val Thr
            580                 585                 590
Gly Asn His Gln Gln Pro Pro Gln Gln Asn Thr Gly Phe Pro Arg Ser
            595                 600                 605
Ser Gln Pro Tyr Tyr Asn Ser Arg Gly Val Ser Arg Gly Gly Ser Arg
            610                 615                 620
Gly Ala Arg Gly Leu Met Asn Gly Tyr Arg Gly Pro Ala Asn Gly Phe
625                 630                 635                 640
Arg Gly Gly Tyr Asp Gly Tyr Arg Pro Ser Phe Ser Asn Thr Pro Asn
            645                 650                 655
Ser Gly Tyr Thr Gln Ser Gln Phe Ser Ala Pro Arg Asp Tyr Ser Gly
        660                 665                 670
```

```
Tyr Gln Arg Gly Cys Arg Lys
        675

<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13 atg ccg tcg gcc acc agc ctc agc gga agc ggc agc aag tcg tcg ggc     48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg     96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag    144
Gly Ala Ala Gly Ala Ala Gly Ala Gly Ala Ala Ala Pro Ala Ser Gln
        35                  40                  45 cac ccc gcg acc ggc acc ggc gct gtc cag acc gag gcc atg aag cag    192
His Pro Ala Thr Gly Thr Gly Ala Val Gln Thr Glu Ala Met Lys Gln
 50                  55                  60 atc ctc ggg gtg atc gac aag aaa ctc cgg aac ctg gag aag aaa aag    240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt    288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat    336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt    384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt    432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc    480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg    528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg    576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc    624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac    672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca    720
Leu Leu Glu Gly Lys Glu Lys Ser Val Cys Gly Thr Thr Tyr Lys Ala
225                 230                 235                 240 cta aag gaa att gtt gag cgt gtt ttc agt tca aat tac ttt gac agc    768
Leu Lys Glu Ile Val Glu Arg Val Phe Gln Ser Asn Tyr Phe Asp Ser
                245                 250                 255
```

| | | | | | | | | | | | | | | | | |
|---|---|---|---|---|---|---|---|---|---|---|---|---|---|---|---|---|
| act | cac | aac | cac | cag | aat | ggg | cta | tgt | gag | gaa | gaa | gag | gca | gcc | tca | 816 |
| Thr | His | Asn | His | Gln | Asn | Gly | Leu | Cys | Glu | Glu | Glu | Glu | Ala | Ala | Ser | |
| | | 260 | | | | | 265 | | | | | 270 | | | | |
| gca | cct | aca | gtt | gaa | gac | cag | gta | gct | gaa | gct | gag | cct | gag | cca | gca | 864 |
| Ala | Pro | Thr | Val | Glu | Asp | Gln | Val | Ala | Glu | Ala | Glu | Pro | Glu | Pro | Ala | |
| | | 275 | | | | | 280 | | | | | 285 | | | | |
| gaa | gaa | tac | act | gaa | caa | agt | gaa | gtt | gaa | tca | aca | gag | tat | gta | aat | 912 |
| Glu | Glu | Tyr | Thr | Glu | Gln | Ser | Glu | Val | Glu | Ser | Thr | Glu | Tyr | Val | Asn | |
| | 290 | | | | | 295 | | | | | 300 | | | | | |
| aga | caa | ttt | atg | gca | gaa | aca | cag | ttc | agc | agt | ggt | gaa | aag | gag | cag | 960 |
| Arg | Gln | Phe | Met | Ala | Glu | Thr | Gln | Phe | Ser | Ser | Gly | Glu | Lys | Glu | Gln | |
| 305 | | | | | 310 | | | | | 315 | | | | | 320 | |
| gta | gat | gag | tgg | acg | gtc | gaa | aca | gtg | gag | gtg | gtg | aat | tca | ctc | cag | 1008 |
| Val | Asp | Glu | Trp | Thr | Val | Glu | Thr | Val | Glu | Val | Val | Asn | Ser | Leu | Gln | |
| | | | | 325 | | | | | 330 | | | | | 335 | | |
| cag | caa | cct | cag | gct | gcg | tct | cct | tca | gta | cca | gag | ccc | cac | tct | ttg | 1056 |
| Gln | Gln | Pro | Gln | Ala | Ala | Ser | Pro | Ser | Val | Pro | Glu | Pro | His | Ser | Leu | |
| | | | 340 | | | | | 345 | | | | | 350 | | | |
| act | ccg | gtg | gct | cag | gca | gat | ccc | ctt | gtg | aga | aga | cag | cga | gtc | cag | 1104 |
| Thr | Pro | Val | Ala | Gln | Ala | Asp | Pro | Leu | Val | Arg | Arg | Gln | Arg | Val | Gln | |
| | | | 355 | | | | | 360 | | | | | 365 | | | |
| gac | ctt | atg | gcg | cag | atg | cag | ggg | ccc | tat | aat | ttc | ata | cag | gat | tca | 1152 |
| Asp | Leu | Met | Ala | Gln | Met | Gln | Gly | Pro | Tyr | Asn | Phe | Ile | Gln | Asp | Ser | |
| 370 | | | | | 375 | | | | | 380 | | | | | | |
| atg | ctg | gat | ttt | gaa | aac | cag | aca | ctc | gat | cct | gcc | att | gta | tct | gca | 1200 |
| Met | Leu | Asp | Phe | Glu | Asn | Gln | Thr | Leu | Asp | Pro | Ala | Ile | Val | Ser | Ala | |
| 385 | | | | | 390 | | | | | 395 | | | | | 400 | |
| cag | cct | atg | aat | ccg | aca | caa | aac | atg | gac | atg | ccc | cag | ctg | gtt | tgc | 1248 |
| Gln | Pro | Met | Asn | Pro | Thr | Gln | Asn | Met | Asp | Met | Pro | Gln | Leu | Val | Cys | |
| | | | | 405 | | | | | 410 | | | | | 415 | | |
| cct | cca | gtt | cat | tct | gaa | tct | aga | ctt | gct | caa | cct | aat | caa | gtt | cct | 1296 |
| Pro | Pro | Val | His | Ser | Glu | Ser | Arg | Leu | Ala | Gln | Pro | Asn | Gln | Val | Pro | |
| | | | 420 | | | | | 425 | | | | | 430 | | | |
| gta | caa | cca | gaa | gct | aca | cag | gtt | cct | ttg | gtt | tca | tcc | aca | agt | gag | 1344 |
| Val | Gln | Pro | Glu | Ala | Thr | Gln | Val | Pro | Leu | Val | Ser | Ser | Thr | Ser | Glu | |
| | | | 435 | | | | | 440 | | | | | 445 | | | |
| ggg | tat | aca | gca | tct | caa | ccc | ttg | tac | cag | cct | tct | cat | gct | aca | gag | 1392 |
| Gly | Tyr | Thr | Ala | Ser | Gln | Pro | Leu | Tyr | Gln | Pro | Ser | His | Ala | Thr | Glu | |
| | 450 | | | | | 455 | | | | | 460 | | | | | |
| caa | cga | cca | caa | aag | gaa | cca | att | gac | cag | att | cag | gca | aca | atc | tct | 1440 |
| Gln | Arg | Pro | Gln | Lys | Glu | Pro | Ile | Asp | Gln | Ile | Gln | Ala | Thr | Ile | Ser | |
| 465 | | | | | 470 | | | | | 475 | | | | | 480 | |
| tta | aat | aca | gac | cag | act | aca | gcg | tca | tca | tcc | ctt | ccg | gct | gct | tct | 1488 |
| Leu | Asn | Thr | Asp | Gln | Thr | Thr | Ala | Ser | Ser | Ser | Leu | Pro | Ala | Ala | Ser | |
| | | | 485 | | | | | 490 | | | | | 495 | | | |
| cag | cct | cag | gta | ttc | cag | gct | ggg | aca | agc | aaa | cca | tta | cat | agc | agt | 1536 |
| Gln | Pro | Gln | Val | Phe | Gln | Ala | Gly | Thr | Ser | Lys | Pro | Leu | His | Ser | Ser | |
| | | | 500 | | | | | 505 | | | | | 510 | | | |
| gga | atc | aat | gta | aat | gca | gct | cca | ttc | caa | tcc | atg | caa | acg | gtg | ttc | 1584 |
| Gly | Ile | Asn | Val | Asn | Ala | Ala | Pro | Phe | Gln | Ser | Met | Gln | Thr | Val | Phe | |
| | | | 515 | | | | | 520 | | | | | 525 | | | |
| aat | atg | aat | gcc | cca | gtt | cct | cct | gtt | aat | gaa | cca | gaa | act | ttg | aaa | 1632 |
| Asn | Met | Asn | Ala | Pro | Val | Pro | Pro | Val | Asn | Glu | Pro | Glu | Thr | Leu | Lys | |
| | 530 | | | | | 535 | | | | | 540 | | | | | |
| caa | caa | aat | cag | tac | cag | gcc | agt | tat | aac | cag | agc | ttt | tct | agt | cag | 1680 |
| Gln | Gln | Asn | Gln | Tyr | Gln | Ala | Ser | Tyr | Asn | Gln | Ser | Phe | Ser | Ser | Gln | |
| 545 | | | | 550 | | | | | 555 | | | | | 560 | | |
| cct | cac | caa | gta | gaa | caa | aca | gac | ctt | cag | caa | gaa | cag | ctt | caa | aca | 1728 |
| Pro | His | Gln | Val | Glu | Gln | Thr | Asp | Leu | Gln | Gln | Glu | Gln | Leu | Gln | Thr | |
| | | | 565 | | | | | 570 | | | | | 575 | | | |

-continued

```
gtg gtt ggc act tac cat ggt tcc cag gac cag ccc cac caa gtg act    1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc    1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa            2154
Asn Arg Gly Met Pro Gln Met Asn Thr Gln Gln Val Asn
705                 710                 715 tctgattcac aggattatgt ttaaacgcca aaaacacact ggccagtgta ccataatatg  2214
ttaccagaag agttattatc tatttggact gttttcatcc cataaagaca ggactacaat  2274
tgtcagc                                                           2281
```

<210> SEQ ID NO 14
<211> LENGTH: 717
<212> TYPE: PRT
<213> ORGANISM: Canis familiaris

<400> SEQUENCE: 14

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
```

```
            145                 150                 155                 160
        Gln Tyr Val Leu Asp Lys Leu Gly Asp Asp Glu Val Arg Thr Asp Leu
                        165                 170                 175
        Lys Gln Gly Leu Asn Gly Val Pro Ile Leu Ser Glu Glu Leu Ser
                        180                 185                 190
        Leu Leu Asp Glu Phe Tyr Lys Leu Ala Asp Pro Glu Arg Asp Met Ser
                        195                 200                 205
        Leu Arg Leu Asn Glu Gln Tyr Glu His Ala Ser Ile His Leu Trp Asp
                        210                 215                 220
        Leu Leu Glu Gly Lys Glu Lys Ser Val Cys Gly Thr Thr Tyr Lys Ala
        225                 230                 235                 240
        Leu Lys Glu Ile Val Glu Arg Val Phe Gln Ser Asn Tyr Phe Asp Ser
                        245                 250                 255
        Thr His Asn His Gln Asn Gly Leu Cys Glu Glu Glu Ala Ala Ser
                        260                 265                 270
        Ala Pro Thr Val Glu Asp Gln Val Ala Glu Ala Glu Pro Glu Pro Ala
                        275                 280                 285
        Glu Glu Tyr Thr Glu Gln Ser Glu Val Glu Ser Thr Glu Tyr Val Asn
                        290                 295                 300
        Arg Gln Phe Met Ala Glu Thr Gln Phe Ser Ser Gly Glu Lys Glu Gln
        305                 310                 315                 320
        Val Asp Glu Trp Thr Val Glu Thr Val Glu Val Val Asn Ser Leu Gln
                        325                 330                 335
        Gln Gln Pro Gln Ala Ala Ser Pro Ser Val Pro Glu Pro His Ser Leu
                        340                 345                 350
        Thr Pro Val Ala Gln Ala Asp Pro Leu Val Arg Arg Gln Arg Val Gln
                        355                 360                 365
        Asp Leu Met Ala Gln Met Gln Gly Pro Tyr Asn Phe Ile Gln Asp Ser
                        370                 375                 380
        Met Leu Asp Phe Glu Asn Gln Thr Leu Asp Pro Ala Ile Val Ser Ala
        385                 390                 395                 400
        Gln Pro Met Asn Pro Thr Gln Asn Met Asp Met Pro Gln Leu Val Cys
                        405                 410                 415
        Pro Pro Val His Ser Glu Ser Arg Leu Ala Gln Pro Asn Gln Val Pro
                        420                 425                 430
        Val Gln Pro Glu Ala Thr Gln Val Pro Leu Val Ser Ser Thr Ser Glu
                        435                 440                 445
        Gly Tyr Thr Ala Ser Gln Pro Leu Tyr Gln Pro Ser His Ala Thr Glu
                        450                 455                 460
        Gln Arg Pro Gln Lys Glu Pro Ile Asp Gln Ile Gln Ala Thr Ile Ser
        465                 470                 475                 480
        Leu Asn Thr Asp Gln Thr Thr Ala Ser Ser Leu Pro Ala Ala Ser
                        485                 490                 495
        Gln Pro Gln Val Phe Gln Ala Gly Thr Ser Lys Pro Leu His Ser Ser
                        500                 505                 510
        Gly Ile Asn Val Asn Ala Ala Pro Phe Gln Ser Met Gln Thr Val Phe
                        515                 520                 525
        Asn Met Asn Ala Pro Val Pro Pro Val Asn Glu Pro Glu Thr Leu Lys
                        530                 535                 540
        Gln Gln Asn Gln Tyr Gln Ala Ser Tyr Asn Gln Ser Phe Ser Ser Gln
        545                 550                 555                 560
        Pro His Gln Val Glu Gln Thr Asp Leu Gln Gln Glu Gln Leu Gln Thr
                        565                 570                 575
```

| | | | | | | | | | | | | |
|---|---|---|---|---|---|---|---|---|---|---|---|---|
|Val|Val|Gly|Thr|Tyr|His|Gly|Ser|Gln|Asp|Gln|Pro|His|Gln|Val|Thr|
| | | |580| | | |585| | | |590| | | | |

Gly Asn His Gln Gln Pro Pro Gln Asn Thr Gly Phe Pro Arg Ser
        595             600             605

Ser Gln Pro Tyr Tyr Asn Ser Arg Gly Val Ser Arg Gly Gly Ser Arg
    610             615             620

Gly Ala Arg Gly Leu Met Asn Gly Tyr Arg Gly Pro Ala Asn Gly Phe
625             630             635             640

Arg Gly Gly Tyr Asp Gly Tyr Arg Pro Ser Phe Ser Asn Thr Pro Asn
            645             650             655

Ser Gly Tyr Thr Gln Ser Gln Phe Ser Ala Pro Arg Asp Tyr Ser Gly
        660             665             670

Tyr Gln Arg Asp Gly Tyr Gln Gln Asn Phe Lys Arg Gly Ser Gly Gln
    675             680             685

Ser Gly Pro Arg Gly Ala Pro Arg Gly Arg Gly Gly Pro Pro Arg Pro
    690             695             700

Asn Arg Gly Met Pro Gln Met Asn Thr Gln Gln Val Asn
705             710             715

```
<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)

<400> SEQUENCE: 15
```

| | |
|---|---|
|cgcgtctcgc cccgtccacc gattgactcg ccgctcttgt ccttcctccc gctctttctt|60|

| | | | | | | | | | | |
|---|---|---|---|---|---|---|---|---|---|---|
|ctctcccctt acggtttcaa g atg cct tcg gcc acc agc cac agc gga agc|111|
| |Met Pro Ser Ala Thr Ser His Ser Gly Ser| |
| |1           5              10| | ggc agc aag tcg tcc gga ccg cca ccg tcg ggt tcc tcc ggg aat     159
Gly Ser Lys Ser Ser Gly Pro Pro Pro Ser Gly Ser Ser Gly Asn
            15              20              25 gag gcg ggg gcc ggg gcc gcc gcg ccg gct tcc caa cac ccc atg acc   207
Glu Ala Gly Ala Gly Ala Ala Ala Pro Ala Ser Gln His Pro Met Thr
        30              35              40 ggc acc ggg gct gtc cag acc gag gcc atg aag cag att ctc ggg gtg   255
Gly Thr Gly Ala Val Gln Thr Glu Ala Met Lys Gln Ile Leu Gly Val
            45              50              55 atc gac aag aaa ctt cgg aac ctg gag aag aaa aag ggc aag ctt gat   303
Ile Asp Lys Lys Leu Arg Asn Leu Glu Lys Lys Lys Gly Lys Leu Asp
    60              65              70 gat tat cag gaa cga atg aac aaa ggg gaa agg ctt aat caa gat cag   351
Asp Tyr Gln Glu Arg Met Asn Lys Gly Glu Arg Leu Asn Gln Asp Gln
75              80              85              90 ctg gat gcc gtg tct aag tac cag gaa gtc aca aat aac ttg gag ttt   399
Leu Asp Ala Val Ser Lys Tyr Gln Glu Val Thr Asn Asn Leu Glu Phe
                95              100             105 gca aaa gaa tta cag agg agt ttc atg gca tta agc caa gat att cag   447
Ala Lys Glu Leu Gln Arg Ser Phe Met Ala Leu Ser Gln Asp Ile Gln
            110             115             120 aaa aca ata aag aag aca gca cgt cgg gag cag ctt atg aga gag gaa   495
Lys Thr Ile Lys Lys Thr Ala Arg Arg Glu Gln Leu Met Arg Glu Glu
        125             130             135 gct gaa cag aaa cgt tta aaa aca gta ctt gag ctg cag tat gtt ttg   543
Ala Glu Gln Lys Arg Leu Lys Thr Val Leu Glu Leu Gln Tyr Val Leu -continued

|   | 140 |   |   |   | 145 |   |   |   | 150 |   |   |   |   |     |
|---|-----|---|---|---|-----|---|---|---|-----|---|---|---|---|-----|
| gac | aaa | cta | gga | gat | gat | gaa | gtg | aga | act | gac | ctg | aag | caa | ggt | ttg | 591 |
| Asp | Lys | Leu | Gly | Asp | Asp | Glu | Val | Arg | Thr | Asp | Leu | Lys | Gln | Gly | Leu |     |
| 155 |   |   |   |   | 160 |   |   |   | 165 |   |   |   |   | 170 |     |

```
gac aaa cta gga gat gat gaa gtg aga act gac ctg aag caa ggt ttg     591
Asp Lys Leu Gly Asp Asp Glu Val Arg Thr Asp Leu Lys Gln Gly Leu
155                 160                 165                 170 aat gga gtg cca ata ttg tct gaa gag gag ttg tcg ttg tta gat gag     639
Asn Gly Val Pro Ile Leu Ser Glu Glu Glu Leu Ser Leu Leu Asp Glu
                175                 180                 185 ttc tac aaa tta gca gac cct gaa cga gac atg agc ttg agg ttg aat     687
Phe Tyr Lys Leu Ala Asp Pro Glu Arg Asp Met Ser Leu Arg Leu Asn
            190                 195                 200 gag cag tat gaa cat gcc tcc att cac ctg tgg gac ttg ctg gaa gga     735
Glu Gln Tyr Glu His Ala Ser Ile His Leu Trp Asp Leu Leu Glu Gly
        205                 210                 215 aag gaa aaa cct gta tgt gga aca act tat aaa gct cta aag gaa att     783
Lys Glu Lys Pro Val Cys Gly Thr Thr Tyr Lys Ala Leu Lys Glu Ile
220                 225                 230 gtt gag cgt gtt ttc cag tca aac tac ttt gac agc acc cac aac cac     831
Val Glu Arg Val Phe Gln Ser Asn Tyr Phe Asp Ser Thr His Asn His
235                 240                 245                 250 cag aat ggt ctg tgt gag gaa gag gca gcc tca gca cct aca gtt         879
Gln Asn Gly Leu Cys Glu Glu Glu Ala Ala Ser Ala Pro Thr Val
                255                 260                 265 gaa gac cag gca gct gaa gct gaa cct gag cca gtg gaa gaa tat act     927
Glu Asp Gln Ala Ala Glu Ala Glu Pro Glu Pro Val Glu Glu Tyr Thr
            270                 275                 280 gaa caa aat gag gtt gaa tca aca gag tat gta aat aga caa ttt atg     975
Glu Gln Asn Glu Val Glu Ser Thr Glu Tyr Val Asn Arg Gln Phe Met
        285                 290                 295 gca gaa aca cag ttc agc agt ggt gaa aag gag cag gta gat gat tgg     1023
Ala Glu Thr Gln Phe Ser Ser Gly Glu Lys Glu Gln Val Asp Asp Trp
300                 305                 310 aca gtt gaa aca gtt gag gtg gta aat tca ctc cag cag caa cct cag    1071
Thr Val Glu Thr Val Glu Val Val Asn Ser Leu Gln Gln Gln Pro Gln
315                 320                 325                 330 gct gca tct cct tca gta cca gaa ccc cac tct ttg acc cca gtg gct    1119
Ala Ala Ser Pro Ser Val Pro Glu Pro His Ser Leu Thr Pro Val Ala
                335                 340                 345 caa gcc gat ccc ctc gtg aga aga cag cga gta cag gac ctt atg gca    1167
Gln Ala Asp Pro Leu Val Arg Arg Gln Arg Val Gln Asp Leu Met Ala
            350                 355                 360 caa atg cag ggg ccc tat aat ttc ata cag gat tca atg ttg gat ttt    1215
Gln Met Gln Gly Pro Tyr Asn Phe Ile Gln Asp Ser Met Leu Asp Phe
        365                 370                 375 gaa aac cag aca ctt gat cct gcc att gta tct gca cag ccg atg aat    1263
Glu Asn Gln Thr Leu Asp Pro Ala Ile Val Ser Ala Gln Pro Met Asn
380                 385                 390 cca gca cag aac atg gac ata ccc cag ctg gtt tgc cct cca gtt cat    1311
Pro Ala Gln Asn Met Asp Ile Pro Gln Leu Val Cys Pro Pro Val His
395                 400                 405                 410 tct gaa tct aga ctt gct caa cct aat caa gtt tct gta cag cca gaa    1359
Ser Glu Ser Arg Leu Ala Gln Pro Asn Gln Val Ser Val Gln Pro Glu
                415                 420                 425 gct aca cag gtt cct ttg gtt tca tcc aca agt gag gga tat aca gca    1407
Ala Thr Gln Val Pro Leu Val Ser Ser Thr Ser Glu Gly Tyr Thr Ala
            430                 435                 440 tct caa ccc ttg tac caa cct tct cat gct act gac caa cga cca caa    1455
Ser Gln Pro Leu Tyr Gln Pro Ser His Ala Thr Asp Gln Arg Pro Gln
        445                 450                 455 aag gaa ccg att gat cag att cag gcg acg atc tct tta aat aca gac    1503
```

```
Lys Glu Pro Ile Asp Gln Ile Gln Ala Thr Ile Ser Leu Asn Thr Asp
    460                 465                 470 cag act aca gca tca tca tcc ctt cct gct gct tct cag cct caa gtg    1551
Gln Thr Thr Ala Ser Ser Ser Leu Pro Ala Ala Ser Gln Pro Gln Val
475                 480                 485                 490 ttc cag gct ggg aca agc aaa cct tta cat agc agt gga atc aat gta    1599
Phe Gln Ala Gly Thr Ser Lys Pro Leu His Ser Ser Gly Ile Asn Val
                495                 500                 505 aat gca gct cca ttc caa tcc atg caa acg gta ttc aat atg aat gcc    1647
Asn Ala Ala Pro Phe Gln Ser Met Gln Thr Val Phe Asn Met Asn Ala
            510                 515                 520 cca gtt cct cct gtt aat gaa cca gaa act tta aaa cag caa aat cag    1695
Pro Val Pro Pro Val Asn Glu Pro Glu Thr Leu Lys Gln Gln Asn Gln
        525                 530                 535 tac cag gcc agt tac aac cag agc ttt tcc agt cag cct cac caa gta    1743
Tyr Gln Ala Ser Tyr Asn Gln Ser Phe Ser Ser Gln Pro His Gln Val
    540                 545                 550 gaa caa aca gag ctt cag caa gaa cag ctt caa aca gtg gtt ggc act    1791
Glu Gln Thr Glu Leu Gln Gln Glu Gln Leu Gln Thr Val Val Gly Thr
555                 560                 565                 570 tat cat ggt tct cag gac cag ccc cat caa gtg act ggt aac cac cag    1839
Tyr His Gly Ser Gln Asp Gln Pro His Gln Val Thr Gly Asn His Gln
                575                 580                 585 cag cct cct cag cag aac act gga ttt cca cgt agc aat cag ccc tat    1887
Gln Pro Pro Gln Gln Asn Thr Gly Phe Pro Arg Ser Asn Gln Pro Tyr
            590                 595                 600 tac aac agt cgt ggt gtg tct cgt gga ggt tcc cgt ggt gct aga ggc    1935
Tyr Asn Ser Arg Gly Val Ser Arg Gly Gly Ser Arg Gly Ala Arg Gly
        605                 610                 615 ttg atg aat gga tac aga gga cct gct aat gga ttc aga gga gga tat    1983
Leu Met Asn Gly Tyr Arg Gly Pro Ala Asn Gly Phe Arg Gly Gly Tyr
    620                 625                 630 gat ggt tac cgc cct tca ttc tct act aac act cca aac agt ggt tat    2031
Asp Gly Tyr Arg Pro Ser Phe Ser Thr Asn Thr Pro Asn Ser Gly Tyr
635                 640                 645                 650 aca caa tct caa ttc agt gct ccc cgg gac tac tct ggc tat cag cgg    2079
Thr Gln Ser Gln Phe Ser Ala Pro Arg Asp Tyr Ser Gly Tyr Gln Arg
                655                 660                 665 gat gga tat cag cag aat ttc aag cga ggc tct ggg cag agt gga cca    2127
Asp Gly Tyr Gln Gln Asn Phe Lys Arg Gly Ser Gly Gln Ser Gly Pro
            670                 675                 680 cgg gga gcc cca cga ggt cgt gga ggg ccc cca aga ccc aac aga ggg    2175
Arg Gly Ala Pro Arg Gly Arg Gly Gly Pro Pro Arg Pro Asn Arg Gly
        685                 690                 695 atg ccg caa atg aac act cag caa gtg aat taa tctgattcac aggattatgt  2228
Met Pro Gln Met Asn Thr Gln Gln Val Asn
    700                 705 ttaatcgcca aaacacact ggccagtgta ccataatatg ttaccagaag agttattatc   2288
tatttgttct ccctttcagg aaacttattg taaaggggact gttttcatcc cataaagaca  2348
ggactacaat tgtcagcttt atattacctg gatatggaag gaaactatt ttactctgca   2408 tgttctgtcc taagcgtcat cttgagcctt gcacatgata ctcagattcc tcacccttgc  2468
ttaggagtaa aacataatat actttaatgg ggtgatatct ccatagttat ttgaagtggc  2528
ttggataaag caagactgac ttctgacatt ggataaaatc tacaaatcag ccctagagtc  2588
attcagtggt aactgacaaa actaaaaatat ttcccttgaa aggaagatgg aaggagtgga  2648
gtgtggtttg gcagaacaac tgcatttcac agcttttcca cttaaattgg agcactgaac  2708
```

-continued

```
atttagatgc ataccgaatt atgcatgggc cctaatcaca cagacaaggc tggtgccagc      2768
cttaggcttg acacggcagt gttcaccctc tggccagacg actgtggttc aagacacatg      2828
taaattgctt tttaacagct gatactgtat aagacaaagc caaaatgcaa aattaggctt      2888
tgattggcac ttttcgaaaa atatgcaaca attaagggat ataatctgga tggccgcttc      2948
tgtacttaat gtgaaatatt tagatacctt tcaaacactt aacagtttct ttgacaatga      3008
gttttgtaag gattggtagt aaatatcatt ccttatgacg tacattgtct gtcactaatc      3068
cttggatctt gctgtattgt cacctaaatt ggtacaggta ctgatgaaaa tctaatggat      3128
aatcataaca ctcttggtta catgtttttc ctgcagcctg aaagttttta taagaaaaag      3188
acatcaaatg cctgctgctg ccacccttt aaattgctat cttttgaaaa gcaccagtat      3248 gtgtttaga ttgatttccc tattttaggg aaatgacagt cagtagtttc acttctgatg      3308
gtataagcaa acaaataaaa catgtttata aaaaaaaaaa aaaaaaaaaa aaaaaaaaaa      3368
aaaaaaaaaa aaaaaaaa                                                   3386
```

<210> SEQ ID NO 16
<211> LENGTH: 708
<212> TYPE: PRT
<213> ORGANISM: Bos taurus

<400> SEQUENCE: 16

```
Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255
```

-continued

```
Glu Glu Glu Ala Ala Ser Ala Pro Thr Val Glu Asp Gln Ala Ala Glu
            260                 265                 270

Ala Glu Pro Glu Pro Val Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
                435                 440                 445

Pro Ser His Ala Thr Asp Gln Arg Pro Gln Lys Glu Pro Ile Asp Gln
            450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
            515                 520                 525

Glu Pro Glu Thr Leu Lys Gln Gln Asn Gln Tyr Gln Ala Ser Tyr Asn
        530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Ser Gln Phe Ser
                645                 650                 655

Ala Pro Arg Asp Tyr Ser Gly Tyr Gln Arg Asp Gly Tyr Gln Gln Asn
            660                 665                 670
```

```
Phe Lys Arg Gly Ser Gly Gln Ser Gly Pro Arg Gly Ala Pro Arg Gly
            675                 680                 685

Arg Gly Gly Pro Pro Arg Pro Asn Arg Gly Met Pro Gln Met Asn Thr
        690                 695                 700

Gln Gln Val Asn
705

<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17 atg gag ggc aag ctc gat gat tac caa gag cga atg aac aaa gga gaa      48
Met Glu Gly Lys Leu Asp Asp Tyr Gln Glu Arg Met Asn Lys Gly Glu
1               5                   10                  15 agg ctt aat cag gat cag ctg gat gct gtg tct aag tac cag gaa gtc      96
Arg Leu Asn Gln Asp Gln Leu Asp Ala Val Ser Lys Tyr Gln Glu Val
            20                  25                  30 aca aat aac ttg gag ttt gcg aaa gaa ttg cag agg agt ttc atg gcg     144
Thr Asn Asn Leu Glu Phe Ala Lys Glu Leu Gln Arg Ser Phe Met Ala
        35                  40                  45 ttg agt cag gat att cag aaa aca ata aag aag acg gca cgt cgg gag     192
Leu Ser Gln Asp Ile Gln Lys Thr Ile Lys Lys Thr Ala Arg Arg Glu
    50                  55                  60 cag ctt atg aga gaa gaa gct gaa cag aaa cgt tta aaa act gta ctt     240
Gln Leu Met Arg Glu Glu Ala Glu Gln Lys Arg Leu Lys Thr Val Leu
65                  70                  75                  80 gag ctg cag tat gtt ttg gac aaa ttg gga gat gaa gaa gtg cga act     288
Glu Leu Gln Tyr Val Leu Asp Lys Leu Gly Asp Glu Glu Val Arg Thr
                85                  90                  95 gac ctg aaa caa ggt ttg aat gga gtg cca ata ctc tct gaa gaa gag     336
Asp Leu Lys Gln Gly Leu Asn Gly Val Pro Ile Leu Ser Glu Glu Glu
            100                 105                 110 ttg tcg ctg ttg gat gag ttc tac aag tta gca gac cct gta cgg gac     384
Leu Ser Leu Leu Asp Glu Phe Tyr Lys Leu Ala Asp Pro Val Arg Asp
        115                 120                 125 atg agc ttg agg ttg aat gag cag tat gag cat gcc tcc att cac ctg     432
Met Ser Leu Arg Leu Asn Glu Gln Tyr Glu His Ala Ser Ile His Leu
    130                 135                 140 tgg gac ttg ctg gaa ggg aag gaa aaa tct gtc tgt gga aca acc tat     480
Trp Asp Leu Leu Glu Gly Lys Glu Lys Ser Val Cys Gly Thr Thr Tyr
145                 150                 155                 160 aaa gct ctg agg gaa att gtt gag cgt gtt ttc cag tcc aac tac ttt     528
Lys Ala Leu Arg Glu Ile Val Glu Arg Val Phe Gln Ser Asn Tyr Phe
                165                 170                 175 gac agc acc cac aac cac cag aat ggg ctc tgt gag gag gaa gag gct     576
Asp Ser Thr His Asn His Gln Asn Gly Leu Cys Glu Glu Glu Glu Ala
            180                 185                 190 acc tca gct cca aca gct gaa gac cag gga gct gaa gct gaa cct gag     624
Thr Ser Ala Pro Thr Ala Glu Asp Gln Gly Ala Glu Ala Glu Pro Glu
        195                 200                 205 cca gca gaa gaa tac act gaa caa agt gaa gtt gaa tca aca gag tat     672
Pro Ala Glu Glu Tyr Thr Glu Gln Ser Glu Val Glu Ser Thr Glu Tyr
    210                 215                 220 gta aat aga cag ttt atg gca gaa gcg cag ttc agt ggt gag aag gag     720
Val Asn Arg Gln Phe Met Ala Glu Ala Gln Phe Ser Gly Glu Lys Glu
225                 230                 235                 240
```

```
cag gtg gat gag tgg aca gtc gag acg gtc gag gtg gta aat tca ctc      768
Gln Val Asp Glu Trp Thr Val Glu Thr Val Glu Val Val Asn Ser Leu
            245                 250                 255 cag cag caa cct cag gct gca tct cct tca gta ccg gag ccc cac tct      816
Gln Gln Gln Pro Gln Ala Ala Ser Pro Ser Val Pro Glu Pro His Ser
        260                 265                 270 ttg act cca gtg gct cag gca gat ccc ctt gtg aga aga cag cga gta      864
Leu Thr Pro Val Ala Gln Ala Asp Pro Leu Val Arg Arg Gln Arg Val
    275                 280                 285 cag gac ctt atg gcg caa atg cag ggg ccc tat aat ttc ata cag gat      912
Gln Asp Leu Met Ala Gln Met Gln Gly Pro Tyr Asn Phe Ile Gln Asp
290                 295                 300 tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320 gca cag cct atg aat cca gca cag aat atg gac atg ccc cag ctg gtt     1008
Ala Gln Pro Met Asn Pro Ala Gln Asn Met Asp Met Pro Gln Leu Val
            325                 330                 335 tgc cct cca gtt cat gct gaa tct aga ctt gct caa cct aat caa gtt     1056
Cys Pro Pro Val His Ala Glu Ser Arg Leu Ala Gln Pro Asn Gln Val
        340                 345                 350 cct gta caa cca gaa gct aca cag gtt cct ttg gtt tca tcc aca agt     1104
Pro Val Gln Pro Glu Ala Thr Gln Val Pro Leu Val Ser Ser Thr Ser
    355                 360                 365 gag ggg tat aca gca tct cag ccc ttg tac cag cct tct cat gct aca     1152
Glu Gly Tyr Thr Ala Ser Gln Pro Leu Tyr Gln Pro Ser His Ala Thr
370                 375                 380 gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400 tct tta aat aca gac cag act aca gca tca tca tcc ctt cct gct gct     1248
Ser Leu Asn Thr Asp Gln Thr Thr Ala Ser Ser Leu Pro Ala Ala
            405                 410                 415 tct cag cct cag gtg ttc cag gct ggg aca agc aaa cct tta cac agc     1296
Ser Gln Pro Gln Val Phe Gln Ala Gly Thr Ser Lys Pro Leu His Ser
        420                 425                 430 agt ggg atc aat gta aat gca gcg cca ttc cag tcc atg caa acg gtg     1344
Ser Gly Ile Asn Val Asn Ala Ala Pro Phe Gln Ser Met Gln Thr Val
    435                 440                 445 ttc aac atg aat gcc ccg gtt cct cct gtt aat gaa cca gaa act tta     1392
Phe Asn Met Asn Ala Pro Val Pro Pro Val Asn Glu Pro Glu Thr Leu
450                 455                 460 aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480 ccg cct cac caa gta gag cag aca gag ctt ccg caa gag cag ctt cag     1488
Pro Pro His Gln Val Glu Gln Thr Glu Leu Pro Gln Glu Gln Leu Gln
            485                 490                 495 acg gtg gtt ggt act tac cat gct tcc caa gac cag ccc cat caa gtg     1536
Thr Val Val Gly Thr Tyr His Ala Ser Gln Asp Gln Pro His Gln Val
        500                 505                 510 acc ggt aac cac cag cag cct ccc cag cag aac act ggg ttt cca cgt     1584
Thr Gly Asn His Gln Gln Pro Pro Gln Gln Asn Thr Gly Phe Pro Arg
    515                 520                 525 agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
530                 535                 540 cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
```

```
              545                 550                 555                 560
ttc aga gga gga tat gat ggt tac cgc cct tcg ttc tct aac act cca         1728
Phe Arg Gly Gly Tyr Asp Gly Tyr Arg Pro Ser Phe Ser Asn Thr Pro
                565                 570                 575 aac agc ggt tac aca cag tct cag ttc agt gct ccc cgg gac tac tct         1776
Asn Ser Gly Tyr Thr Gln Ser Gln Phe Ser Ala Pro Arg Asp Tyr Ser
            580                 585                 590 ggc tat cag cgg gat gga tat cag cag aat ttc aag cga ggc tct ggg         1824
Gly Tyr Gln Arg Asp Gly Tyr Gln Gln Asn Phe Lys Arg Gly Ser Gly
        595                 600                 605 cag agt gga ccc cgg gga gcc cca cga ggt cgt gga ggg ccc cca aga         1872
Gln Ser Gly Pro Arg Gly Ala Pro Arg Gly Arg Gly Gly Pro Pro Arg
    610                 615                 620 ccc aac aga ggg atg ccg caa atg aac act cag caa gtg aat taa             1917
Pro Asn Arg Gly Met Pro Gln Met Asn Thr Gln Gln Val Asn
625                 630                 635 tctgattcac aggattatct taatcgcca aaacacactg ccagtgtac cataatatgt         1977 taccagaaga gttattatct atttgttctc cctttcagga aacttattgt aaagggactg       2037
ttttcatccc ataaagacag gactacagtt gtcagcttta tattacctgg atatggaagg       2097
aaactatttt tactctgcat gttctgtcct aagcgtcatc ttgagccttg cacatgatac       2157
tcagattcct ttcccttgct taggagtaaa acataatata ctttatgggg tgataatatc       2217
tccatagtta tttgaagtgg cttggaaaaa gcaagattga cttttgacat ggataaaat       2277 ctacaaatca gccctagagt ttcatggtca ttcacaaaac taaaatattt cccttgaaag       2337
gaagatggaa ggactggagt gtggtttggc agaacaactg catttcacag cttttcctat      2397
taaattggag cactgaatgt taaatgcata ccaaattatg catgggccct taatcacaca       2457
tacatggcta ccagctttga cacagcacta ttcatcctct ggccaaacga ctgtggttaa       2517
aaacacgtgt aaattgcttt ttaacagctg atactgtaaa agacaaagct aaaatgcaaa       2577
attaggcttt cattggcact tttcgaaaaa tatgcaacaa atttgggatg taatctggat       2637
ggccacttct gtacttaatg tgaagtattt agatacctttt tgaacacttt aacagttcct      2697
tcgacaatga cttttgtaag gattggtagt atatatcatt ccttatgaca tacattgtct       2757
gttgctaatc cttggatctt gctgtattgt cacctaaatt ggtacaggta ctgatgaaaa       2817
tctctcatgg ataaacctaa cactcttcgt cacatgtttt tcctgcagcc tgaaggtttt       2877
taaaaggaaa agatatcaaa tgcctgctgc taccacccctt ttaaattgct atcttttgaa      2937
aagcaccagt atgtgttttt agattgattt ccctatttta gggaaatgac agtcagtagt      2997
ttcagttctg atggtataag caaagcaaat aaaacgtgtt tataaaagtt gtatcttgaa      3057
acactggtgt tcaacagcta gcagcttctg tggttcaccc cctgccttgt tagtgttacc      3117
catttatggt tatctccagc agcaatttct cta                                    3150
```

<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala

```
            35                  40                  45
Leu Ser Gln Asp Ile Gln Lys Thr Ile Lys Lys Thr Ala Arg Arg Glu
 50                  55                  60

Gln Leu Met Arg Glu Glu Ala Glu Gln Lys Arg Leu Lys Thr Val Leu
 65                  70                  75                  80

Glu Leu Gln Tyr Val Leu Asp Lys Leu Gly Asp Glu Val Arg Thr
                     85                  90                  95

Asp Leu Lys Gln Gly Leu Asn Gly Val Pro Ile Leu Ser Glu Glu
                    100                 105                 110

Leu Ser Leu Leu Asp Glu Phe Tyr Lys Leu Ala Asp Pro Val Arg Asp
                115                 120                 125

Met Ser Leu Arg Leu Asn Glu Gln Tyr Glu His Ala Ser Ile His Leu
                130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Ala
                180                 185                 190

Thr Ser Ala Pro Thr Ala Glu Asp Gln Gly Ala Glu Ala Glu Pro Glu
                195                 200                 205

Pro Ala Glu Glu Tyr Thr Glu Gln Ser Glu Val Glu Ser Thr Glu Tyr
210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Asn Ser Leu
                245                 250                 255

Gln Gln Gln Pro Gln Ala Ala Ser Pro Ser Val Pro Glu Pro His Ser
                260                 265                 270

Leu Thr Pro Val Ala Gln Ala Asp Pro Leu Val Arg Arg Gln Arg Val
                275                 280                 285

Gln Asp Leu Met Ala Gln Met Gln Gly Pro Tyr Asn Phe Ile Gln Asp
290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
                340                 345                 350

Pro Val Gln Pro Glu Ala Thr Gln Val Pro Leu Val Ser Ser Thr Ser
                355                 360                 365

Glu Gly Tyr Thr Ala Ser Gln Pro Leu Tyr Gln Pro Ser His Ala Thr
                370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Leu Pro Ala Ala
                405                 410                 415

Ser Gln Pro Gln Val Phe Gln Ala Gly Thr Ser Lys Pro Leu His Ser
                420                 425                 430

Ser Gly Ile Asn Val Asn Ala Ala Pro Phe Gln Ser Met Gln Thr Val
                435                 440                 445

Phe Asn Met Asn Ala Pro Val Pro Pro Val Asn Glu Pro Glu Thr Leu
450                 455                 460
```

```
Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635

<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19
gctggctggc taagtccctc ccgcgccggc tcttgtccca ctaggagcag ctcagagccg      60
cggggacagg gcgaagcggc ctgcgcccac ggagcgcacg tctctgttct caacgcagca     120 ccaccttgc ccccctcggc tgcccactcc agacgtccag cggctccgcg cgcgcacg        178 atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca      274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45 acc gag gcc atg aag cag att ctc ggc gta atc gac aag aaa ctt cgg      370
Thr Glu Ala Met Lys Gln Ile Leu Gly Val Ile Asp Lys Lys Leu Arg
    50                  55                  60 aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80 aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95 tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110
```

| | |
|---|---|
| agt ttc atg gca tta agt caa gat att cag aaa aca ata aag aag aca<br>Ser Phe Met Ala Leu Ser Gln Asp Ile Gln Lys Thr Ile Lys Lys Thr<br>     115                       120                     125 | 562 |
| gca cgt cgg gaa cag ctt atg aga gaa gaa gca gaa cag aag cgc tta<br>Ala Arg Arg Glu Gln Leu Met Arg Glu Glu Ala Glu Gln Lys Arg Leu<br>130                       135                       140 | 610 |
| aaa act gta ctt gag tta cag tat gta ttg gat aag ctg gga gat gat<br>Lys Thr Val Leu Glu Leu Gln Tyr Val Leu Asp Lys Leu Gly Asp Asp<br>145                       150                     155                   160 | 658 |
| gat gtg aga aca gat ctg aaa caa ggt ttg agt gga gtg cca ata ttg<br>Asp Val Arg Thr Asp Leu Lys Gln Gly Leu Ser Gly Val Pro Ile Leu<br>                   165                     170                   175 | 706 |
| tct gag gag gag ttg tca ttg ctg gat gag ttc tac aag ctc gta gat<br>Ser Glu Glu Glu Leu Ser Leu Leu Asp Glu Phe Tyr Lys Leu Val Asp<br>                       180                     185                   190 | 754 |
| cct gag cgt gac atg agt tta agg tta aat gag cag tat gaa cat gcc<br>Pro Glu Arg Asp Met Ser Leu Arg Leu Asn Glu Gln Tyr Glu His Ala<br>     195                       200                     205 | 802 |
| tca att cac ttg tgg gat ttg ctg gaa ggg aaa gaa aag cct gtg tgt<br>Ser Ile His Leu Trp Asp Leu Leu Glu Gly Lys Glu Lys Pro Val Cys<br>210                       215                       220 | 850 |
| gga aca acc tat aaa gct cta aag gaa att gtt gag cgt gtt ttc cag<br>Gly Thr Thr Tyr Lys Ala Leu Lys Glu Ile Val Glu Arg Val Phe Gln<br>225                       230                     235                   240 | 898 |
| tca aac tac ttt gat agc act cac aat cat caa aat ggg ttg tgt gag<br>Ser Asn Tyr Phe Asp Ser Thr His Asn His Gln Asn Gly Leu Cys Glu<br>                   245                     250                   255 | 946 |
| gag gaa gag gcg gct tca gcg ccc aca gtg gag gac cag gta gct gaa<br>Glu Glu Glu Ala Ala Ser Ala Pro Thr Val Glu Asp Gln Val Ala Glu<br>               260                     265                     270 | 994 |
| gct gaa cct gag cca gcg gaa gaa tac aca gag caa agt gag gtt gaa<br>Ala Glu Pro Glu Pro Ala Glu Glu Tyr Thr Glu Gln Ser Glu Val Glu<br>             275                     280                     285 | 1042 |
| tca aca gag tat gtc aat agg cag ttc atg gca gaa aca cag ttc agc<br>Ser Thr Glu Tyr Val Asn Arg Gln Phe Met Ala Glu Thr Gln Phe Ser<br>290                       295                     300 | 1090 |
| agt ggt gag aag gag caa gtg gat gag tgg aca gtt gaa aca gtt gag<br>Ser Gly Glu Lys Glu Gln Val Asp Glu Trp Thr Val Glu Thr Val Glu<br>305                       310                     315                   320 | 1138 |
| gtt gta aac tca ctc cag cag caa cct cag gct gcg tcc cct tca gtc<br>Val Val Asn Ser Leu Gln Gln Gln Pro Gln Ala Ala Ser Pro Ser Val<br>                   325                     330                   335 | 1186 |
| cca gag ccc cac tct ttg act cca gtg gct cag tca gat cca ctt gtg<br>Pro Glu Pro His Ser Leu Thr Pro Val Ala Gln Ser Asp Pro Leu Val<br>             340                     345                     350 | 1234 |
| aga agg cag cgt gta caa gat ctt atg gca caa atg caa ggg ccc tat<br>Arg Arg Gln Arg Val Gln Asp Leu Met Ala Gln Met Gln Gly Pro Tyr<br>                   355                     360                   365 | 1282 |
| aat ttc ata cag gat tca atg ttg gat ttt gaa aat cag acg ctt gat<br>Asn Phe Ile Gln Asp Ser Met Leu Asp Phe Glu Asn Gln Thr Leu Asp<br>370                       375                     380 | 1330 |
| cct gcc att gta tcc gca cag cct atg aac cct acc cag aac atg gat<br>Pro Ala Ile Val Ser Ala Gln Pro Met Asn Pro Thr Gln Asn Met Asp<br>385                       390                     395                   400 | 1378 |
| atg cct cag ctg gtt tgc cct cag gtt cat tct gaa tct aga ctt gcc<br>Met Pro Gln Leu Val Cys Pro Gln Val His Ser Glu Ser Arg Leu Ala<br>                   405                     410                   415 | 1426 |
| caa tct aat caa gtt cct gta caa cca gaa gcc aca cag gtt cct ttg<br>Gln Ser Asn Gln Val Pro Val Gln Pro Glu Ala Thr Gln Val Pro Leu<br>             420                     425                     430 | 1474 |

```
gtt tca tcc aca agt gag ggg tat aca gca tct cag ccc ttg tac cag    1522
Val Ser Ser Thr Ser Glu Gly Tyr Thr Ala Ser Gln Pro Leu Tyr Gln
            435                 440                 445 cca tct cat gct acg gag cag cgg ccg cag aaa gag cca atg gat cag    1570
Pro Ser His Ala Thr Glu Gln Arg Pro Gln Lys Glu Pro Met Asp Gln
    450                 455                 460 att cag gca aca ata tct ttg aat aca gac cag act aca gca tcc tca    1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt    1666
Ser Leu Pro Ala Ala Ser Gln Pro Gln Val Phe Gln Ala Gly Thr Ser
                485                 490                 495 aaa cct ttg cac agc agt gga atc aat gta aat gca gct cca ttc cag    1714
Lys Pro Leu His Ser Ser Gly Ile Asn Val Asn Ala Ala Pro Phe Gln
            500                 505                 510 tcc atg caa acg gtg ttc aat atg aat gct cca gtc cct cct gct aat    1762
Ser Met Gln Thr Val Phe Asn Met Asn Ala Pro Val Pro Pro Ala Asn
            515                 520                 525 gaa cca gaa acg tta aaa caa cag agt cag tac cag gcc act tat aac    1810
Glu Pro Glu Thr Leu Lys Gln Gln Ser Gln Tyr Gln Ala Thr Tyr Asn
    530                 535                 540 cag agt ttt tcc agt cag cct cac caa gtg gaa caa aca gag ctt caa    1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac    1906
Gln Asp Gln Leu Gln Thr Val Val Gly Thr Tyr His Gly Ser Gln Asp
                565                 570                 575 cag cct cat caa gtg cct ggt aac cac cag caa ccc cca cag cag aac    1954
Gln Pro His Gln Val Pro Gly Asn His Gln Gln Pro Pro Gln Gln Asn
            580                 585                 590 act ggc ttt cca cgt agc agt cag cct tat tac aac agt cgt ggg gta    2002
Thr Gly Phe Pro Arg Ser Ser Gln Pro Tyr Tyr Asn Ser Arg Gly Val
            595                 600                 605 tct cga gga ggg tct cgt ggt gcc aga ggc ttg atg aat gga tac agg    2050
Ser Arg Gly Gly Ser Arg Gly Ala Arg Gly Leu Met Asn Gly Tyr Arg
            610                 615                 620 ggc cct gcc aat gga ttt aga gga gga tat gat ggt tac cgc cct tca    2098
Gly Pro Ala Asn Gly Phe Arg Gly Gly Tyr Asp Gly Tyr Arg Pro Ser
625                 630                 635                 640 ttc tcg aac act cca aac agt ggt tat tca cag tct cag ttc act gct    2146
Phe Ser Asn Thr Pro Asn Ser Gly Tyr Ser Gln Ser Gln Phe Thr Ala
                645                 650                 655 ccc cgg gac tac tct ggt tac cag cgg gat gga tat cag cag aat ttc    2194
Pro Arg Asp Tyr Ser Gly Tyr Gln Arg Asp Gly Tyr Gln Gln Asn Phe
            660                 665                 670 aag cga ggc tct ggg cag agt gga cca cgg gga gcc cca cga ggt cgt    2242
Lys Arg Gly Ser Gly Gln Ser Gly Pro Arg Gly Ala Pro Arg Gly Arg
            675                 680                 685 gga ggg ccc cca aga ccc aac aga ggg atg ccg caa atg aac act cag    2290
Gly Gly Pro Pro Arg Pro Asn Arg Gly Met Pro Gln Met Asn Thr Gln
            690                 695                 700 caa gtg aat taa tgtgatacac aggattatgt ttaatcgcca aaaacacact         2342
Gln Val Asn
705 ggccagtgta ccataatatg ttaccagaag agttattatc tatttgttct ccctttcagg   2402 aaacttattg taagggact gttttcatcc cataaagaca ggactgcaat tgtcagcttt    2462 acattacctg gatatggaag gaaactattt ttattctgca tgttctgtcc taagcgtcat   2522
```

```
cttgagcctt gcacacaata caatactcag attcctcacc cttgcttagg agtaaaacat   2582
tatatactta tggggtgata atatctccat agttagttga agtggcttgg aaaaaaaatg   2642
caagattgaa tttttgacct tggataaaat ctacaatcag ccctagaact attcagtggt   2702
aattgacaaa gttaaagcat tttctttgaa aggaagatgg aaggagtgga gtgtggttta   2762
gcaaaactgc atttcatagc tttcccatta aattggagca ccgacagatt aaaagcatac   2822
caaattatgc atgggtcctt actcacacaa gtgaggctgg ctaccagcct tgacatagca   2882
ctcactagtc ttctggccaa acgactgtga ttaaaacaca tgtaaattgc tctttagtag   2942
tggatactgt gtaagacaaa gccaaattgc aaatcaggct ttgattggct cttctggaaa   3002
atatgcatca aatatggggg ataatctgga tgggctgctg ctgtgctcaa tgtgaactat   3062
ttagatacct ttggaacact taacagtttc tctgaacaat gacttacatg gggattggtc   3122
ctgtttgtca ttcctcacca taattgcatt gtcatcacta atccttggat cttgctgtat   3182
tgttactcaa attggtaata ggtactgatg gaaatcgcta atggatggat aatcataaca   3242
cttttggtca catgttttct cctgcagcct gaaagttctt aaagaaaaag atatcaaatg   3302
cctgctgcta ccacccttt aaattgctat ctttagaaaa gcaccggtat gtgttttaga   3362
ttcatttccc tgttttaggg aaatgacagg cagtagtttc agttctgatg gcaaaacaaa   3422
taaaaacatg tttctaaaag ttgtatcttg aaacactggt gttcaacagc tagcagctaa   3482
agtaattcaa cccatgcatt gctagtgtca cagccttttgg ttatgtctag tagctgtttc   3542
tgaagtattt tcatttatct tttgtcaaat ttaaccctgt ttgaattctc tcctttcctc   3602
aaggagacac ttatgttcaa agtgttgatt ctttgcctta ggtgcataga gagtagacag   3662
tttggagatg gaaaggttag cagtgactta gccatatgtt ctgtgttgga atttgtgcta   3722
gcagtttgag cactagctct gcgtgcctat gaactgaatg ctgcttgtcc cattccattt   3782
tatgtcatgg agaaataatt ccacttggta acacaaaggc taagttaatg ttattttctg   3842
tacagaaatt aaattttact tttagccttt tgtaaacttt tttttttttt ttccaagccg   3902
gtatcagcta ctcaaaacaa ttctcagata ttcatcatta gacaactgga gttttgctg    3962 gttttgtagc ctactaaaac tgctgaggct gttgaacatt ccacattcaa aagttttgta   4022
gggtggtgga taatggggaa gcttcaatgt ttatttaaa ataaataaaa taagttcttg    4082
acttttctca tgtgtggtta tggtacatca tattggaagg gttatctgtt tacttttgcc   4142
aagactattt tgccagcacc tacacttgtg tgctttaaaa gacaactacc tgggatgtac   4202
cacaaccata tgttaattgt attttattgg gatggtaaaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtctttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg attttttttc atcctttctc ctctttgat  cattgtatct   4922
```

```
tgatattaaa aacatgacct tccaatgatt gtagtaaatt aacttctata gttcttttgt    4982
ctctatatgt attcatatat atgctattgt atagagactt caaggagaca tggagatgca    5042
tgcttattct caggttcatt cactaaggtg cttggcagac aaccagtttc taagtgcaga    5102
atgtagttaa gcagcttcat atatgtgcca ggcaatttgt tttgttaaat tttcatctac    5162
ttaaggaaat agggtattgt agcttaggct gatcataccc ttcatttcaa ccttaagctc    5222
tcaacctgca tccatccgac ttgagctatt aagtacttta gttttatcga gtataagtta    5282
acagaaaaag taaattaagc tttgccttta ctattttgaa tttatataca ttctggaaaa    5342
acttagaaac tgttgtatat ttcattagat taaattatat gaaaatgtga ttgtttatag    5402
caaagcctgt gagttgcata caccctaagg aaaactcctt aagtgctcct tgaagagaga    5462
agaaacaatt ctgggtctgg tcttttttaag aacaaagcta gactactgta tgttagcact    5522
gtacattaat agtctgttgt gaagcttgag cagtttcctg catagccttg atccttcacc    5582
gttggcattg aaaatagcag tatccctgat gtacttaaaa cttaaagtca ggttttggta    5642
tatttatttg taagtcttaa tttcctctaa atactatatc tctttagcga gacaacctga    5702
aatttattag cacatttggg tatctcttgc ttggcattat ggccagtgtt aactattcag    5762
tggtgaaaaa attacccctc aagacactgg agtgaccccca gatgtgtgta gtaagtggca    5822
tggttcaact gtgtggttaa tgataaatat atgactatgt cggtatgatc tggaaagact    5882
tgattgaaag ataattcagc tgacataagg atgagtgagg agtggcaaac tggataaaag    5942
agtcaagaga cctgtattcc agtgactcct gttttgttta agcattagca agatctgtct    6002
ggggaaactg gatagggcag ttttcttcca tgtttagttt ttgtctcaac atttggaagc    6062
tattgaaggt tttaaaatgg tgtgtattgt ttttttttgg ggggggggtg gccagaatag    6122
tgggtcatct aataaaactg ccatttaaaa gatcaaaaaa aaaaaaaaaa aaaaaaaa     6181
```

<210> SEQ ID NO 20
<211> LENGTH: 707
<212> TYPE: PRT
<213> ORGANISM: Mus musculus

<400> SEQUENCE: 20

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Ala Ala Pro Ala Ser Gln His Pro Ala Thr Gly Thr Gly Ala Val Gln
            35                  40                      45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
```

-continued

```
            145                 150                 155                 160
        Asp Val Arg Thr Asp Leu Lys Gln Gly Leu Ser Gly Val Pro Ile Leu
                        165                 170                 175
        Ser Glu Glu Glu Leu Ser Leu Leu Asp Glu Phe Tyr Lys Leu Val Asp
                        180                 185                 190
        Pro Glu Arg Asp Met Ser Leu Arg Leu Asn Glu Gln Tyr Glu His Ala
                        195                 200                 205
        Ser Ile His Leu Trp Asp Leu Leu Glu Gly Lys Glu Lys Pro Val Cys
                        210                 215                 220
        Gly Thr Thr Tyr Lys Ala Leu Lys Glu Ile Val Glu Arg Val Phe Gln
        225                 230                 235                 240
        Ser Asn Tyr Phe Asp Ser Thr His Asn His Gln Asn Gly Leu Cys Glu
                        245                 250                 255
        Glu Glu Glu Ala Ala Ser Ala Pro Thr Val Glu Asp Gln Val Ala Glu
                        260                 265                 270
        Ala Glu Pro Glu Pro Ala Glu Glu Tyr Thr Glu Gln Ser Glu Val Glu
                        275                 280                 285
        Ser Thr Glu Tyr Val Asn Arg Gln Phe Met Ala Glu Thr Gln Phe Ser
                        290                 295                 300
        Ser Gly Glu Lys Glu Gln Val Asp Glu Trp Thr Val Glu Thr Val Glu
        305                 310                 315                 320
        Val Val Asn Ser Leu Gln Gln Pro Gln Ala Ala Ser Pro Ser Val
                        325                 330                 335
        Pro Glu Pro His Ser Leu Thr Pro Val Ala Gln Ser Asp Pro Leu Val
                        340                 345                 350
        Arg Arg Gln Arg Val Gln Asp Leu Met Ala Gln Met Gln Gly Pro Tyr
                        355                 360                 365
        Asn Phe Ile Gln Asp Ser Met Leu Asp Phe Glu Asn Gln Thr Leu Asp
                        370                 375                 380
        Pro Ala Ile Val Ser Ala Gln Pro Met Asn Pro Thr Gln Asn Met Asp
        385                 390                 395                 400
        Met Pro Gln Leu Val Cys Pro Gln Val His Ser Glu Ser Arg Leu Ala
                        405                 410                 415
        Gln Ser Asn Gln Val Pro Val Gln Pro Glu Ala Thr Gln Val Pro Leu
                        420                 425                 430
        Val Ser Ser Thr Ser Glu Gly Tyr Thr Ala Ser Gln Pro Leu Tyr Gln
                        435                 440                 445
        Pro Ser His Ala Thr Glu Gln Arg Pro Gln Lys Glu Pro Met Asp Gln
                        450                 455                 460
        Ile Gln Ala Thr Ile Ser Leu Asn Thr Asp Gln Thr Thr Ala Ser Ser
        465                 470                 475                 480
        Ser Leu Pro Ala Ala Ser Gln Pro Gln Val Phe Gln Ala Gly Thr Ser
                        485                 490                 495
        Lys Pro Leu His Ser Ser Gly Ile Asn Val Asn Ala Ala Pro Phe Gln
                        500                 505                 510
        Ser Met Gln Thr Val Phe Asn Met Asn Ala Pro Val Pro Pro Ala Asn
                        515                 520                 525
        Glu Pro Glu Thr Leu Lys Gln Gln Ser Gln Tyr Gln Ala Thr Tyr Asn
                        530                 535                 540
        Gln Ser Phe Ser Ser Gln Pro His Gln Val Glu Gln Thr Glu Leu Gln
        545                 550                 555                 560
        Gln Asp Gln Leu Gln Thr Val Val Gly Thr Tyr His Gly Ser Gln Asp
                        565                 570                 575
```

-continued

```
Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705

<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)

<400> SEQUENCE: 21
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                    Met Pro Ser Ala Thr Ser His Ser Gly Ser Gly
                     1               5                  10 agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105 aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120 aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135
```

```
                                                                    -continued gaa cag aag cgc tta aaa act gta ctt gag tta cag tat gta ttg gat      603
Glu Gln Lys Arg Leu Lys Thr Val Leu Glu Leu Gln Tyr Val Leu Asp
140             145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc      699
Gly Val Pro Ile Leu Ser Glu Glu Glu Leu Ser Leu Leu Asp Glu Phe
                175                 180                 185 tac aag ctc gta gat cct gag cgt gac atg agt tta agg tta aat gag      747
Tyr Lys Leu Val Asp Pro Glu Arg Asp Met Ser Leu Arg Leu Asn Glu
                190                 195                 200 cag tat gaa cat gcc tca att cac ttg tgg gat ttg ctg gaa ggg aaa      795
Gln Tyr Glu His Ala Ser Ile His Leu Trp Asp Leu Leu Glu Gly Lys
205                 210                 215 gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
                255                 260                 265 gac cag gta gct gaa gct gaa cct gag cca gcg gaa gaa tac aca gag      987
Asp Gln Val Ala Glu Ala Glu Pro Glu Pro Ala Glu Glu Tyr Thr Glu
                270                 275                 280 caa agt gag gtt gaa tca aca gag tat gtc aat agg cag ttc atg gca     1035
Gln Ser Glu Val Glu Ser Thr Glu Tyr Val Asn Arg Gln Phe Met Ala
285                 290                 295 gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag     1179
Ala Ser Pro Ser Val Pro Glu Pro His Ser Leu Thr Pro Val Ala Gln
                335                 340                 345 tca gat cca ctt gtg aga agg cag cgt gta caa gat ctt atg gca caa     1227
Ser Asp Pro Leu Val Arg Arg Gln Arg Val Gln Asp Leu Met Ala Gln
                350                 355                 360 atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
365                 370                 375 aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410 gaa tct aga ctt gcc caa tct aat caa gtt cct gta caa cca gaa gcc     1419
Glu Ser Arg Leu Ala Gln Ser Asn Gln Val Pro Val Gln Pro Glu Ala
                415                 420                 425 aca cag gtt cct ttg gtt tca tcc aca agt gag ggg tat aca gca tct     1467
Thr Gln Val Pro Leu Val Ser Ser Thr Ser Glu Gly Tyr Thr Ala Ser
                430                 435                 440 cag ccc ttg tac cag cca tct cat gct acg gag cag cgg ccg cag aaa     1515
Gln Pro Leu Tyr Gln Pro Ser His Ala Thr Glu Gln Arg Pro Gln Lys
445                 450                 455
```

```
gag cca atg gat cag att cag gca aca ata tct ttg aat aca gac cag     1563
Glu Pro Met Asp Gln Ile Gln Ala Thr Ile Ser Leu Asn Thr Asp Gln
460             465                 470                 475 act aca gca tcc tca tcc ctt cct gct gct tct cag cct caa gtg ttc     1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat     1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca     1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac     1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa     1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac     1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa     1899
His Gly Ser Gln Asp Gln Pro His Gln Val Pro Gly Asn His Gln Gln
            575                 580                 585 ccc cca cag cag aac act ggc ttt cca cgt agc agt cag cct tat tac     1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg     1995
Asn Ser Arg Gly Val Ser Arg Gly Gly Ser Arg Gly Ala Arg Gly Leu
    605                 610                 615 atg aat gga tac agg ggc cct gcc aat gga ttt aga gga gga tat gat     2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag     2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga     2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680 gcc cca cga ggt cgt gga ggg ccc cca aga ccc aac aga ggg atg ccg     2235
Ala Pro Arg Gly Arg Gly Gly Pro Pro Arg Pro Asn Arg Gly Met Pro
    685                 690                 695 caa atg aac act cag caa gtg aat taa tgtgatacac aggattatgt          2282
Gln Met Asn Thr Gln Gln Val Asn
700                 705 ttaatcgcca aaacacact ggccagtgta ccataatatg ttaccagaag agtattatc    2342 tatttgttct ccctttcagg aaacttattg taaagggact gttttcatcc cataaagaca  2402
ggactgcaat tgtcagcttt acattacctg gatatggaag gaaactattt ttattctgca  2462
tgttctgtcc taagcgtcat cttgagcctt gcacacaata caatactcag attcctcacc  2522
cttgcttagg agtaaaacat tatatactta tggggtgata atatctccat agttagttga  2582
agtggcttgg aaaaaaaatg caagattgaa tttttgacct tggataaaat ctacaatcag  2642
ccctagaact attcagtggt aattgacaaa gttaaagcat tttctttgaa aggaagatgg  2702
```

```
aaggagtgga gtgtggttta gcaaaactgc atttcatagc tttcccatta aattggagca   2762
ccgacagatt aaaagcatac caaattatgc atgggtcctt actcacacaa gtgaggctgg   2822
ctaccagcct tgacatagca ctcactagtc ttctggccaa acgactgtga ttaaaacaca   2882
tgtaaattgc tctttagtag tggatactgt gtaagacaaa gccaaattgc aaatcaggct   2942
ttgattggct cttctggaaa atatgcatca aatatggggg ataatctgga tgggctgctg   3002
ctgtgctcaa tgtgaactat ttagatacct tggaacact taacagtttc tctgaacaat    3062
gacttacatg gggattggtc ctgtttgtca ttcctcacca taattgcatt gtcatcacta   3122
atccttggat cttgctgtat tgttactcaa attggtaata ggtactgatg gaaatcgcta   3182
atggatggat aatcataaca cttttggtca catgttttct cctgcagcct gaaagttctt   3242
aaagaaaaag atatcaaatg cctgctgcta ccacccttt aaattgctat ctttagaaaa    3302
gcaccggtat gtgttttaga ttcatttccc tgttttaggg aaatgacagg cagtagtttc   3362
agttctgatg gcaaaacaaa taaaaacatg tttctaaaag ttgtatcttg aaacactggt   3422
gttcaacagc tagcagctaa agtaattcaa cccatgcatt gctagtgtca cagcctttgg   3482
ttatgtctag tagctgtttc tgaagtattt tcatttatct tttgtcaaat ttaaccctgt   3542
ttgaattctc tcctttcctc aaggagacac ttatgttcaa agtgttgatt ctttgcctta   3602
ggtgcataga gagtagacag tttggagatg gaaaggttag cagtgactta gccatatgtt   3662
ctgtgttgga atttgtgcta gcagtttgag cactagctct gcgtgcctat gaactgaatg   3722
ctgcttgtcc cattccattt tatgtcatgg agaaataatt ccacttggta acacaaaggc   3782
taagttaatg ttatttctg tacagaaatt aaatttact tttagccttt tgtaaacttt      3842
tttttttttt ttccaagccg gtatcagcta ctcaaaacaa ttctcagata ttcatcatta   3902
gacaactgga gttttgctg gttttgtagc ctactaaaac tgctgaggct gttgaacatt    3962
ccacattcaa aagttttgta gggtggtgga taatgggaa gcttcaatgt ttattttaaa    4022
ataaataaaa taagttcttg acttttctca tgtgtggtta tggtacatca tattggaagg   4082
gttatctgtt tacttttgcc aagactattt tgccagcacc tacacttgtg tgctttaaaa   4142
gacaactacc tgggatgtac cacaaccata tgttaattgt atttattgg gatggataaa    4202 atgtttgtgg tttattggat aatccctaga tggtgtgtta cgtgtgtaga atataatttt   4262
atgatagtaa gaaagcaaaa ttgaagaaaa taagtttagt attgaatttg agttctgaag   4322
tgaattcagg gaatgtctca cgtttcgggc ttctacccaa agtgtagggc agaaggtgta   4382
aaagttgttt gtagtttgac ttgtttattt tttaagttgc ttattccttt caacagcaac   4442
atatcattag ctgtcattct accattgcag ttctagtgag ttttaacgtc tgcattcaag   4502
actgttttaa aagcaacctc actggacaga gaactgctaa agtctttttcc ttaagatctg   4562 agtctttgtt actcagtatc ttctataata tgcaaatgct tgtctagagg cagaagacct   4622
tttgtttggt caagtgtgta ttttaccaga gtacagggaa ctgatggtcc tacatgtctc   4682
ttagtgtagt aagactataa aatcttttgt acatgcacaa ttcacagtat gtttagatac   4742
cacgtgtata atgcccccc ctcccccagg tagcatgcca ttgatgactt tttgcttagg    4802
gccattttat taccagggcc ttaatattcc taaaagatg attttttttc atcctttctc    4862
ctcttttgat cattgtatct tgatattaaa aacatgacct tccaatgatt gtagtaaatt   4922
aacttctata gttcttttgt ctctatatgt attcatatat atgctattgt atagagactt   4982
caaggagaca tggagatgca tgcttattct caggttcatt cactaaggtg cttggcagac   5042
aaccagtttc taagtgcaga atgtagttaa gcagcttcat atatgtgcca ggcaatttgt   5102
```

```
tttgttaaat tttcatctac ttaaggaaat agggtattgt agcttaggct gatcatacccc    5162 ttcatttcaa ccttaagctc tcaacctgca tccatccgac ttgagctatt aagtacttta    5222
gttttatcga gtataagtta acagaaaaag taaattaagc tttgccttta ctattttgaa    5282
tttatataca ttctggaaaa acttagaaac tgttgtatat ttcattagat taaattatat    5342
gaaaatgtga ttgtttatag caaagcctgt gagttgcata caccctaagg aaaactcctt    5402
aagtgctcct tgaagagaga agaaacaatt ctgggtctgg tcttttttaag aacaaagcta   5462 gactactgta tgttagcact gtacattaat agtctgttgt gaagcttgag cagtttcctg    5522
catagccttg atccttcacc gttggcattg aaaatagcag tatccctgat gtacttaaaa    5582
cttaaagtca ggttttggta tatttatttg taagtcttaa tttcctctaa atactatatc    5642 tcttagcga gacaacctga aatttattag cacatttggg tatctcttgc ttggcattat     5702
ggccagtgtt aactattcag tggtgaaaaa attacccctc aagacactgg agtgaccccca   5762 gatgtgtgta gtaagtggca tggttcaact gtgtggttaa tgataaatat atgacttagt    5822
cggtatgatc tggaaagact tgattgaaag ataattcagc tgacataagg atgagtgagg    5882
agtggcaaac tggataaaag agtcaagaga cctgtattcc agtgactcct gttttgttta    5942
agcattagca agatctgtct ggggaaactg ataggggcag ttttcttcca tgtttagttt    6002
ttgtctcaac atttggaagc tattgaaggt tttaaaatgg tgtgtattgt tttttttttgg   6062 ggggggggtg gccagaatag tgggtcatct aataaaactg ccatttaaaa gatcaaaaaa    6122
aaaaaaaaaa aaaaaaaa                                                   6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
```

```
                180               185                190
Pro Arg Asp Met Ser Leu Arg Leu Asn Glu Gln Tyr Glu His Ala
            195                 200                 205
Ser Ile His Leu Trp Asp Leu Leu Glu Gly Lys Glu Lys Pro Val Cys
        210                 215                 220
Gly Thr Thr Tyr Lys Ala Leu Lys Glu Ile Val Glu Arg Val Phe Gln
225                 230                 235                 240
Ser Asn Tyr Phe Asp Ser Thr His Asn His Gln Asn Gly Leu Cys Glu
                245                 250                 255
Glu Glu Glu Ala Ala Ser Ala Pro Thr Val Glu Asp Gln Val Ala Glu
            260                 265                 270
Ala Glu Pro Glu Pro Ala Glu Glu Tyr Thr Glu Gln Ser Glu Val Glu
        275                 280                 285
Ser Thr Glu Tyr Val Asn Arg Gln Phe Met Ala Glu Thr Gln Phe Ser
        290                 295                 300
Ser Gly Glu Lys Glu Gln Val Asp Glu Trp Thr Val Glu Thr Val Glu
305                 310                 315                 320
Val Val Asn Ser Leu Gln Gln Gln Pro Gln Ala Ala Ser Pro Ser Val
                325                 330                 335
Pro Glu Pro His Ser Leu Thr Pro Val Ala Gln Ser Asp Pro Leu Val
            340                 345                 350
Arg Arg Gln Arg Val Gln Asp Leu Met Ala Gln Met Gln Gly Pro Tyr
        355                 360                 365
Asn Phe Ile Gln Asp Ser Met Leu Asp Phe Glu Asn Gln Thr Leu Asp
        370                 375                 380
Pro Ala Ile Val Ser Ala Gln Pro Met Asn Pro Thr Gln Asn Met Asp
385                 390                 395                 400
Met Pro Gln Leu Val Cys Pro Gln Val His Ser Glu Ser Arg Leu Ala
                405                 410                 415
Gln Ser Asn Gln Val Pro Val Gln Pro Glu Ala Thr Gln Val Pro Leu
            420                 425                 430
Val Ser Ser Thr Ser Glu Gly Tyr Thr Ala Ser Gln Pro Leu Tyr Gln
        435                 440                 445
Pro Ser His Ala Thr Glu Gln Arg Pro Gln Lys Glu Pro Met Asp Gln
        450                 455                 460
Ile Gln Ala Thr Ile Ser Leu Asn Thr Asp Gln Thr Thr Ala Ser Ser
465                 470                 475                 480
Ser Leu Pro Ala Ala Ser Gln Pro Gln Val Phe Gln Ala Gly Thr Ser
                485                 490                 495
Lys Pro Leu His Ser Ser Gly Ile Asn Val Asn Ala Ala Pro Phe Gln
            500                 505                 510
Ser Met Gln Thr Val Phe Asn Met Asn Ala Pro Val Pro Pro Ala Asn
        515                 520                 525
Glu Pro Glu Thr Leu Lys Gln Gln Ser Gln Tyr Gln Ala Thr Tyr Asn
        530                 535                 540
Gln Ser Phe Ser Ser Gln Pro His Gln Val Glu Gln Thr Glu Leu Gln
545                 550                 555                 560
Gln Asp Gln Leu Gln Thr Val Val Gly Thr Tyr His Gly Ser Gln Asp
                565                 570                 575
Gln Pro His Gln Val Pro Gly Asn His Gln Gln Pro Gln Gln Asn
            580                 585                 590
Thr Gly Phe Pro Arg Ser Ser Gln Pro Tyr Tyr Asn Ser Arg Gly Val
        595                 600                 605
```

```
Ser Arg Gly Gly Ser Arg Gly Ala Arg Gly Leu Met Asn Gly Tyr Arg
    610                 615                 620
Gly Pro Ala Asn Gly Phe Arg Gly Gly Tyr Asp Gly Tyr Arg Pro Ser
625                 630                 635                 640
Phe Ser Asn Thr Pro Asn Ser Gly Tyr Ser Gln Ser Gln Phe Thr Ala
                645                 650                 655
Pro Arg Asp Tyr Ser Gly Tyr Gln Arg Asp Gly Tyr Gln Gln Asn Phe
            660                 665                 670
Lys Arg Gly Ser Gly Gln Ser Gly Pro Arg Gly Ala Pro Arg Gly Arg
        675                 680                 685
Gly Gly Pro Pro Arg Pro Asn Arg Gly Met Pro Gln Met Asn Thr Gln
    690                 695                 700
Gln Val Asn
705

<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                   Met Pro Ser Ala Thr Ser His Ser Gly Ser Gly
                     1               5                  10 agc aaa tcg tcg gga ccg ccg ccg tcc ggt tcc tcc ggg agt gag           219
Ser Lys Ser Ser Gly Pro Pro Pro Ser Gly Ser Ser Gly Ser Glu
            15                  20                  25 gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105 aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120 aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135 gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
```

```
            160                 165                 170
gga gtg cca ata ttg tct gag gag gag ttg tca ttg ctg gat gag ttc    699
Gly Val Pro Ile Leu Ser Glu Glu Glu Leu Ser Leu Leu Asp Glu Phe
            175                 180                 185 tac aag ctc gta gat cct gag cgt gac atg agt tta agg tta aat gag    747
Tyr Lys Leu Val Asp Pro Glu Arg Asp Met Ser Leu Arg Leu Asn Glu
            190                 195                 200 cag tat gaa cat gcc tca att cac ttg tgg gat ttg ctg gaa ggg aaa    795
Gln Tyr Glu His Ala Ser Ile His Leu Trp Asp Leu Leu Glu Gly Lys
            205                 210                 215 gaa aag cct gtg tgt gga aca acc tat aaa gct cta aag gaa att gtt    843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa    891
Glu Arg Val Phe Gln Ser Asn Tyr Phe Asp Ser Thr His Asn His Gln
                240                 245                 250 aat ggg ttg tgt gag gag gaa gag gcg gct tca gcc ccc aca gtg gag    939
Asn Gly Leu Cys Glu Glu Glu Glu Ala Ala Ser Ala Pro Thr Val Glu
                255                 260                 265 gac cag gta gct gaa gct gaa cct gag cca gcg gaa gaa tac aca gag    987
Asp Gln Val Ala Glu Ala Glu Pro Glu Pro Ala Glu Glu Tyr Thr Glu
            270                 275                 280 caa agt gag gtt gaa tca aca gag tat gtc aat agg cag ttc atg gca    1035
Gln Ser Glu Val Glu Ser Thr Glu Tyr Val Asn Arg Gln Phe Met Ala
285                 290                 295 gaa aca cag ttc agc agt ggt gag aag gag caa gtg gat gag tgg aca    1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct    1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag    1179
Ala Ser Pro Ser Val Pro Glu Pro His Ser Leu Thr Pro Val Ala Gln
            335                 340                 345 tca gat cca ctt gtg aga agg cag cgt gta caa gat ctt atg gca caa    1227
Ser Asp Pro Leu Val Arg Arg Gln Arg Val Gln Asp Leu Met Ala Gln
            350                 355                 360 atg caa ggg ccc tat aat ttc ata cag acg ctt gat cct gcc att gta    1275
Met Gln Gly Pro Tyr Asn Phe Ile Gln Thr Leu Asp Pro Ala Ile Val
365                 370                 375 tcc gca cag cct atg aac cct acc cag aac atg gat atg cct cag ctg    1323
Ser Ala Gln Pro Met Asn Pro Thr Gln Asn Met Asp Met Pro Gln Leu
380                 385                 390                 395 gtt tgc cct cag gtt cat tct gaa tct aga ctt gcc caa tct aat caa    1371
Val Cys Pro Gln Val His Ser Glu Ser Arg Leu Ala Gln Ser Asn Gln
                400                 405                 410 gtt cct gta caa cca gaa gcc aca cag gtt cct ttg gtt tca tcc aca    1419
Val Pro Val Gln Pro Glu Ala Thr Gln Val Pro Leu Val Ser Ser Thr
            415                 420                 425 agt gag ggg tat aca gca tct cag ccc ttg tac cag cca tct cat gct    1467
Ser Glu Gly Tyr Thr Ala Ser Gln Pro Leu Tyr Gln Pro Ser His Ala
            430                 435                 440 acg gag cag cgg ccg cag aaa gag cca atg gat cag att cag gca aca    1515
Thr Glu Gln Arg Pro Gln Lys Glu Pro Met Asp Gln Ile Gln Ala Thr
            445                 450                 455 ata tct ttg aat aca gac cag act aca gca tcc tca tcc ctt cct gct    1563
Ile Ser Leu Asn Thr Asp Gln Thr Thr Ala Ser Ser Ser Leu Pro Ala
460                 465                 470                 475 gct tct cag cct caa gtg ttc cag gct ggg aca agt aaa cct ttg cac    1611
```

```
Ala Ser Gln Pro Gln Val Phe Gln Ala Gly Thr Ser Lys Pro Leu His
            480                 485                 490 agc agt gga atc aat gta aat gca gct cca ttc cag tcc atg caa acg      1659
Ser Ser Gly Ile Asn Val Asn Ala Ala Pro Phe Gln Ser Met Gln Thr
        495                 500                 505 gtg ttc aat atg aat gct cca gtc cct cct gct aat gaa cca gaa acg      1707
Val Phe Asn Met Asn Ala Pro Val Pro Pro Ala Asn Glu Pro Glu Thr
            510                 515                 520 tta aaa caa cag agt cag tac cag gcc act tat aac cag agt ttt tcc      1755
Leu Lys Gln Gln Ser Gln Tyr Gln Ala Thr Tyr Asn Gln Ser Phe Ser
525                 530                 535 agt cag cct cac caa gtg gaa caa aca gag ctt caa caa gac caa ctg      1803
Ser Gln Pro His Gln Val Glu Gln Thr Glu Leu Gln Gln Asp Gln Leu
540                 545                 550                 555 caa acg gtg gtt ggc act tac cat gga tcc cag gac cag cct cat caa      1851
Gln Thr Val Val Gly Thr Tyr His Gly Ser Gln Asp Gln Pro His Gln
            560                 565                 570 gtg cct ggt aac cac cag caa ccc cca cag cag aac act ggc ttt cca      1899
Val Pro Gly Asn His Gln Gln Pro Pro Gln Gln Asn Thr Gly Phe Pro
            575                 580                 585 cgt agc agt cag cct tat tac aac agt cgt ggg gta tct cga gga ggg      1947
Arg Ser Ser Gln Pro Tyr Tyr Asn Ser Arg Gly Val Ser Arg Gly Gly
            590                 595                 600 tct cgt ggt gcc aga ggc ttg atg aat gga tac agg ggc cct gcc aat      1995
Ser Arg Gly Ala Arg Gly Leu Met Asn Gly Tyr Arg Gly Pro Ala Asn
605                 610                 615 gga ttt aga gga gga tat gat ggt tac cgc cct tca ttc tcg aac act      2043
Gly Phe Arg Gly Gly Tyr Asp Gly Tyr Arg Pro Ser Phe Ser Asn Thr
620                 625                 630                 635 cca aac agt ggt tat tca cag tct cag ttc act gct ccc cgg gac tac      2091
Pro Asn Ser Gly Tyr Ser Gln Ser Gln Phe Thr Ala Pro Arg Asp Tyr
            640                 645                 650 tct ggt tac cag cgg gat gga tat cag cag aat ttc aag cga ggc tct      2139
Ser Gly Tyr Gln Arg Asp Gly Tyr Gln Gln Asn Phe Lys Arg Gly Ser
            655                 660                 665 ggg cag agt gga cca cgg gga gcc cca cga ggt cgt gga ggg ccc cca      2187
Gly Gln Ser Gly Pro Arg Gly Ala Pro Arg Gly Arg Gly Gly Pro Pro
            670                 675                 680 aga ccc aac aga ggg atg ccg caa atg aac act cag caa gtg aat taa      2235
Arg Pro Asn Arg Gly Met Pro Gln Met Asn Thr Gln Gln Val Asn
685                 690                 695 tgtgatacac aggattatgt ttaatcgcca aaaacacact ggccagtgta ccataatatg    2295
ttaccagaag agttattatc tatttgttct ccctttcagg aaacttattg taaagggact    2355
gttttcatcc cataaagaca ggactgcaat tgtcagcttt acattacctg gatatggaag    2415
gaaactattt ttattctgca tgttctgtcc taagcgtcat cttgagcctt gcacacaata    2475
caatactcag attcctcacc cttgcttagg agtaaaacat tatatactta tggggtgata    2535
atatctccat agttagttga agtggcttgg aaaaaaaatg caagattgaa ttttgacct     2595 tggataaaat ctacaatcag ccctagaact attcagtggt aattgacaaa gttaaagcat    2655
tttctttgaa aggaagatgg aaggagtgga gtgtggttta gcaaaactgc atttcatagc    2715
tttcccatta aattggagca ccgacagatt aaaagcatac caattatgc atgggtcctt     2775 actcacacaa gtgaggctgg ctaccagcct tgacatagca ctcactagtc ttctggccaa    2835
acgactgtga ttaaaacaca tgtaaattgc tctttagtag tggatactgt gtaagacaaa    2895
gccaaattgc aaatcaggct ttgattggct cttctggaaa atatgcatca aatatggggg    2955
```

```
ataatctgga tgggctgctg ctgtgctcaa tgtgaactat ttagatacct ttggaacact    3015
taacagtttc tctgaacaat gacttacatg gggattggtc ctgtttgtca ttcctcacca    3075
taattgcatt gtcatcacta atccttggat cttgctgtat tgttactcaa attggtaata    3135
ggtactgatg gaaatcgcta atggatggat aatcataaca cttttggtca catgttttct    3195
cctgcagcct gaaagttctt aaagaaaaag atatcaaatg cctgctgcta ccacccttt     3255 aaattgctat ctttagaaaa gcaccggtat gtgttttaga ttcatttccc tgttttaggg    3315
aaatgacagg cagtagtttc agttctgatg gcaaaacaaa taaaaacatg tttctaaaag    3375
ttgtatcttg aaacactggt gttcaacagc tagcagctaa agtaattcaa cccatgcatt    3435
gctagtgtca cagcctttgg ttatgtctag tagctgtttc tgaagtattt tcatttatct    3495
tttgtcaaat ttaaccctgt ttgaattctc tcctttcctc aaggagacac ttatgttcaa    3555
agtgttgatt ctttgcctta ggtgcataga gagtagacag tttggagatg gaaaggttag    3615
cagtgactta gccatatgtt ctgtgttgga atttgtgcta gcagtttgag cactagctct    3675
gcgtgcctat gaactgaatg ctgcttgtcc cattccattt tatgtcatgg agaaataatt    3735
ccacttggta acacaaaggc taagttaatg ttattttctg tacagaaatt aaattttact    3795
tttagccttt tgtaaacttt tttttttttt ttccaagccg gtatcagcta ctcaaaacaa    3855
ttctcagata ttcatcatta gacaactgga gttttgctg gttttgtagc ctactaaaac     3915
tgctgaggct gttgaacatt ccacattcaa agttttgta gggtggtgga taatggggaa     3975
gcttcaatgt ttatttttaaa ataaataaaa taagttcttg acttttctca tgtgtggtta   4035
tggtacatca tattggaagg gttatctgtt tacttttgcc aagactattt tgccagcacc    4095
tacacttgtg tgcttttaaaa gacaactacc tgggatgtac cacaaccata tgttaattgt   4155
attttattgg gatggataaa atgtttgtgg tttattggat aatccctaga tggtgtgtta    4215
cgtgtgtaga atataatttt atgatagtaa gaaagcaaaa ttgaagaaaa taagtttagt    4275
attgaatttg agttctgaag tgaattcagg gaatgtctca cgtttcgggc ttctacccaa    4335
agtgtagggc agaaggtgta aaagttgttt gtagtttgac ttgtttattt tttaagttgc    4395
ttattccttt caacagcaac atatcattag ctgtcattct accattgcag ttctagtgag    4455
ttttaacgtc tgcattcaag actgttttaa aagcaacctc actggacaga gaactgctaa    4515
agtcttttcc ttaagatctg agtctttgtt actcagtatc ttctataata tgcaaatgct    4575
tgtctagagg cagaagacct tttgtttggt caagtgtgta ttttaccaga gtacagggaa    4635
ctgatggtcc tacatgtctc ttagtgtagt aagactataa aatcttttgt acatgcacaa    4695
ttcacagtat gtttagatac cacgtgtata atgcccccc ctcccccagg tagcatgcca     4755
ttgatgactt tttgcttagg gccatttttat taccagggcc ttaatattcc taaaaagatg   4815 atttttttc atcctttctc ctcttttgat cattgtatct tgatattaaa aacatgacct     4875
tccaatgatt gtagtaaatt aacttctata gttcttttgt ctctatatgt attcatatat    4935
atgctattgt atagagactt caaggagaca tggagatgca tgcttattct caggttcatt    4995
cactaaggtg cttggcagac aaccagtttc taagtgcaga atgtagttaa gcagcttcat    5055
atatgtgcca ggcaatttgt tttgttaaat tttcatctac ttaaggaaat agggtattgt    5115
agcttaggct gatcataccc ttcatttcaa ccttaagctc tcaacctgca tccatccgac    5175
ttgagctatt aagtacttta gttttatcga gtataagtta acagaaaaag taaattaagc    5235 tttgcccttta ctatttgaa tttatataca ttctggaaaa acttagaaac tgttgtatat    5295
ttcattagat taaattatat gaaaatgtga ttgtttatag caaagcctgt gagttgcata    5355
```

```
caccctaagg aaaactcctt aagtgctcct tgaagagaga agaaacaatt ctgggtctgg    5415 tcttttttaag aacaaagcta gactactgta tgttagcact gtacattaat agtctgttgt    5475
gaagcttgag cagtttcctg catagccttg atccttcacc gttggcattg aaaatagcag    5535
tatccctgat gtactaaaaa cttaaagtca ggttttggta tatttatttg taagtcttaa    5595
tttcctctaa atactatatc tctttagcga gacaacctga aatttattag cacatttggg    5655
tatctcttgc ttggcattat ggccagtgtt aactattcag tggtgaaaaa attacccctc    5715
aagacactgg agtgacccca gatgtgtgta gtaagtggca tggttcaact gtgtggttaa    5775
tgataaatat atgacttagt cggtatgatc tggaaagact tgattgaaag ataattcagc    5835
tgacataagg atgagtgagg agtggcaaac tggataaaag agtcaagaga cctgtattcc    5895
agtgactcct gttttgttta agcattagca agatctgtct ggggaaactg gatagggcag    5955
ttttcttcca tgtttagttt ttgtctcaac atttggaagc tattgaaggt tttaaaatgg    6015
tgtgtattgt ttttttttgg ggggggggtg gccagaatag tgggtcatct aataaaactg    6075
ccatttaaaa gatcaaaaaa aaaaaaaaaa aaaaaaaa                             6114
```

<210> SEQ ID NO 24
<211> LENGTH: 698
<212> TYPE: PRT
<213> ORGANISM: Mus musculus

<400> SEQUENCE: 24

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240
```

```
Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655
```

```
                    Asp Gly Tyr Gln Gln Asn Phe Lys Arg Gly Ser Gly Gln Ser Gly Pro
                                    660                 665                 670

Arg Gly Ala Pro Arg Gly Arg Gly Gly Pro Pro Arg Pro Asn Arg Gly
                                675                 680                 685

Met Pro Gln Met Asn Thr Gln Gln Val Asn
                        690                 695

<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25
gctggctggc taagtccctc ccgcgccggc tcttgtccca ctaggagcag ctcagagccg      60
cggggacagg gcgaagcggc ctgcgcccac ggagcgcacg tctctgttct caacgcagca     120
ccaccctTgc ccccctcggc tgcccactcc agacgtccac cggctccgcg cgcgcacg      178 atg ccc tcg gcc acc agc cac agc gga agc ggc agc aaa tcg tcg gga     226
Met Pro Ser Ala Thr Ser His Ser Gly Ser Gly Ser Lys Ser Ser Gly
 1               5                  10                  15 ccg ccg ccg ccg tcc ggt tcc tcc ggg agt gag gcg gcg gcc ggg gca     274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag     322
Ala Ala Pro Ala Ser Gln His Pro Ala Thr Gly Thr Gly Ala Val Gln
        35                  40                  45 acc gag gcc atg aag cag att ctc ggc gta atc gac aag aaa ctt cgg     370
Thr Glu Ala Met Lys Gln Ile Leu Gly Val Ile Asp Lys Lys Leu Arg
 50                  55                  60 aac ctg gag aag aaa aag ggt aaa ctt gat gat tac cag gaa cga atg     418
Asn Leu Glu Lys Lys Lys Gly Lys Leu Asp Asp Tyr Gln Glu Arg Met
 65                  70                  75                  80 aat aaa ggg gaa agg ctc aat caa gac cag ctg gat gcc gta tct aag     466
Asn Lys Gly Glu Arg Leu Asn Gln Asp Gln Leu Asp Ala Val Ser Lys
                 85                  90                  95 tac cag gaa gtc aca aat aat ttg gag ttt gca aag gaa tta cag agg     514
Tyr Gln Glu Val Thr Asn Asn Leu Glu Phe Ala Lys Glu Leu Gln Arg
            100                 105                 110 agt ttc atg gca tta agt caa gat att cag aaa aca ata aag aag aca     562
Ser Phe Met Ala Leu Ser Gln Asp Ile Gln Lys Thr Ile Lys Lys Thr
        115                 120                 125 gca cgt cgg gaa cag ctt atg aga gaa gaa gca gaa cag aag cgc tta     610
Ala Arg Arg Glu Gln Leu Met Arg Glu Glu Ala Glu Gln Lys Arg Leu
    130                 135                 140 aaa act gta ctt gag tta cag tat gta ttg gat aag ctg gga gat gat     658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg     706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat     754
Ser Glu Glu Glu Leu Ser Leu Leu Asp Glu Phe Tyr Lys Leu Val Asp
            180                 185                 190 cct gag cgt gac atg agt tta agg tta aat gag cag tat gaa cat gcc     802
Pro Glu Arg Asp Met Ser Leu Arg Leu Asn Glu Gln Tyr Glu His Ala
        195                 200                 205 tca att cac ttg tgg gat ttg ctg gaa ggg aaa gaa aag cct gtg tgt     850
```

```
Ser Ile His Leu Trp Asp Leu Leu Glu Gly Lys Glu Lys Pro Val Cys
    210             215             220 gga aca acc tat aaa gct cta aag gaa att gtt gag cgt gtt ttc cag    898
Gly Thr Thr Tyr Lys Ala Leu Lys Glu Ile Val Glu Arg Val Phe Gln
225             230             235             240 tca aac tac ttt gat agc act cac aat cat caa aat ggg ttg tgt gag    946
Ser Asn Tyr Phe Asp Ser Thr His Asn His Gln Asn Gly Leu Cys Glu
            245             250             255 gag gaa gag gcg gct tca gcg ccc aca gtg gag gac cag gta gct gaa    994
Glu Glu Glu Ala Ala Ser Ala Pro Thr Val Glu Asp Gln Val Ala Glu
        260             265             270 gct gaa cct gag cca gcg gaa gaa tac aca gag caa agt gag gtt gaa    1042
Ala Glu Pro Glu Pro Ala Glu Glu Tyr Thr Glu Gln Ser Glu Val Glu
    275             280             285 tca aca gag tat gtc aat agg cag ttc atg gca gaa aca cag ttc agc    1090
Ser Thr Glu Tyr Val Asn Arg Gln Phe Met Ala Glu Thr Gln Phe Ser
290             295             300 agt ggt gag aag gag caa gtg gat gag tgg aca gtt gaa aca gtt gag    1138
Ser Gly Glu Lys Glu Gln Val Asp Glu Trp Thr Val Glu Thr Val Glu
305             310             315             320 gtt gta aac tca ctc cag cag caa cct cag gct gcg tcc cct tca gtc    1186
Val Val Asn Ser Leu Gln Gln Gln Pro Gln Ala Ala Ser Pro Ser Val
            325             330             335 cca gag ccc cac tct ttg act cca gtg gct cag tca gat cca ctt gtg    1234
Pro Glu Pro His Ser Leu Thr Pro Val Ala Gln Ser Asp Pro Leu Val
        340             345             350 aga agg cag cgt gta caa gat ctt atg gca caa atg caa ggg ccc tat    1282
Arg Arg Gln Arg Val Gln Asp Leu Met Ala Gln Met Gln Gly Pro Tyr
    355             360             365 aat ttc ata cag gat tca atg ttg gat ttt gaa aat cag acg ctt gat    1330
Asn Phe Ile Gln Asp Ser Met Leu Asp Phe Glu Asn Gln Thr Leu Asp
370             375             380 cct gcc att gta tcc gca cag cct atg aac cct acc cag aac atg gat    1378
Pro Ala Ile Val Ser Ala Gln Pro Met Asn Pro Thr Gln Asn Met Asp
385             390             395             400 atg cct cag ctg gtt tgc cct cag gtt cat tct gaa tct aga ctt gcc    1426
Met Pro Gln Leu Val Cys Pro Gln Val His Ser Glu Ser Arg Leu Ala
            405             410             415 caa tct aat caa gtt cct gta caa cca gaa gcc aca cag gtt cct ttg    1474
Gln Ser Asn Gln Val Pro Val Gln Pro Glu Ala Thr Gln Val Pro Leu
        420             425             430 gtt tca tcc aca agt gag ggg tat aca gca tct cag ccc ttg tac cag    1522
Val Ser Ser Thr Ser Glu Gly Tyr Thr Ala Ser Gln Pro Leu Tyr Gln
    435             440             445 cca tct cat gct acg gag cag cgg ccg cag aaa gag cca atg gat cag    1570
Pro Ser His Ala Thr Glu Gln Arg Pro Gln Lys Glu Pro Met Asp Gln
450             455             460 att cag gca aca ata tct ttg aat aca gac cag act aca gca tcc tca    1618
Ile Gln Ala Thr Ile Ser Leu Asn Thr Asp Gln Thr Thr Ala Ser Ser
465             470             475             480 tcc ctt cct gct gct tct cag cct caa gtg ttc cag gct ggg aca agt    1666
Ser Leu Pro Ala Ala Ser Gln Pro Gln Val Phe Gln Ala Gly Thr Ser
            485             490             495 aaa cct ttg cac agc agt gga atc aat gta aat gca gct cca ttc cag    1714
Lys Pro Leu His Ser Ser Gly Ile Asn Val Asn Ala Ala Pro Phe Gln
        500             505             510 tcc atg caa acg gtg ttc aat atg aat gct cca gtc cct cct gct aat    1762
Ser Met Gln Thr Val Phe Asn Met Asn Ala Pro Val Pro Pro Ala Asn
    515             520             525
```

-continued

| | | |
|---|---|---|
| gaa cca gaa acg tta aaa caa cag agt cag tac cag gcc act tat aac<br>Glu Pro Glu Thr Leu Lys Gln Gln Ser Gln Tyr Gln Ala Thr Tyr Asn<br>530                                535                        540 | 1810 |
| cag agt ttt tcc agt cag cct cac caa gtg gaa caa aca gag ctt caa<br>Gln Ser Phe Ser Ser Gln Pro His Gln Val Glu Gln Thr Glu Leu Gln<br>545                                550                        555                        560 | 1858 |
| caa gac caa ctg caa acg gtg gtt ggc act tac cat gga tcc cag gac<br>Gln Asp Gln Leu Gln Thr Val Val Gly Thr Tyr His Gly Ser Gln Asp<br>                        565                        570                        575 | 1906 |
| cag cct cat caa gtg cct ggt aac cac cag caa ccc cca cag cag aac<br>Gln Pro His Gln Val Pro Gly Asn His Gln Gln Pro Pro Gln Gln Asn<br>                        580                        585                        590 | 1954 |
| act ggc ttt cca cgt agc agt cag cct tat tac aac agt cgt ggg gta<br>Thr Gly Phe Pro Arg Ser Ser Gln Pro Tyr Tyr Asn Ser Arg Gly Val<br>                  595                        600                        605 | 2002 |
| tct cga gga ggg tct cgt ggt gcc aga ggc ttg atg aat gga tac agg<br>Ser Arg Gly Gly Ser Arg Gly Ala Arg Gly Leu Met Asn Gly Tyr Arg<br>610                                615                        620 | 2050 |
| ggc cct gcc aat gga ttt aga gga gga tat gat ggt tac cgc cct tca<br>Gly Pro Ala Asn Gly Phe Arg Gly Gly Tyr Asp Gly Tyr Arg Pro Ser<br>625                                630                        635                        640 | 2098 |
| ttc tcg aac act cca aac agt ggt tat tca cag tct cag ttc act gct<br>Phe Ser Asn Thr Pro Asn Ser Gly Tyr Ser Gln Ser Gln Phe Thr Ala<br>                        645                        650                        655 | 2146 |
| ccc cgg gac tac tct ggt tac cag cgg gat gga tat cag cag aat ttc<br>Pro Arg Asp Tyr Ser Gly Tyr Gln Arg Asp Gly Tyr Gln Gln Asn Phe<br>                        660                        665                        670 | 2194 |
| aag cga ggc tct ggg cag agt gga cca cgg gga gcc cca cga ggt aat<br>Lys Arg Gly Ser Gly Gln Ser Gly Pro Arg Gly Ala Pro Arg Gly Asn<br>                        675                        680                        685 | 2242 |
| ata ttg tgg tgg tga cctagctcc tatgtggagc ttctgttctg gccttggaag<br>Ile Leu Trp Trp<br>        690 | 2297 |
| aactgttcat agtccgcatg taggttacat gttaggaata catttatctt ttccagactt | 2357 |
| gttgctaaag attaaatgaa atgctctgtt tctaaaattt catcttgaat ccaaattta | 2417 |
| attttgaat gactttccct gctgttgtct tcaaaatcag aacatttcct ctgcctcaga | 2477 |
| aaagcgtttt tccaactgga aatttatttt tcaggtctta aaacctgcta aatgtttta | 2537 |
| ggaagtacct actgaaactt tttgtaagac atttttggaa cgagcttgaa catttatata | 2597 |
| aatttattac cctctttgat ttttgaaaca tgcatattat atttaggctg agaagccctt | 2657 |
| caaatggcca gataagccac agttttagct agagaaccat ttagaattga cataactaat | 2717 |
| ctaaacttga acacttttag gaccaatgtt agtgttctaa ataccaacat atttctgatg | 2777 |
| tttaaacaga tctcccaaat tcttaggacc ttgatgtcat taaaatttag aatgacaagc | 2837 |
| ttaagaggct ttagtttcat ttgttttttca agtaatgaaa aataatttct tacatgggca | 2897 |
| gatagttaat ttgttgaaca attacaggta gcatttcatg taatctgatg ttctaaatgg | 2957 |
| ttctcttatt gaaggaggtt aaagaattag gtttcttaca gttttttggct ggccatgaca | 3017 |
| tgtataaaat gtatattaag gaggaattat aaagtacttt aatttgaatg ctagtggcaa | 3077 |
| ttgatcatta agaaagtact ttaaagcaaa aggttaatgg gtcatctggg aaaaatactg | 3137 |
| aagtatcaaa ggtatttgca tgtgaatgtg ggttatgttc ttctatccca ccttgtagca | 3197 |
| tattctatga aagttgagtt aaatgatagc taaaatatct gtttcaacag catgtaaaaa | 3257 |
| gttatttaa ctgttacaag tcattataca atttttgaatg ttctgtagtt tcttttaac | 3317 |
| agtttaggta caaaggtctg ttttcattct ggtgcttttt attaattttg atagtatgat | 3377 |

-continued

```
gtcacttcct attgaaatgt aagctagcgt gtaccttaga atgtgagctc catgagagca   3437
ggtaccttgt ttgtcttcac tgctgtatct attcccaacg cctcatgaca gtgcctggca   3497
catagtaggc actcaataaa tacttgttga atgaatgaaa aaaaaaaaaa a            3548

<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
```

```
                    340                 345                 350
Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
        370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690

<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27
```

```
cccaccgcgc gcgcgcgtag ccgcctgccc gcccgcccgc tgcgcgtttt gtcccgcgtc        60 tctcccgtc cgtctcctga cttgctggtc ttgtccttcc ctcccgcttt tttcctctcc        120
tctcttctcg gtctaaag atg ccc tcg gcc acc agc cac agc gga agc ggc        171
                    Met Pro Ser Ala Thr Ser His Ser Gly Ser Gly
                     1           5                    10 agc aaa tcg tcg gga ccg ccg ccg tcc ggt tcc tcc ggg agt gag            219
Ser Lys Ser Ser Gly Pro Pro Pro Ser Gly Ser Ser Gly Ser Glu
         15              20              25 gcg gcg gcc ggg gca gct gcg ccg gct tct cag cat ccg gca acc ggc        267
Ala Ala Ala Gly Ala Ala Ala Pro Ala Ser Gln His Pro Ala Thr Gly
             30              35              40 acc ggc gcc gtc cag acc gag gcc atg aag cag att ctc ggc gta atc        315
Thr Gly Ala Val Gln Thr Glu Ala Met Lys Gln Ile Leu Gly Val Ile
         45              50              55 gac aag aaa ctt cgg aac ctg gag aag aaa aag ggt aaa ctt gat gat        363
Asp Lys Lys Leu Arg Asn Leu Glu Lys Lys Lys Gly Lys Leu Asp Asp
 60              65              70                      75 tac cag gaa cga atg aat aaa ggg gaa agg ctc aat caa gac cag ctg        411
Tyr Gln Glu Arg Met Asn Lys Gly Glu Arg Leu Asn Gln Asp Gln Leu
                 80              85                  90 gat gcc gta tct aag tac cag gaa gtc aca aat aat ttg gag ttt gca        459
Asp Ala Val Ser Lys Tyr Gln Glu Val Thr Asn Asn Leu Glu Phe Ala
             95              100             105 aag gaa tta cag agg agt ttc atg gca tta agt caa gat att cag aaa        507
Lys Glu Leu Gln Arg Ser Phe Met Ala Leu Ser Gln Asp Ile Gln Lys
         110             115             120 aca ata aag aag aca gca cgt cgg gaa cag ctt atg aga gaa gaa gca        555
Thr Ile Lys Lys Thr Ala Arg Arg Glu Gln Leu Met Arg Glu Glu Ala
     125             130             135 gaa cag aag cgc tta aaa act gta ctt gag tta cag tat gta ttg gat        603
Glu Gln Lys Arg Leu Lys Thr Val Leu Glu Leu Gln Tyr Val Leu Asp
140             145             150             155 aag ctg gga gat gat gat gtg aga aca gat ctg aaa caa ggt ttg agt        651
Lys Leu Gly Asp Asp Asp Val Arg Thr Asp Leu Lys Gln Gly Leu Ser
             160             165                 170 gga gtg cca ata ttg tct gag gag gag ttg tca ttg ctg gat gag ttc        699
Gly Val Pro Ile Leu Ser Glu Glu Glu Leu Ser Leu Leu Asp Glu Phe
         175             180             185 tac aag ctc gta gat cct gag cgt gac atg agt tta agg tta aat gag        747
Tyr Lys Leu Val Asp Pro Glu Arg Asp Met Ser Leu Arg Leu Asn Glu
     190             195             200 cag tat gaa cat gcc tca att cac ttg tgg gat ttg ctg gaa ggg aaa        795
Gln Tyr Glu His Ala Ser Ile His Leu Trp Asp Leu Leu Glu Gly Lys
205             210             215 gaa aag cct gtg tgt gga aca acc tat aaa gct cta aag gaa att gtt        843
Glu Lys Pro Val Cys Gly Thr Thr Tyr Lys Ala Leu Lys Glu Ile Val
220             225             230             235 gag cgt gtt ttc cag tca aac tac ttt gat agc act cac aat cat caa        891
Glu Arg Val Phe Gln Ser Asn Tyr Phe Asp Ser Thr His Asn His Gln
             240             245             250 aat ggg ttg tgt gag gag gaa gag gcg gct tca gcg ccc aca gtg gag        939
Asn Gly Leu Cys Glu Glu Glu Glu Ala Ala Ser Ala Pro Thr Val Glu
         255             260             265 gac cag gta gct gaa gct gaa cct gag cca gcg gaa gaa tac aca gag        987
Asp Gln Val Ala Glu Ala Glu Pro Glu Pro Ala Glu Glu Tyr Thr Glu
     270             275             280 caa agt gag gtt gaa tca aca gag tat gtc aat agg cag ttc atg gca       1035
Gln Ser Glu Val Glu Ser Thr Glu Tyr Val Asn Arg Gln Phe Met Ala
285             290             295
```

```
gaa aca cag ttc agc agt ggt gag aag gag caa gtg gat gag tgg aca    1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct    1131
Val Glu Thr Val Glu Val Val Asn Ser Leu Gln Gln Gln Pro Gln Ala
            320                 325                 330 gcg tcc cct tca gtc cca gag ccc cac tct ttg act cca gtg gct cag    1179
Ala Ser Pro Ser Val Pro Glu Pro His Ser Leu Thr Pro Val Ala Gln
                335                 340                 345 tca gat cca ctt gtg aga agg cag cgt gta caa gat ctt atg gca caa    1227
Ser Asp Pro Leu Val Arg Arg Gln Arg Val Gln Asp Leu Met Ala Gln
        350                 355                 360 atg caa ggg ccc tat aat ttc ata cag gat tca atg ttg gat ttt gaa    1275
Met Gln Gly Pro Tyr Asn Phe Ile Gln Asp Ser Met Leu Asp Phe Glu
    365                 370                 375 aat cag acg ctt gat cct gcc att gta tcc gca cag cct atg aac cct    1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct    1371
Thr Gln Asn Met Asp Met Pro Gln Leu Val Cys Pro Gln Val His Ser
            400                 405                 410 gaa tct aga ctt gcc caa tct aat caa gtt cct gta caa cca gaa gcc    1419
Glu Ser Arg Leu Ala Gln Ser Asn Gln Val Pro Val Gln Pro Glu Ala
                415                 420                 425 aca cag gtt cct ttg gtt tca tcc aca agt gag ggg tat aca gca tct    1467
Thr Gln Val Pro Leu Val Ser Ser Thr Ser Glu Gly Tyr Thr Ala Ser
        430                 435                 440 cag ccc ttg tac cag cca tct cat gct acg gag cag cgg ccg cag aaa    1515
Gln Pro Leu Tyr Gln Pro Ser His Ala Thr Glu Gln Arg Pro Gln Lys
    445                 450                 455 gag cca atg gat cag att cag gca aca ata tct ttg aat aca gac cag    1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc    1611
Thr Thr Ala Ser Ser Ser Leu Pro Ala Ala Ser Gln Pro Gln Val Phe
            480                 485                 490 cag gct ggg aca agt aaa cct ttg cac agc agt gga atc aat gta aat    1659
Gln Ala Gly Thr Ser Lys Pro Leu His Ser Ser Gly Ile Asn Val Asn
                495                 500                 505 gca gct cca ttc cag tcc atg caa acg gtg ttc aat atg aat gct cca    1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac    1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa    1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac    1851
Gln Thr Glu Leu Gln Gln Asp Gln Leu Gln Thr Val Val Gly Thr Tyr
            560                 565                 570 cat gga tcc cag gac cag cct cat caa gtg cct ggt aac cac cag caa    1899
His Gly Ser Gln Asp Gln Pro His Gln Val Pro Gly Asn His Gln Gln
                575                 580                 585 ccc cca cag cag aac act ggc ttt cca cgt agc agt cag cct tat tac    1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg    1995
Asn Ser Arg Gly Val Ser Arg Gly Gly Ser Arg Gly Ala Arg Gly Leu
```

```
                605               610              615
atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620             625                 630                 635 ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
                655                 660                 665 tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
                670                 675                 680 gcc cca cga ggt aat ata ttg tgg tgg tga tcctagctcc tatgtggagc        2237
Ala Pro Arg Gly Asn Ile Leu Trp Trp
    685                 690 ttctgttctg gccttggaag aactgttcat agtccgcatg taggttacat gttaggaata    2297
catttatctt ttccagactt gttgctaaag attaaatgaa atgctctgtt tctaaaattt    2357
catcttgaat ccaaatttta attttgaat gactttccct gctgttgtct tcaaaatcag     2417
aacattttct ctgcctcaga aaagcgtttt tccaactgga aatttatttt tcaggtctta    2477
aaacctgcta atgttttta ggaagtacct actgaaactt tttgtaagac attttggaa      2537 cgagcttgaa catttatata aatttattac cctctttgat ttttgaaaca tgcatattat    2597
atttaggctg agaagccctt caaatggcca gataagccac agttttagct agagaaccat    2657
ttagaattga cataactaat ctaaacttga acacttttag gaccaatgtt agtgttctaa    2717
ataccaacat atttctgatg tttaaacaga tctcccaaat tcttaggacc ttgatgtcat    2777
taaaatttag aatgacaagc ttaagaggct ttagtttcat ttgttttttca agtaatgaaa   2837 aataatttct tacatgggca gatagttaat ttgttgaaca attacaggta gcatttcatg    2897
taatctgatg ttctaaatgg ttctcttatt gaaggaggtt aaagaattag gtttcttaca    2957 gttttttggct ggccatgaca tgtataaaat gtatattaag gaggaattat aaagtacttt   3017
aatttgaatg ctagtggcaa ttgatcatta agaaagtact ttaaagcaaa aggttaatgg    3077
gtcatctggg aaaaatactg aagtatcaaa ggtatttgca tgtgaatgtg ggttatgttc    3137
ttctatccca ccttgtagca tattctatga agttgagtt aaatgatagc taaaatatct    3197
gtttcaacag catgtaaaaa gttatttaa ctgttacaag tcattataca attttgaatg     3257
ttctgtagtt tctttttaac agtttaggta caaaggtctg ttttcattct ggtgcttttt    3317
attaattttg atagtatgat gtcacttcct attgaaatgt aagctagcgt gtaccttaga    3377
atgtgagctc catgagagca ggtaccttgt ttgtcttcac tgctgtatct attcccaacg    3437
cctcatgaca gtgcctggca catagtaggc actcaataaa tacttgttga atgaatgaaa    3497 aaaaaaaaa a                                                          3508

<210> SEQ ID NO 28
<211> LENGTH: 692
<212> TYPE: PRT
<213> ORGANISM: Mus musculus

<400> SEQUENCE: 28

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30
```

-continued

```
Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Ala Glu Gln Lys Arg Leu
        130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
        210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445
```

```
Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Pro Gln Gln Asn
            580                 585                 590

Thr Gly Phe Pro Arg Ser Ser Gln Pro Tyr Tyr Asn Ser Arg Gly Val
    595                 600                 605

Ser Arg Gly Gly Ser Arg Gly Ala Arg Gly Leu Met Asn Gly Tyr Arg
610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690

<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)

<400> SEQUENCE: 29 atg ccc tcg gct acc aac ggc acc atg gcg agc agc agc ggg aag gcg      48
Met Pro Ser Ala Thr Asn Gly Thr Met Ala Ser Ser Ser Gly Lys Ala
1               5                   10                  15 ggc ccg ggc ggc aac gag cag gcc ccg gcg gcg gca gcg gcg gcc ccg      96
Gly Pro Gly Gly Asn Glu Gln Ala Pro Ala Ala Ala Ala Ala Ala Pro
            20                  25                  30 cag gcg tcg ggc ggc agc atc acc tcg gtt cag acc gag gcc atg aag     144
Gln Ala Ser Gly Gly Ser Ile Thr Ser Val Gln Thr Glu Ala Met Lys
        35                  40                  45 cag atc ttg gga gtg atc gac aaa aag ctc cgc aac ctc gag aag aaa     192
Gln Ile Leu Gly Val Ile Asp Lys Lys Leu Arg Asn Leu Glu Lys Lys
    50                  55                  60 aag agc aaa ctt gac gat tac cag gaa cga atg aac aag ggg gaa cgt     240
Lys Ser Lys Leu Asp Asp Tyr Gln Glu Arg Met Asn Lys Gly Glu Arg
65                  70                  75                  80
```

```
cta aat caa gat caa ctg gat gca gtg tca aaa tac cag gaa gtg aca    288
Leu Asn Gln Asp Gln Leu Asp Ala Val Ser Lys Tyr Gln Glu Val Thr
             85                  90                  95 aat aac ctg gaa ttc gct aaa gaa ctg cag agg agc ttt atg gca ctg    336
Asn Asn Leu Glu Phe Ala Lys Glu Leu Gln Arg Ser Phe Met Ala Leu
        100                 105                 110 agc caa gat atc cag aaa aca ata aaa aag acg gct cgc agg gag cag    384
Ser Gln Asp Ile Gln Lys Thr Ile Lys Lys Thr Ala Arg Arg Glu Gln
        115                 120                 125 ctg atg aga gaa gag gct gag cag aag cgt tta aag act gtg cta gag    432
Leu Met Arg Glu Glu Ala Glu Gln Lys Arg Leu Lys Thr Val Leu Glu
130                 135                 140 ctg cag ttc att ttg gac aag ttg ggt gac gat gaa gtg cgc agt gac    480
Leu Gln Phe Ile Leu Asp Lys Leu Gly Asp Asp Glu Val Arg Ser Asp
145                 150                 155                 160 ttg aaa caa gga tca aat gga gta ccg gta ctg aca gag gag gaa ctg    528
Leu Lys Gln Gly Ser Asn Gly Val Pro Val Leu Thr Glu Glu Glu Leu
                165                 170                 175 aca atg ctg gat gaa ttt tac aag cta gtt tac cct gaa agg gac atg    576
Thr Met Leu Asp Glu Phe Tyr Lys Leu Val Tyr Pro Glu Arg Asp Met
            180                 185                 190 aac atg agg ttg aat gag cag tat gag caa gca tct gtt cac ctg tgg    624
Asn Met Arg Leu Asn Glu Gln Tyr Glu Gln Ala Ser Val His Leu Trp
        195                 200                 205 gac tta ctg gaa ggg aag gaa aaa ccc gtt tgt gga aca acc tat aaa    672
Asp Leu Leu Glu Gly Lys Glu Lys Pro Val Cys Gly Thr Thr Tyr Lys
        210                 215                 220 gcc ctg aag gag gtt gtt gaa cgt att ctt caa act agt tac ttt gat    720
Ala Leu Lys Glu Val Val Glu Arg Ile Leu Gln Thr Ser Tyr Phe Asp
225                 230                 235                 240 agc acc cat aac cat cag aac ggg tta tgt gag gaa gaa gag gca gca    768
Ser Thr His Asn His Gln Asn Gly Leu Cys Glu Glu Glu Glu Ala Ala
                245                 250                 255 ccc aca cct gca gta gaa gac act gta gca gaa gct gag cct gat cca    816
Pro Thr Pro Ala Val Glu Asp Thr Val Ala Glu Ala Glu Pro Asp Pro
            260                 265                 270 gca gaa gaa ttt act gaa cct act gaa gtt gaa tcg act gag tat gta    864
Ala Glu Glu Phe Thr Glu Pro Thr Glu Val Glu Ser Thr Glu Tyr Val
        275                 280                 285 aac aga caa ttc atg gca gag act cag ttc agc agt agt gag aag gaa    912
Asn Arg Gln Phe Met Ala Glu Thr Gln Phe Ser Ser Ser Glu Lys Glu
        290                 295                 300 cag gta gat gag tgg aca gtt gaa acg gtt gag gtt gta aat tca ctg    960
Gln Val Asp Glu Trp Thr Val Glu Thr Val Glu Val Val Asn Ser Leu
305                 310                 315                 320 cag caa caa aca caa gct aca tct cct cca gtt cct gaa cct cat aca   1008
Gln Gln Gln Thr Gln Ala Thr Ser Pro Pro Val Pro Glu Pro His Thr
                325                 330                 335 ctc act act gtg gct caa gca gat cct ctt gtt aga aga cag aga gta   1056
Leu Thr Thr Val Ala Gln Ala Asp Pro Leu Val Arg Arg Gln Arg Val
            340                 345                 350 cag gac ctt atg gcc cag atg cag ggt cca tat aac ttc atg cag gac   1104
Gln Asp Leu Met Ala Gln Met Gln Gly Pro Tyr Asn Phe Met Gln Asp
        355                 360                 365 tct atg ctg gag ttt gag aac cag aca ctt gat cct gcc att gta tct   1152
Ser Met Leu Glu Phe Glu Asn Gln Thr Leu Asp Pro Ala Ile Val Ser
        370                 375                 380 gca cag ccc atg aat cca gca cag aat ttg gac atg ccg caa atg gtc   1200
Ala Gln Pro Met Asn Pro Ala Gln Asn Leu Asp Met Pro Gln Met Val
385                 390                 395                 400
```

```
                                        -continued tgc cct cca gtt cat act gag tca aga ctt gcc cag cct aat caa gtt      1248
Cys Pro Pro Val His Thr Glu Ser Arg Leu Ala Gln Pro Asn Gln Val
            405                 410                 415 cct gtg caa cca gaa gct acg cag gtt ccc ttg gtt tca tct aca agt      1296
Pro Val Gln Pro Glu Ala Thr Gln Val Pro Leu Val Ser Ser Thr Ser
        420                 425                 430 gag gga tat aca gcc tcc cag ccc atg tat cag cct tct cat acc aca      1344
Glu Gly Tyr Thr Ala Ser Gln Pro Met Tyr Gln Pro Ser His Thr Thr
    435                 440                 445 gag caa cgg cca cag aag gaa tcc att gac cag att cag gct tca atg      1392
Glu Gln Arg Pro Gln Lys Glu Ser Ile Asp Gln Ile Gln Ala Ser Met
450                 455                 460 tca ctg aat gca gac cag acc ccg tca tca tca ctt ccc act gca          1440
Ser Leu Asn Ala Asp Gln Thr Pro Ser Ser Ser Leu Pro Thr Ala
465                 470                 475                 480 tcc cag ccg caa gtt ttc caa gct gga tct agc aaa cct ttg cat agc      1488
Ser Gln Pro Gln Val Phe Gln Ala Gly Ser Ser Lys Pro Leu His Ser
                485                 490                 495 agc gga atc aat gtt aat gca gct cca ttc caa tcc atg caa aca gta      1536
Ser Gly Ile Asn Val Asn Ala Ala Pro Phe Gln Ser Met Gln Thr Val
            500                 505                 510 ttc aac atg aat gca cct gtt cct cct gtt aat gag cca gaa gcc ctt      1584
Phe Asn Met Asn Ala Pro Val Pro Pro Val Asn Glu Pro Glu Ala Leu
        515                 520                 525 aag caa caa aat cag tac cag gcc agt tac aac cag agt ttc tcc aat      1632
Lys Gln Gln Asn Gln Tyr Gln Ala Ser Tyr Asn Gln Ser Phe Ser Asn
    530                 535                 540 cag cca cac caa gta gaa caa tca gat ctt cag caa gaa cag ctc cag      1680
Gln Pro His Gln Val Glu Gln Ser Asp Leu Gln Gln Glu Gln Leu Gln
545                 550                 555                 560 aca gtg gtt ggt act tac cat ggt tct ccg gac cag acc cat caa gtg      1728
Thr Val Val Gly Thr Tyr His Gly Ser Pro Asp Gln Thr His Gln Val
                565                 570                 575 gca gga aac cac cag caa cct ccc cag cag aat act gga ttt cca cgc      1776
Ala Gly Asn His Gln Gln Pro Pro Gln Gln Asn Thr Gly Phe Pro Arg
            580                 585                 590 aac agt cag cct tat tac aac agt cgg gga gtg tct cgt ggt gga tca      1824
Asn Ser Gln Pro Tyr Tyr Asn Ser Arg Gly Val Ser Arg Gly Gly Ser
        595                 600                 605 cgt ggg act cgt gga ttg atg aat ggt tac agg gga cct gca aat gga      1872
Arg Gly Thr Arg Gly Leu Met Asn Gly Tyr Arg Gly Pro Ala Asn Gly
    610                 615                 620 ttt aga gga gga tat gat ggc tac cgt cct tca ttt tcc aac act ccg      1920
Phe Arg Gly Gly Tyr Asp Gly Tyr Arg Pro Ser Phe Ser Asn Thr Pro
625                 630                 635                 640 aac agt ggt tac acg cag ccc caa ttt aat gct cct cga gat tat tca      1968
Asn Ser Gly Tyr Thr Gln Pro Gln Phe Asn Ala Pro Arg Asp Tyr Ser
                645                 650                 655 aac tac cag cgg gat gga tat cag cag aac ttc aaa cgt ggt tct gga      2016
Asn Tyr Gln Arg Asp Gly Tyr Gln Gln Asn Phe Lys Arg Gly Ser Gly
            660                 665                 670 caa agt ggg cct cgg gga gct cct cga ggt cgt gga ggg ccc cca aga      2064
Gln Ser Gly Pro Arg Gly Ala Pro Arg Gly Arg Gly Gly Pro Pro Arg
        675                 680                 685 cca aac aga ggg atg cct caa atg aac gct cag caa gtg aat taa          2109
Pro Asn Arg Gly Met Pro Gln Met Asn Ala Gln Gln Val Asn
    690                 695                 700

<210> SEQ ID NO 30
```

```
<211> LENGTH: 702
<212> TYPE: PRT
<213> ORGANISM: Gallus gallus

<400> SEQUENCE: 30
```

| | | | | | | | | | | | | | | |
|---|---|---|---|---|---|---|---|---|---|---|---|---|---|---|
| Met | Pro | Ser | Ala | Thr | Asn | Gly | Thr | Met | Ala | Ser | Ser | Gly | Lys | Ala |
| 1 | | | | 5 | | | | | 10 | | | | | 15 |
| Gly | Pro | Gly | Gly | Asn | Glu | Gln | Ala | Pro | Ala | Ala | Ala | Ala | Ala | Pro |
| | | | 20 | | | | | 25 | | | | | 30 | |
| Gln | Ala | Ser | Gly | Gly | Ser | Ile | Thr | Ser | Val | Gln | Thr | Glu | Ala | Met | Lys |
| | | 35 | | | | | 40 | | | | | 45 | | | |
| Gln | Ile | Leu | Gly | Val | Ile | Asp | Lys | Lys | Leu | Arg | Asn | Leu | Glu | Lys | Lys |
| 50 | | | | | 55 | | | | | 60 | | | | | |
| Lys | Ser | Lys | Leu | Asp | Asp | Tyr | Gln | Glu | Arg | Met | Asn | Lys | Gly | Glu | Arg |
| 65 | | | | | 70 | | | | | 75 | | | | | 80 |
| Leu | Asn | Gln | Asp | Gln | Leu | Asp | Ala | Val | Ser | Lys | Tyr | Gln | Glu | Val | Thr |
| | | | | 85 | | | | | 90 | | | | | 95 | |
| Asn | Asn | Leu | Glu | Phe | Ala | Lys | Glu | Leu | Gln | Arg | Ser | Phe | Met | Ala | Leu |
| | | | 100 | | | | | 105 | | | | | 110 | | |
| Ser | Gln | Asp | Ile | Gln | Lys | Thr | Ile | Lys | Lys | Thr | Ala | Arg | Arg | Glu | Gln |
| | | 115 | | | | | 120 | | | | | 125 | | | |
| Leu | Met | Arg | Glu | Glu | Ala | Glu | Gln | Lys | Arg | Leu | Lys | Thr | Val | Leu | Glu |
| 130 | | | | | 135 | | | | | 140 | | | | | |
| Leu | Gln | Phe | Ile | Leu | Asp | Lys | Leu | Gly | Asp | Asp | Glu | Val | Arg | Ser | Asp |
| 145 | | | | | 150 | | | | | 155 | | | | | 160 |
| Leu | Lys | Gln | Gly | Ser | Asn | Gly | Val | Pro | Val | Leu | Thr | Glu | Glu | Leu |
| | | | | 165 | | | | | 170 | | | | | 175 |
| Thr | Met | Leu | Asp | Glu | Phe | Tyr | Lys | Leu | Val | Tyr | Pro | Glu | Arg | Asp | Met |
| | | | 180 | | | | | 185 | | | | | 190 | | |
| Asn | Met | Arg | Leu | Asn | Glu | Gln | Tyr | Glu | Gln | Ala | Ser | Val | His | Leu | Trp |
| | | 195 | | | | | 200 | | | | | 205 | | | |
| Asp | Leu | Leu | Glu | Gly | Lys | Glu | Lys | Pro | Val | Cys | Gly | Thr | Thr | Tyr | Lys |
| 210 | | | | | 215 | | | | | 220 | | | | | |
| Ala | Leu | Lys | Glu | Val | Val | Glu | Arg | Ile | Leu | Gln | Thr | Ser | Tyr | Phe | Asp |
| 225 | | | | | 230 | | | | | 235 | | | | | 240 |
| Ser | Thr | His | Asn | His | Gln | Asn | Gly | Leu | Cys | Glu | Glu | Glu | Ala | Ala |
| | | | | 245 | | | | | 250 | | | | | 255 |
| Pro | Thr | Pro | Ala | Val | Glu | Asp | Thr | Val | Ala | Glu | Ala | Glu | Pro | Asp | Pro |
| | | | 260 | | | | | 265 | | | | | 270 | | |
| Ala | Glu | Glu | Phe | Thr | Glu | Pro | Thr | Glu | Val | Ser | Thr | Glu | Tyr | Val |
| | | 275 | | | | | 280 | | | | | 285 | | |
| Asn | Arg | Gln | Phe | Met | Ala | Glu | Thr | Gln | Phe | Ser | Ser | Ser | Glu | Lys | Glu |
| | 290 | | | | | 295 | | | | | 300 | | | | |
| Gln | Val | Asp | Glu | Trp | Thr | Val | Glu | Thr | Val | Glu | Val | Asn | Ser | Leu |
| 305 | | | | | 310 | | | | | 315 | | | | | 320 |
| Gln | Gln | Gln | Thr | Gln | Ala | Thr | Ser | Pro | Val | Pro | Glu | Pro | His | Thr |
| | | | | 325 | | | | | 330 | | | | | 335 |
| Leu | Thr | Thr | Val | Ala | Gln | Ala | Asp | Pro | Leu | Val | Arg | Arg | Gln | Arg | Val |
| | | | 340 | | | | | 345 | | | | | 350 | | |
| Gln | Asp | Leu | Met | Ala | Gln | Met | Gln | Gly | Pro | Tyr | Asn | Phe | Met | Gln | Asp |
| | | 355 | | | | | 360 | | | | | 365 | | | |
| Ser | Met | Leu | Glu | Phe | Glu | Asn | Gln | Thr | Leu | Asp | Pro | Ala | Ile | Val | Ser |
| 370 | | | | | 375 | | | | | 380 | | | | | |
| Ala | Gln | Pro | Met | Asn | Pro | Ala | Gln | Asn | Leu | Asp | Met | Pro | Gln | Met | Val |

-continued

```
            385                 390                 395                 400

Cys Pro Pro Val His Thr Glu Ser Arg Leu Ala Gln Pro Asn Gln Val
                        405                 410                 415

Pro Val Gln Pro Glu Ala Thr Gln Val Pro Leu Val Ser Ser Thr Ser
                        420                 425                 430

Glu Gly Tyr Thr Ala Ser Gln Pro Met Tyr Gln Pro Ser His Thr Thr
                        435                 440                 445

Glu Gln Arg Pro Gln Lys Glu Ser Ile Asp Gln Ile Gln Ala Ser Met
                        450                 455                 460

Ser Leu Asn Ala Asp Gln Thr Pro Ser Ser Ser Leu Pro Thr Ala
        465                 470                 475                 480

Ser Gln Pro Gln Val Phe Gln Ala Gly Ser Ser Lys Pro Leu His Ser
                        485                 490                 495

Ser Gly Ile Asn Val Asn Ala Ala Pro Phe Gln Ser Met Gln Thr Val
                        500                 505                 510

Phe Asn Met Asn Ala Pro Val Pro Pro Val Asn Glu Pro Glu Ala Leu
                        515                 520                 525

Lys Gln Gln Asn Gln Tyr Gln Ala Ser Tyr Asn Gln Ser Phe Ser Asn
                        530                 535                 540

Gln Pro His Gln Val Glu Gln Ser Asp Leu Gln Gln Glu Gln Leu Gln
        545                 550                 555                 560

Thr Val Val Gly Thr Tyr His Gly Ser Pro Asp Gln Thr His Gln Val
                        565                 570                 575

Ala Gly Asn His Gln Gln Pro Pro Gln Gln Asn Thr Gly Phe Pro Arg
                        580                 585                 590

Asn Ser Gln Pro Tyr Tyr Asn Ser Arg Gly Val Ser Arg Gly Gly Ser
                        595                 600                 605

Arg Gly Thr Arg Gly Leu Met Asn Gly Tyr Arg Gly Pro Ala Asn Gly
                        610                 615                 620

Phe Arg Gly Gly Tyr Asp Gly Tyr Arg Pro Ser Phe Ser Asn Thr Pro
        625                 630                 635                 640

Asn Ser Gly Tyr Thr Gln Pro Gln Phe Asn Ala Pro Arg Asp Tyr Ser
                        645                 650                 655

Asn Tyr Gln Arg Asp Gly Tyr Gln Gln Asn Phe Lys Arg Gly Ser Gly
                        660                 665                 670

Gln Ser Gly Pro Arg Gly Ala Pro Arg Gly Arg Gly Pro Pro Arg
                        675                 680                 685

Pro Asn Arg Gly Met Pro Gln Met Asn Ala Gln Gln Val Asn
            690                 695                 700

<210> SEQ ID NO 31
<211> LENGTH: 20
<212> TYPE: DNA
<213> ORGANISM: Artificial
<220> FEATURE:
<223> OTHER INFORMATION: T3 primer

<400> SEQUENCE: 31
aattaaccct cactaaaggg                                                    20

<210> SEQ ID NO 32
<211> LENGTH: 19
<212> TYPE: DNA
<213> ORGANISM: Artificial
<220> FEATURE:
<223> OTHER INFORMATION: T7 primer
```

```
<400> SEQUENCE: 32
taatacgact cactatagg                                             19

<210> SEQ ID NO 33
<211> LENGTH: 18
<212> TYPE: DNA
<213> ORGANISM: Artificial
<220> FEATURE:
<223> OTHER INFORMATION: Synthetic primer

<400> SEQUENCE: 33
aaggtttgaa tggagtgc                                              18

<210> SEQ ID NO 34
<211> LENGTH: 18
<212> TYPE: DNA
<213> ORGANISM: Artificial
<220> FEATURE:
<223> OTHER INFORMATION: Synthetic primer

<400> SEQUENCE: 34
tgctcctttt caccactg                                              18

<210> SEQ ID NO 35
<211> LENGTH: 18
<212> TYPE: DNA
<213> ORGANISM: Artificial
<220> FEATURE:
<223> OTHER INFORMATION: GAPDH primer

<400> SEQUENCE: 35
gggctgcttt taactctg                                              18

<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36
ccaggaaatg agcttgac                                              18

<210> SEQ ID NO 37
<211> LENGTH: 18
<212> TYPE: PRT
<213> ORGANISM: Artificial
<220> FEATURE:
<223> OTHER INFORMATION: Synthetic peptide

<400> SEQUENCE: 37

Pro Pro Val Asn Glu Pro Glu Thr Leu Lys Gln Gln Asn Gln Tyr Gln
1               5                   10                  15

Ala Ser

<210> SEQ ID NO 38
<211> LENGTH: 22
<212> TYPE: DNA
<213> ORGANISM: Artificial
<220> FEATURE:
<223> OTHER INFORMATION: Synthetic primer

<400> SEQUENCE: 38
aggtsharct gcagsagtcw gg                                         22
```

```
<210> SEQ ID NO 39
<211> LENGTH: 23
<212> TYPE: DNA
<213> ORGANISM: Artificial
<220> FEATURE:
<223> OTHER INFORMATION: Synthetic primer

<400> SEQUENCE: 39
ctcgagttaa ttcacttgct gag                                              23

<210> SEQ ID NO 40
<211> LENGTH: 5
<212> TYPE: PRT
<213> ORGANISM: Gallus gallus

<400> SEQUENCE: 40

Gly Tyr Asp Met Leu
1               5

<210> SEQ ID NO 41
<211> LENGTH: 17
<212> TYPE: PRT
<213> ORGANISM: Gallus gallus

<400> SEQUENCE: 41

Gly Ile Gly Ser Thr Gly Gly Thr Asp Tyr Gly Ala Ala Val Lys
1               5                   10                  15

Gly

<210> SEQ ID NO 42
<211> LENGTH: 19
<212> TYPE: PRT
<213> ORGANISM: Gallus gallus

<400> SEQUENCE: 42

Val Ala Gly Gly Cys Asn Ser Gly Tyr Cys Arg Asp Ser Pro Gly Ser
1               5                   10                  15

Ile Asp Ala

<210> SEQ ID NO 43
<211> LENGTH: 127
<212> TYPE: PRT
<213> ORGANISM: Gallus gallus

<400> SEQUENCE: 43

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Gly Tyr
            20                  25                  30

Asp Met Leu Trp Val Arg Gln Ala Pro Gly Lys Gly Leu Glu Trp Val
        35                  40                  45

Ala Gly Ile Gly Ser Thr Gly Gly Thr Asp Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Val Ala Gly Gly Cys Asn Ser Gly Tyr Cys Arg Asp Ser Pro
            100                 105                 110

Gly Ser Ile Asp Ala Trp Gly His Gly Thr Glu Val Ile Val Ser
```

<210> SEQ ID NO 44
<211> LENGTH: 10
<212> TYPE: PRT
<213> ORGANISM: Gallus gallus

<400> SEQUENCE: 44

Ser Gly Gly Gly Ser Arg Asn Tyr Tyr Gly
1               5                   10

<210> SEQ ID NO 45
<211> LENGTH: 7
<212> TYPE: PRT
<213> ORGANISM: Gallus gallus

<400> SEQUENCE: 45

Asp Asp Gln Arg Pro Ser Asn
1               5

<210> SEQ ID NO 46
<211> LENGTH: 11
<212> TYPE: PRT
<213> ORGANISM: Gallus gallus

<400> SEQUENCE: 46

Ser Ala Asp Ser Asn Thr Tyr Glu Gly Ser Phe
1               5                   10

<210> SEQ ID NO 47
<211> LENGTH: 107
<212> TYPE: PRT
<213> ORGANISM: Gallus gallus

<400> SEQUENCE: 47

Ala Val Thr Gln Gln Pro Ala Ser Val Ser Ala Asn Pro Gly Glu Thr
1               5                   10                  15

Val Lys Ile Thr Cys Ser Gly Gly Ser Arg Asn Tyr Tyr Gly Trp
            20                  25                  30

Tyr Gln Gln Lys Ser Pro Gly Ser Val Pro Val Thr Val Ile Tyr Tyr
            35                  40                  45

Asp Asp Gln Arg Pro Ser Asn Ile Pro Ser Arg Phe Ser Gly Ala Leu
    50                  55                  60

Ser Gly Ser Thr Ser Thr Leu Thr Ile Thr Gly Val Gln Ala Asp Asp
65                  70                  75                  80

Glu Ala Val Tyr Phe Cys Gly Ser Ala Asp Ser Asn Thr Tyr Glu Gly
                85                  90                  95

Ser Phe Gly Ala Gly Thr Thr Leu Thr Val Leu
            100                 105

<210> SEQ ID NO 48
<211> LENGTH: 15
<212> TYPE: DNA
<213> ORGANISM: Artificial
<220> FEATURE:
<223> OTHER INFORMATION: Synthetic primer

<400> SEQUENCE: 48
agtcacgacg ttgta                                                        15

<210> SEQ ID NO 49
<211> LENGTH: 17

```
<212> TYPE: DNA
<213> ORGANISM: Artificial
<220> FEATURE:
<223> OTHER INFORMATION: Synthetic primer

<400> SEQUENCE: 49
caggaaacag ctatgac                                                        17

<210> SEQ ID NO 50
<211> LENGTH: 10
<212> TYPE: PRT
<213> ORGANISM: Gallus gallus

<400> SEQUENCE: 50

Ser Gly Gly Gly Ser Arg Asn Tyr Tyr Gly
1               5                   10

<210> SEQ ID NO 51
<211> LENGTH: 7
<212> TYPE: PRT
<213> ORGANISM: Gallus gallus

<400> SEQUENCE: 51

Asp Asp Gln Arg Pro Ser Asn
1               5

<210> SEQ ID NO 52
<211> LENGTH: 11
<212> TYPE: PRT
<213> ORGANISM: Gallus gallus

<400> SEQUENCE: 52

Ser Ala Asp Ser Asn Thr Tyr Glu Gly Ser Phe
1               5                   10

<210> SEQ ID NO 53
<211> LENGTH: 107
<212> TYPE: PRT
<213> ORGANISM: Gallus gallus

<400> SEQUENCE: 53

Ala Val Thr Gln Pro Pro Ala Ser Val Ser Ala Asn Pro Gly Glu Thr
1               5                   10                  15

Val Lys Ile Thr Cys Ser Gly Gly Ser Arg Asn Tyr Tyr Gly Trp
            20                  25                  30

Tyr Gln Gln Lys Ser Pro Gly Ser Val Pro Val Thr Val Ile Tyr Tyr
            35                  40                  45

Asp Asp Gln Arg Pro Ser Asn Ile Pro Ser Arg Phe Ser Gly Ala Leu
        50                  55                  60

Ser Gly Ser Thr Ser Thr Leu Thr Ile Thr Gly Val Gln Ala Asp Asp
65                  70                  75                  80

Glu Ala Val Tyr Phe Cys Gly Ser Ala Asp Ser Asn Thr Tyr Glu Gly
                85                  90                  95

Ser Phe Gly Ala Gly Thr Thr Leu Thr Val Leu
            100                 105

<210> SEQ ID NO 54
<211> LENGTH: 240
<212> TYPE: DNA
<213> ORGANISM: Gallus gallus

<400> SEQUENCE: 54
```

```
accatgagcc cactcgtctc ctccctcctg ctcctggccg ccctgccagg tgagggcgct    60
gtggggctct atgggctct atggggtctc agcggggctc tgcgggctca atggggggcca   120
aagggggggt ctgcgggctc tatgggggggg tcaacggggg gtctcacggg gggccggctc  180
cgcgaggccg tgtggcggcg gctccgtcag cgctttctgt ccttccccac agggcgcgcc   240
```

<210> SEQ ID NO 55
<211> LENGTH: 1807
<212> TYPE: DNA
<213> ORGANISM: Homo sapiens

<400> SEQUENCE: 55

```
ctttctgggg caggccaggc ctgaccttgg ctttggggca gggagggggc taaggtgagg    60
caggtggcgc cagccaggtg cacacccaat gcccatgagc ccagacactg gacgctgaac   120
ctcgcggaca gttaagaacc caggggcctc tgcgccctgg gccagctctg tcccacacc   180
gcggtcacat ggcaccacct ctcttgcagc ctccaccaag ggcccatcgg tcttcccct   240
ggcaccctcc tccaagagca cctctggggg cacagcggcc ctgggctgcc tggtcaagga   300
ctacttcccc gaaccggtga cggtgtcgtg gaactcaggc gccctgacca gcggcgtgca   360
caccttcccg gctgtcctac agtcctcagg actctactcc ctcagcagcg tggtgaccgt   420
gccctccagc agcttgggca cccagaccta catctgcaac gtgaatcaca agcccagcaa   480
caccaaggtg gacaagaaag ttggtgagag gccagcacag ggagggaggg tgtctgctgg   540
aagccaggct cagcgctcct gcctggacgc atcccggcta tgcagcccca gtccagggca   600
gcaaggcagg cccgtctgc ctcttcaccc ggaggcctct gcccgcccca ctcatgctca   660
gggagagggt cttctggctt tttccccagg ctctgggcag gcacaggcta ggtgccccta   720
acccaggccc tgcacacaaa ggggcaggtg ctgggctcag acctgccaag agccatatcc   780
gggaggaccc tgcccctgac ctaagcccac cccaaaggcc aaactctcca ctccctcagc   840
tcggacacct tctctcctcc cagattccag taactcccaa tcttctctct gcagagccca   900
aatcttgtga caaaactcac acatgcccac cgtgcccagg taagccagcc caggcctcgc   960
cctccagctc aaggcgggac aggtgcccta gagtagcctg catccaggga caggccccag  1020
ccgggtgctg acacgtccac ctccatctct tcctcagcac ctgaactcct ggggggaccg  1080
tcagtcttcc tcttcccccc aaaacccaag gacaccctca tgatctcccg gacccctgag  1140
gtcacatgcg tggtggtgga cgtgagccac gaagaccctg aggtcaagtt caactggtac  1200
gtggacggcg tggaggtgca taatgccaag acaaagccgc gggaggagca gtacaacagc  1260
acgtaccgtg tggtcagcgt cctcaccgtc ctgcaccagg actggctgaa tggcaaggag  1320
tacaagtgca aggtctccaa caaagccctc ccagccccca tcgagaaaac catctccaaa  1380
gccaaaggtg ggacccgtgg ggtgcgaggg ccacatggac agaggccggc tcggcccacc  1440
ctctgccctg agagtgaccg ctgtaccaac ctctgtccct acagggcagc cccgagaacc  1500
acaggtgtac accctgcccc catcccggga tgagctgacc aagaaccagg tcagcctgac  1560
ctgcctggtc aaaggcttct atcccagcga catcgccgtg gagtgggaga gcaatgggca  1620
gccggagaac aactacaaga ccacgcctcc cgtgctggac tccgacggct ccttcttcct  1680
ctacagcaag ctcaccgtgg acaagagcag gtggcagcag gggaacgtct tctcatgctc  1740
cgtgatgcat gaggctctgc acaaccacta cacgcagaag agcctctccc tgtctccggg  1800
taaatga                                                              1807
```

<210> SEQ ID NO 56
<211> LENGTH: 567
<212> TYPE: DNA
<213> ORGANISM: Homo sapiens

<400> SEQUENCE: 56

```
cagaatggct gcaaagagct ccaacaaaac aatttagaac tttattaagg ataggggga      60
agctaggaag aaactcaaaa catcaagatt ttaaatacgc ttcttggtct ccttgctata    120
attatctggg ataagcatgc tgttttctgt ctgtccctaa catgccctgt gattatccgc    180
aaacaacaca cccaagggca gaactttgtt acttaaacac catcctgttt gcttctttcc    240
tcaggaactg tggctgcacc atctgtcttc atcttcccgc catctgatga gcagttgaaa    300
tctggaactg cctctgttgt gtgcctgctg aataacttct atcccagaga ggccaaagta    360
cagtggaagg tggataacgc cctccaatcg ggtaactccc aggagagtgt cacagagcag    420
gacagcaagg acagcaccta cagcctcagc agcaccctga cgctgagcaa agcagactac    480
gagaaacaca agtctacgc ctgcgaagtc acccatcagg gcctgagctc gcccgtcaca    540
aagagcttca caggggaga gtgttag                                         567
```

<210> SEQ ID NO 57
<211> LENGTH: 384
<212> TYPE: DNA
<213> ORGANISM: Gallus gallus

<400> SEQUENCE: 57

```
gccgccgtga cgttggacga gtccgggggc ggcctccaga cgcccggagg agcgctcagc     60
ctcgtctgca aggcctccgg gttcaccttc agtggttatg acatgctctg ggtgcgacag    120
gcgcccggca aggggctgga gtgggtcgct ggtattggca gcactggtgg tggcacagac    180
tatggggcgg cggtgaaggg ccgtgccacc atctcgaggg acaacgggca gagcacagtg    240
aggctgcagc tgaacaacct cagggctgag gacaccgcca cctactactg cgccaaagtt    300
gctggtggtt gtaatagtgg ttattgtcgg gactctcccg gtagcatcga cgcatggggc    360
cacgggaccg aagtcatcgt gtcg                                           384
```

<210> SEQ ID NO 58
<211> LENGTH: 321
<212> TYPE: DNA
<213> ORGANISM: Gallus gallus

<400> SEQUENCE: 58

```
gcagtgactc agcagccggc ctcggtgtca gcaaacccag agaaaccgt caagatcacc      60
tgctccgggg gtggtagtag gaactactat ggctggtacc agcagaagtc tcctggcagt    120
gtccctgtca ctgtgatcta ctatgatgat cagagaccct cgaacatccc ttcacgattc    180
tccggtgccc tatccggctc cacaagcaca ttaaccatca ctgggtcca agccgacgac    240
gaggctgtct atttctgtgg gagtgcagac agcaacacct atgagggtag ctttggggcc    300
gggacaaccc tgaccgtcct a                                              321
```